United States Patent
Sagehashi et al.

(10) Patent No.: US 9,790,166 B2
(45) Date of Patent: Oct. 17, 2017

(54) POLYMER, MONOMER, RESIST COMPOSITION, AND PATTERNING PROCESS

(71) Applicant: SHIN-ETSU CHEMICAL CO., LTD., Tokyo (JP)

(72) Inventors: Masayoshi Sagehashi, Joetsu (JP); Koji Hasegawa, Joetsu (JP); Masahiro Fukushima, Joetsu (JP); Jun Hatakeyama, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/156,411

(22) Filed: May 17, 2016

(65) Prior Publication Data

US 2016/0342086 A1   Nov. 24, 2016

(30) Foreign Application Priority Data

May 19, 2015   (JP) .................................. 2015-101654

(51) Int. Cl.

| G03F 7/038 | (2006.01) |
| G03F 7/039 | (2006.01) |
| C07C 69/54 | (2006.01) |
| C08F 16/20 | (2006.01) |
| C08F 20/26 | (2006.01) |
| C08F 216/10 | (2006.01) |
| C08F 224/00 | (2006.01) |
| G03F 7/004 | (2006.01) |

(52) U.S. Cl.
CPC ............ *C07C 69/54* (2013.01); *C08F 216/10* (2013.01); *C08F 224/00* (2013.01); *G03F 7/0045* (2013.01); *G03F 7/0046* (2013.01); *G03F 7/0382* (2013.01); *C07C 2601/08* (2017.05); *C07C 2601/14* (2017.05); *C07C 2603/74* (2017.05)

(58) Field of Classification Search
None
See application file for complete search history.

(56) References Cited

U.S. PATENT DOCUMENTS

| 6,280,897 B1 * | 8/2001 | Asakawa ............... G03F 7/0045 430/270.1 |
| 6,800,423 B2 | 10/2004 | Yokoyama et al. |
| 7,300,739 B2 | 11/2007 | Allen et al. |
| 7,563,558 B2 | 7/2009 | Allen et al. |
| 8,227,183 B2 | 7/2012 | Tsubaki et al. |
| 2007/0026339 A1 * | 2/2007 | Allen ..................... C08F 220/24 430/270.1 |
| 2012/0148957 A1 * | 6/2012 | Enomoto .............. G03F 7/0382 430/285.1 |
| 2012/0308930 A1 * | 12/2012 | Hatakeyama ........... G03F 7/004 430/280.1 |
| 2014/0235057 A1 | 8/2014 | Hatakeyama et al. |
| 2014/0377706 A1 | 12/2014 | Hatakeyama et al. |

FOREIGN PATENT DOCUMENTS

| EP | 3 029 524 A1 | 6/2016 |
| JP | 2000-330287 | * 11/2000 |
| JP | 2000-330287 A | 11/2000 |
| JP | 2003-195502 A | 7/2003 |
| JP | 2004-347859 | * 12/2004 |
| JP | 2005-003862 A | 1/2005 |
| JP | 2005-003863 A | 1/2005 |
| JP | 2006-104353 | * 4/2006 |
| JP | 2006-145775 A | 6/2006 |
| JP | 2006-215067 A | 8/2006 |
| JP | 2006-317803 A | 11/2006 |
| JP | 4554665 B2 | 9/2010 |
| JP | 2012-058268 | * 3/2012 |
| TW | 201128305 A1 | 8/2011 |
| TW | 201437757 A | 10/2014 |
| TW | 201504774 A | 2/2015 |
| TW | 201512771 A | 4/2015 |
| WO | 2004/074936 A1 | 9/2004 |

OTHER PUBLICATIONS

Machine translation of JP 2006-215067 (2006).*
Machine translation of JP 2011-141495 (2011).*
Machine translation of JP 2009-053690 (2009).*
Machine translation of JP 2012-058268 (2012).*
Sooriyakumaran et al., "193-nm Negative Resist Based on Acid-Catalyzed Elimination of Polar Molecules", Advances in Resist Technology and Processing XXI, Proceedings of SPIE vol. 5376, pp. 71-78, 2004.
Office Action dated Dec. 19, 2016, issued in counterpart Taiwanese Patent Application No. 105115113. (9 pages).
Office Action dated Mar. 10, 2017, issued in counterpart Taiwanese Application No. 105115113. (11 pages).

* cited by examiner

*Primary Examiner* — Martin Angebranndt
(74) *Attorney, Agent, or Firm* — Westerman, Hattori, Daniels & Adrian, LLP

(57) ABSTRACT

A pattern forming process is provided comprising the steps of applying a resist composition comprising a polymer comprising recurring units having formula (1a) and/or (1b), an acid generator and a solvent onto a substrate, baking to form a resist film, exposing the resist film to high-energy radiation, baking, and developing in an alkaline developer to form a negative tone pattern.

9 Claims, 6 Drawing Sheets

POLYMER, MONOMER, RESIST COMPOSITION, AND PATTERNING PROCESS

CROSS-REFERENCE TO RELATED APPLICATION

This non-provisional application claims priority under 35 U.S.C. §119(a) on Patent Application No. 2015-101654 filed in Japan on May 19, 2015, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, the self-aligned double patterning (SADP) process of adding film to opposite sidewalls of lines of a resist pattern resulting from ArF lithography for thereby forming two patterns with half line width from one pattern is successful in manufacturing microelectronic devices at the 20-nm node in a mass scale. As the miniaturization technology for microelectronic devices of the next generation 10-nm node, the self-aligned quadruple patterning (SAQP) which is double repetition of SADP is a candidate. It is pointed out that this process is quite expensive because formation of sidewall film by CVD and processing by dry etching are repeated several times. Extreme ultraviolet (EUV) lithography of wavelength 13.5 nm is capable of forming a pattern with a size of the order of 10 nm via single exposure, but suffers from the problems of still low laser power and low productivity. As the miniaturization technology comes to the deadlock, the development of three-dimensional devices such as vertically stacked flash memories typically BiCS is started, but expected to be a high cost process.

Recently, a highlight is put on the organic solvent development again. A positive resist composition featuring a high resolution is subjected to organic solvent development to form a negative pattern. As the ArF resist composition for negative tone development with organic solvent, positive ArF resist compositions of the prior art design may be used. Such a pattern forming process is described in Patent Document 1.

In the process of forming a negative tone pattern via organic solvent development, a film from which a robust protective group such as cyclic structure having dry etch resistance has been eliminated is left as the negative pattern. Thus the film is short of dry etch resistance. This serious problem must be overcome before the negative pattern formation via organic solvent development can be implemented.

On the other hand, studies have also been made on the negative pattern formation via development in alkaline aqueous solution. Known resist compositions used in this process include a negative resist composition of polarity switch type comprising a base resin comprising recurring units having γ-hydroxycarboxylic acid which forms lactone ring by PEB (see Patent Document 2), a negative resist composition comprising a copolymer comprising alcoholic hydroxyl-containing (meth)acrylate units and fluoroalcohol-containing units and a crosslinker (see Patent Document 3), and negative resist compositions of crosslinking type comprising a crosslinker and a combination of α-hydroxyacrylate and lactone units (see Patent Document 4), α-hydroxyacrylate and fluoroalcohol units (see Patent Documents 5 to 7), and mono(meth)acryloyloxypinacol and fluoroalcohol units (see Patent Document 8).

Of these, Patent Document 2 describes a negative resist composition of polarity switch type, not resorting to crosslinking reaction, in which γ-hydroxycarboxylic acid units incur swell of the pattern after development. Patent Documents 3 to 7 relate to negative resist compositions of crosslinking type. Although the negative pattern formation by cooperation of alcoholic hydroxyl group and crosslinker has the problems of bridging between pattern features and pattern collapse due to swell, it is observed that the incorporation of fluoroalcohol units has a swell-reducing effect. Moreover, as recent examples of negative pattern formation by polarity switch, there are proposed base resins having polar units such as tertiary hydroxyl group, tertiary ether bond, tertiary ester bond or acetal bond as the polarity switch group. Of these, a polymer using a polar unit having one tertiary hydroxyl group is unlikely to swell after development. However, the difference of dissolution rate in developer between unexposed and exposed regions is insufficient, which raises the problem that a footing occurs at the bottom of a line-and-space pattern, that is, pattern features take a tapered shape. See Patent Documents 9 and 10 and Non-Patent Document 1.

All the negative pattern forming processes mentioned above are effective to some extent in forming pattern features with a size of the order of 100 nm. However, their performance is insufficient in forming pattern features with a size of finer than 100 nm, because pattern bridging and collapse due to swell, and footing at the pattern bottom inevitably occur. Although active efforts have recently been devoted on the negative pattern forming process via organic solvent development, the organic solvent used as the developer is more expensive than conventional alkaline developers. From the standpoint of etch resistance improvement, it is desired to have a negative resist composition which is amenable to conventional alkaline development at a high resolution and allows a robust backbone structure to be left in the film after development.

| Citation List | |
| --- | --- |
| Patent Document 1: | JP 4554665 (U.S. Pat. No. 8,227,183) |
| Patent Document 2: | JP-A 2003-195502 |
| Patent Document 3: | WO 2004/074936 |
| Patent Document 4: | JP-A 2005-003862 |
| Patent Document 5: | JP-A 2005-003863 |
| Patent Document 6: | JP-A 2006-145775 |
| Patent Document 7: | JP-A 2006-317803 |
| Patent Document 8: | JP-A 2006-215067 |
| Patent Document 9: | U.S. Pat. No. 7,300,739 |
| Patent Document 10: | U.S. Pat. No. 7,563,558 |
| Non-Patent Document 1: | Proc. SPIE vol. 5376, p71 (2004) |

DISCLOSURE OF INVENTION

The requirements for further miniaturization continue severer in these years. In the negative pattern forming process via organic solvent development, on which active efforts have been devoted, the negative pattern defined in the resist film has a reduced carbon density as compared with that prior to exposure. It remains outstanding to improve the resistance to etching of the resist film and the retention of pattern shape after etching.

An object of the invention is to provide a polymerizable monomer having a substituent group capable of polarity switch under the action of acid, a polymer derived from the monomer, a resist composition comprising the polymer, and a pattern forming process using the composition.

The inventors have found that a resist composition comprising a polymer comprising recurring units having the formula (1a) and/or (1b) as base resin forms at a high resolution a negative pattern insoluble in alkaline developer and having high etch resistance.

In one aspect, the invention provides a pattern forming process comprising the steps of applying a resist composition comprising a base resin, an acid generator and a solvent onto a substrate, baking to form a resist film, exposing the resist film to high-energy radiation to define exposed and unexposed regions, baking, and developing the exposed resist film in an alkaline developer in which the unexposed region of resist film is dissolved and the exposed region of resist film is not dissolved, to form a negative tone pattern. The base resin comprises a polymer comprising recurring units having the formula (1a) and/or (1b).

In another aspect, the invention provides a pattern forming process comprising the steps of applying a resist composition comprising a base resin, an acid generator and a solvent onto a substrate, baking to form a resist film, exposing the resist film to high-energy radiation to define exposed and unexposed regions, baking, and developing the exposed resist film in an alkaline developer in which the unexposed region of resist film is dissolved and the exposed region of resist film is not dissolved, to form a negative tone pattern. The base resin comprises a polymer comprising recurring units having the formula (1a) and/or (1b) and recurring units of at least one type selected from the formulae (f1) to (f3).

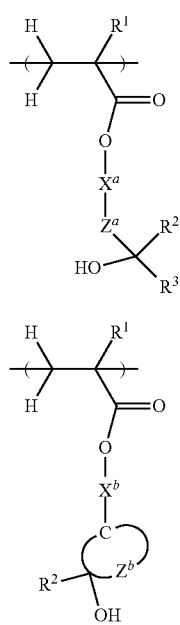

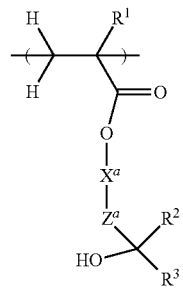

Herein $R^1$, $R^2$, $R^3$, $X^a$, $X^b$, $Z^a$, and $Z^b$ are as defined above.

Herein $R^1$ is hydrogen or methyl, $R^2$ and $R^3$ are each independently a straight, branched or cyclic $C_1$-$C_6$ monovalent hydrocarbon group, $R^2$ and $R^3$ may bond together to form an alicyclic group with the carbon atom to which they are attached, $X^a$ and $X^b$ are each independently a single bond, methylene or ethylidene, $Z^a$ is a straight, branched or cyclic $C_1$-$C_9$ divalent aliphatic hydrocarbon group, $Z^b$ is an atomic group necessary to form a $C_3$-$C_{10}$ alicyclic group with the carbon atoms to which it is attached, with the proviso that the total number of carbon atoms in each formula is such as to meet $6 \leq X^a + Z^a + R^2 + R^3 \leq 12$ when $Z^a$ is acyclic, or $5 \leq X^a + Z^a + R^2 + R^3 \leq 12$ when $Z^a$ is cyclic, and $5 \leq X^b + Z^b + R^2 \leq 12$.

(f3)

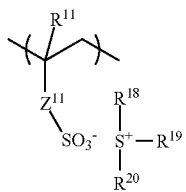

Herein $R^{11}$ is independently hydrogen or methyl, $R^{12}$ is a single bond, phenylene, —O—$R^{21}$—, or —C(=O)—$Z^{22}$—$R^{21}$—, $Z^{22}$ is oxygen or NH, $R^{21}$ is a straight, branched or cyclic $C_1$-$C_6$ alkylene, straight, branched or cyclic $C_2$-$C_6$ alkenylene or phenylene group, which may contain a carbonyl (—CO—), ester (—COO—), ether (—O—) or hydroxyl moiety, L is a single bond or —$Z^{33}$—C(=O)—O—, $Z^{33}$ is a straight, branched or cyclic $C_1$-$C_{20}$ divalent hydrocarbon group which may be substituted with a heteroatom, $Z^{11}$ is a single bond, methylene, ethylene, phenylene, fluorinated phenylene, —O—$R^{22}$—, or —C(=O)—$Z^{44}$—$R^{22}$—, $Z^{44}$ is oxygen or NH, $R^{22}$ is a straight, branched or cyclic $C_1$-$C_6$ alkylene, straight, branched or cyclic $C_2$-$C_6$ alkenylene or phenylene group, which may contain a carbonyl, ester, ether or hydroxyl moiety, $R^{13}$ to $R^{20}$ are each independently a straight, branched or cyclic $C_1$-$C_{20}$ monovalent hydrocarbon group which may be substituted with or separated by a heteroatom, and $M^-$ is a non-nucleophilic counter ion.

In a further aspect, the invention provides a polymer comprising recurring units having the formula (1b).

(Ib)

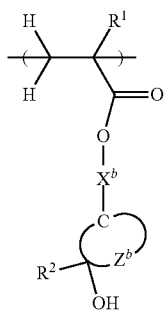

Herein $R^1$ is hydrogen or methyl, $R^2$ is a straight, branched or cyclic $C_1$-$C_6$ monovalent hydrocarbon group, $X^b$ is a single bond, methylene or ethylidene, $Z^b$ is an atomic group necessary to form a $C_3$-$C_{10}$ alicyclic group with the carbon atoms to which it is attached, with the proviso that the total number of carbon atoms in the formula is such as to meet $5 \leq X^b + Z^b + R^2 \leq 12$.

In a still further aspect, the invention provides a polymer comprising recurring units having the formula (1a) and/or (1b) and recurring units having the formula (1c):

(1a)

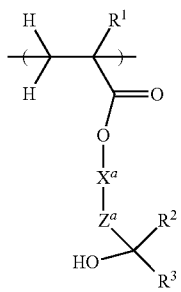

(1b)

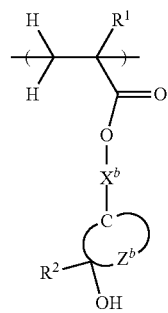

(1c)

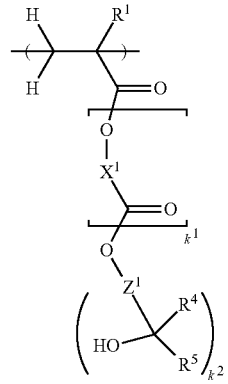

Herein $R^1$, $R^2$, $R^3$, $X^a$, $X^b$, $Z^a$, and $Z^b$ are as defined above. $R^4$ and $R^5$ are each independently a straight, branched or cyclic $C_1$-$C_{10}$ monovalent hydrocarbon group, $R^4$ and $R^5$ may bond together to form an alicyclic group with the carbon atom to which they are attached, $X^1$ is a straight, branched or cyclic $C_1$-$C_{20}$ divalent hydrocarbon group in which any constituent —$CH_2$— moiety may be replaced by —O— or —C(=O)—, $Z^1$ is a straight, branched or cyclic $C_1$-$C_{20}$ tri- to pentavalent aliphatic hydrocarbon group in which any constituent —$CH_2$— moiety may be replaced by —O— or —C(=O)—, $k^1$ is 0 or 1, and $k^2$ is an integer of 2 to 4.

In a still further aspect, the invention provides a polymer comprising recurring units having the formula (1a) and/or (1b) and recurring units of at least one type selected from the formulae (A) to (D).

(Ia)

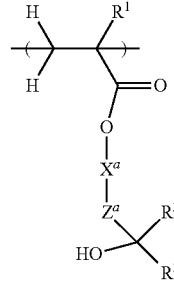

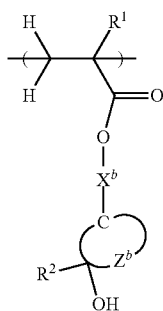

(Ib)

Herein $R^1$, $R^2$, $R^3$, $X^a$, $X^b$, $Z^a$, and $Z^b$ are as defined above.

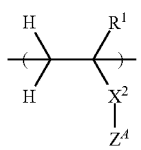

(A)

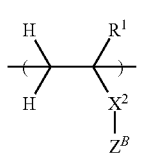

(B)

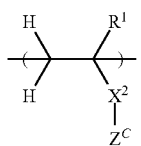

(C)

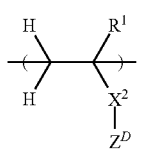

(D)

Herein $R^1$ is hydrogen or methyl, $Z^A$ is a $C_1$-$C_{20}$ fluoroalcohol-containing group, $Z^B$ is a $C_1$-$C_{20}$ phenolic hydroxyl-containing group, $Z^C$ is a $C_1$-$C_{20}$ carboxyl-containing group, $Z^D$ is a group containing a lactone structure, sultone structure, carbonate structure, cyclic ether structure, acid anhydride structure, alcoholic hydroxyl moiety, alkoxycarbonyl moiety, sulfonamide moiety or carbamoyl moiety, $X^2$ is a single bond, methylene, ethylene, phenylene, fluorinated phenylene, naphthylene, —O—$R^{O1}$—, or —C(=O)—$Z^2$—$R^{O1}$—, $Z^2$ is oxygen or NH, $R^{O1}$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

In a preferred embodiment, the polymer may further comprise recurring units having the formula (1c).

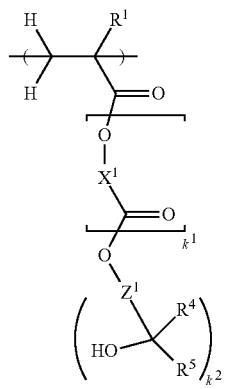

(1c)

Herein $R^1$ is hydrogen or methyl, $R^4$ and $R^5$ are each independently a straight, branched or cyclic $C_1$-$C_{10}$ monovalent hydrocarbon group, $R^4$ and $R^5$ may bond together to form an alicyclic group with the carbon atom to which they are attached, $X^1$ is a straight, branched or cyclic $C_1$-$C_{20}$ divalent hydrocarbon group in which any constituent —$CH_2$— moiety may be replaced by —O— or —C(=O)—, $Z^1$ is a straight, branched or cyclic $C_1$-$C_{20}$ tri- to pentavalent aliphatic hydrocarbon group in which any constituent —$CH_2$— moiety may be replaced by —O— or —C(=O)—, $k^1$ is 0 or 1, and $k^2$ is an integer of 2 to 4.

In a preferred embodiment, the polymer may further comprise recurring units of at least one type selected from the formulae (f1) to (f3).

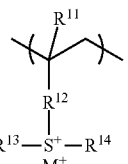

(f1)

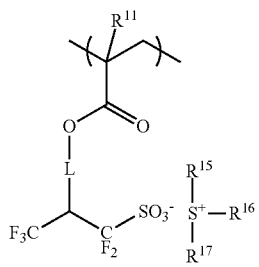

(f2)

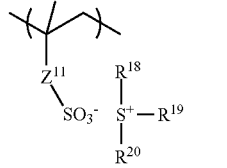

(f3)

Herein $R^{11}$ to $R^{20}$, L, $Z^{11}$, and $M^-$ are as defined above.

In a still further aspect, the invention provides a resist composition comprising a base resin comprising the polymer defined above, an acid generator, and an organic solvent; or a resist composition comprising a base resin comprising the polymer defined above, and an organic solvent.

In a still further aspect, the invention provides a pattern forming process comprising the steps of applying the resist composition defined above onto a substrate, baking to form a resist film, exposing the resist film to high-energy radiation, baking, and developing the exposed resist film in a developer to form a pattern. In a preferred embodiment, the developing step uses an alkaline developer in which an unexposed region of the resist film is dissolved and an exposed region of the resist film is not dissolved, for forming a negative tone pattern.

Also contemplated herein is a monomer having the formula (2b).

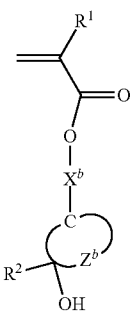

(2b)

Herein $R^1$, $R^2$, $X^b$, and $Z^b$ are as defined above.

Advantageous Effects of Invention

The resist composition comprising a polymer comprising recurring units of specific structure as base resin has high transparency to radiation of wavelength 500 nm or less, especially 300 nm or less, e.g., KrF, ArF or $F_2$ laser radiation, and improved development properties. The resist composition is quite useful because a negative pattern insoluble in alkaline developer and having high etch resistance can be formed therefrom at a high resolution.

DESCRIPTION OF EMBODIMENTS

Figure 1:
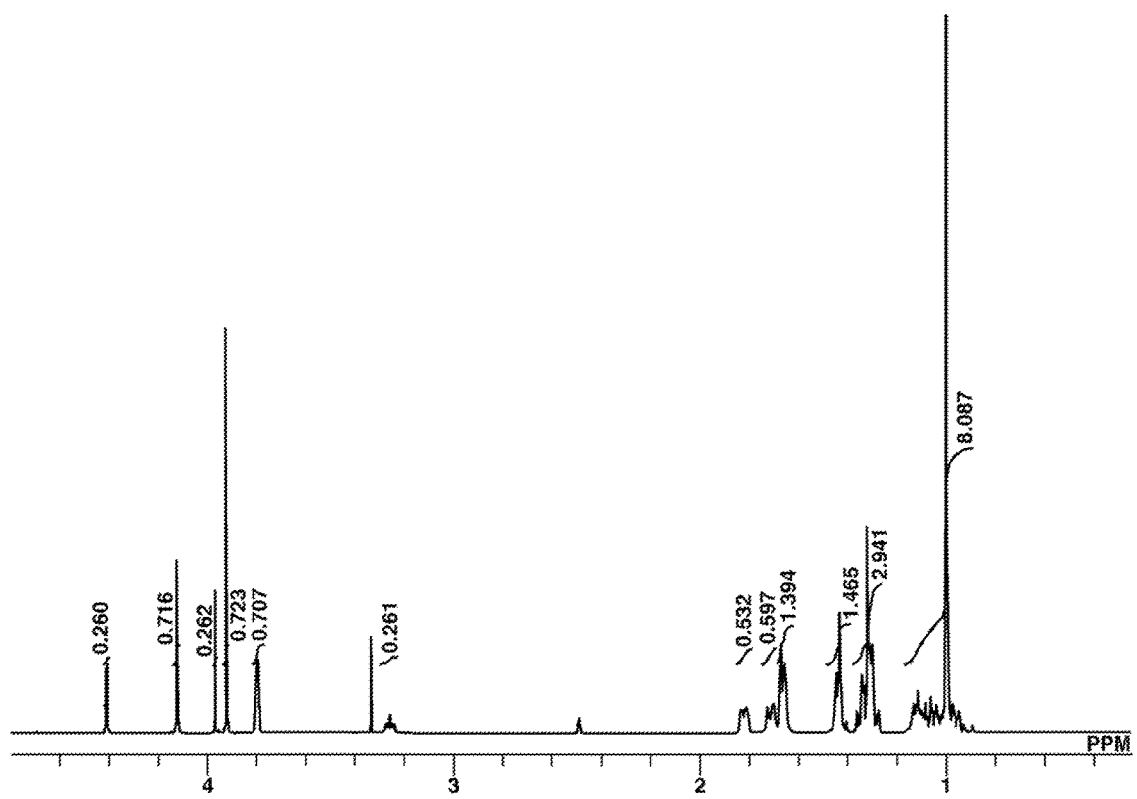
FIG. 1 is a diagram showing $^1$H-NMR spectrum of Diol 1 in Example 1-1.

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond. Me stands for methyl, Ph for phenyl, and Ac for acetyl.

The abbreviations and acronyms have the following meaning.

EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake
LWR: line width roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Polymer

The resist composition of the invention is characterized by comprising a polymer comprising recurring units having the formula (1a) and/or (1b) as a base resin.

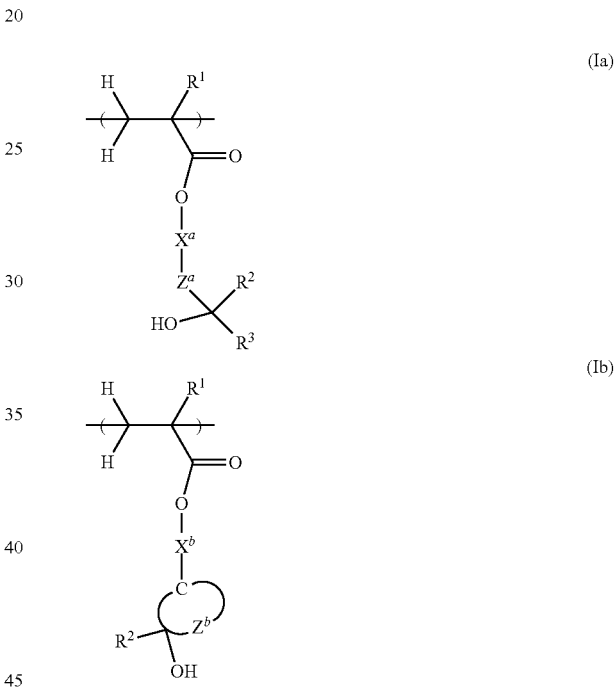

Herein $R^1$ is hydrogen or methyl, $R^2$ and $R^3$ are each independently a straight, branched or cyclic $C_1$-$C_6$ monovalent hydrocarbon group, $R^2$ and $R^3$ may bond together to form an alicyclic group with the carbon atom to which they are attached, $X^a$ and $X^b$ are each independently a single bond, methylene or ethylidene, $Z^a$ is a straight, branched or cyclic $C_1$-$C_9$ divalent aliphatic hydrocarbon group, $Z^b$ is an atomic group necessary to form a $C_3$-$C_{10}$ alicyclic group with the carbon atoms to which it is attached, with the proviso that the total number of carbon atoms in each formula is such as to meet $6 \leq X^a + Z^a + R^2 + R^3 \leq 12$ when $Z^a$ is acyclic, or $5 \leq X^a + Z^a + R^2 + R^3 \leq 12$ when $Z^a$ is cyclic, and $5 \leq X^b + Z^b + R^2 \leq 12$.

Typical of the straight, branched or cyclic $C_1$-$C_6$ monovalent hydrocarbon group represented by $R^2$ and $R^3$ are methyl, ethyl, propyl, isopropyl, n-butyl, s-butyl, t-butyl, cyclopentyl, and cyclohexyl.

When $R^2$ and $R^3$ bond together to form an alicyclic group with the carbon atom to which they are attached, suitable alicyclic groups include cyclopropane, cyclobutane, cyclopentane and cyclohexane rings.

Examples of the straight, branched or cyclic $C_1$-$C_9$ divalent aliphatic hydrocarbon group represented by $Z^a$ are shown below.

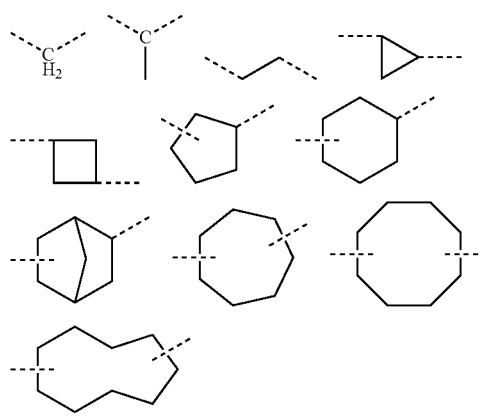

$Z^b$ is an atomic group necessary to form a $C_3$-$C_{10}$ alicyclic group with the carbon atoms to which it is attached, and examples of the alicyclic group are shown below.

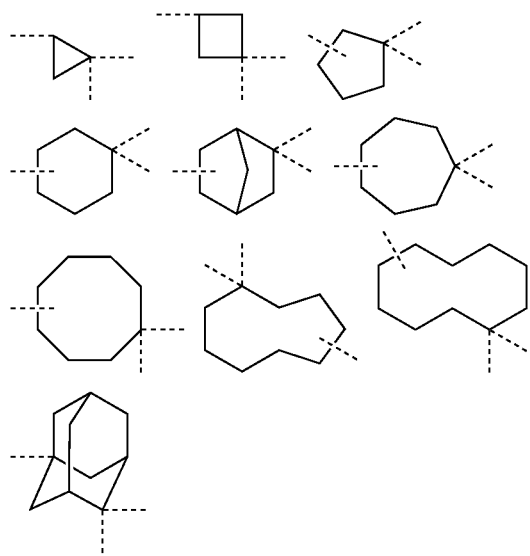

Examples of suitable recurring units having formulae (1a) and (1b) are shown below, but not limited thereto.

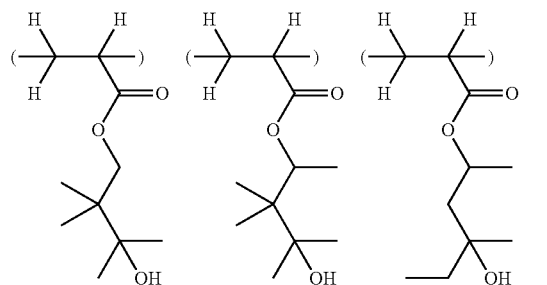

-continued

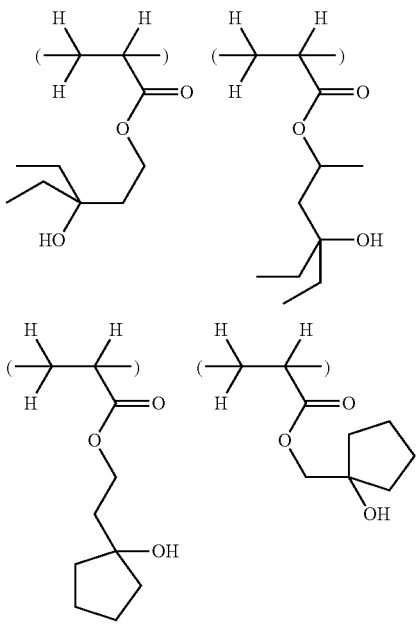

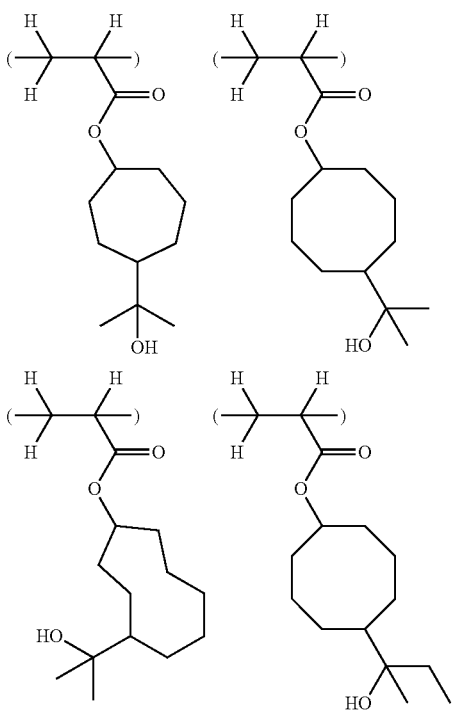

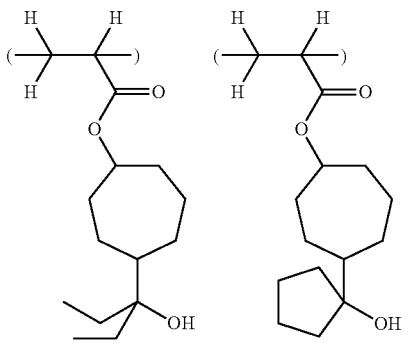

-continued
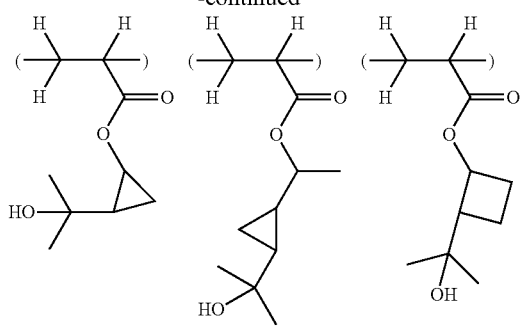
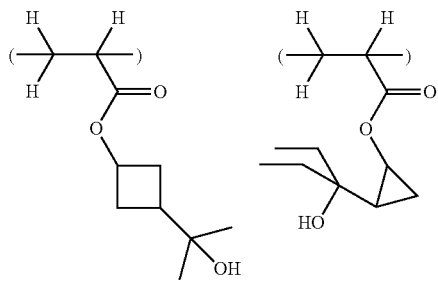
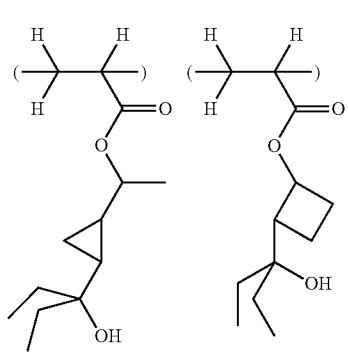
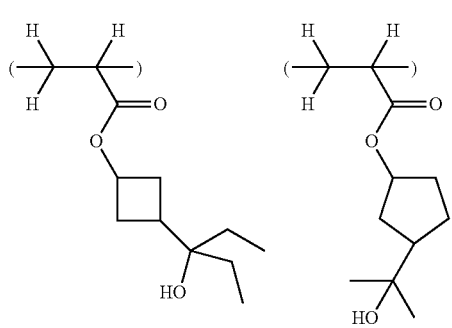
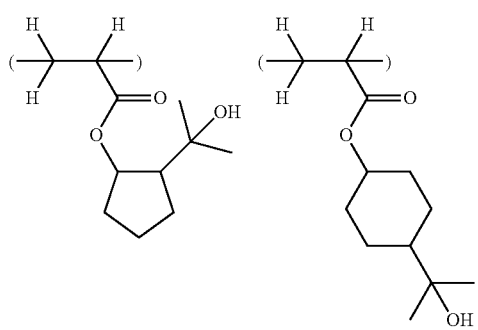
-continued
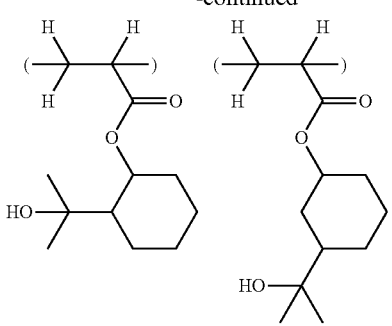
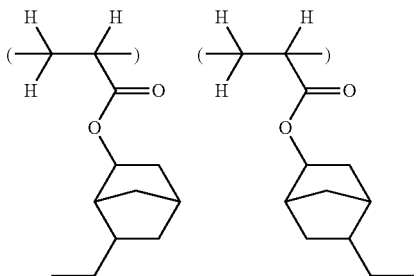
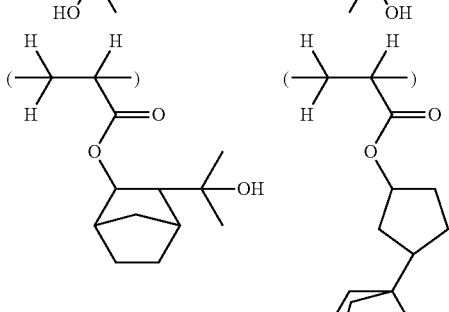
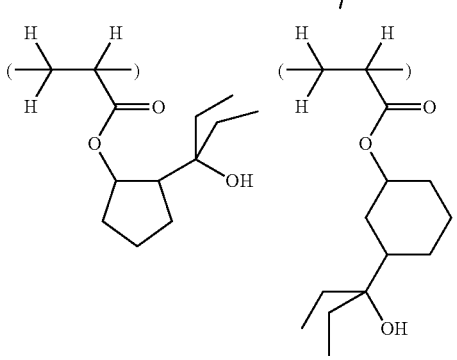
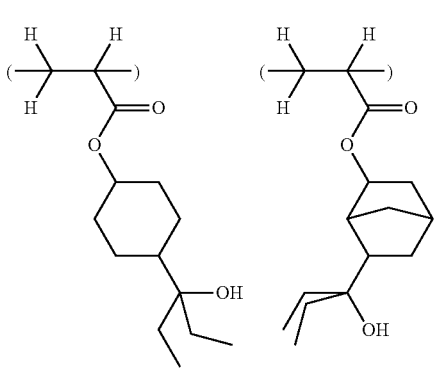

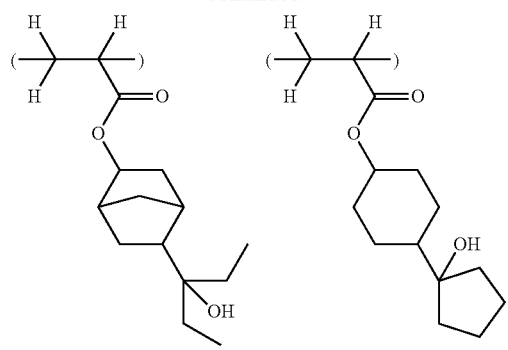
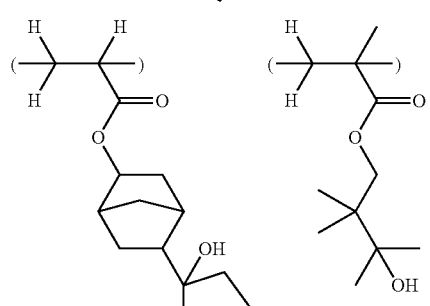
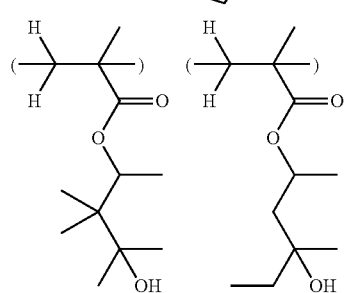
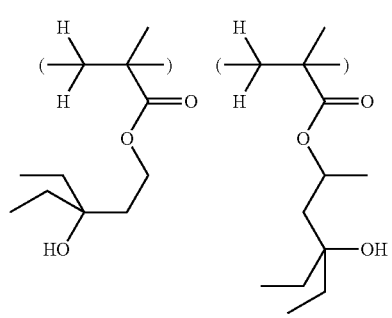
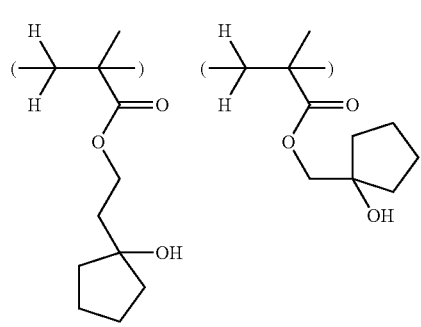
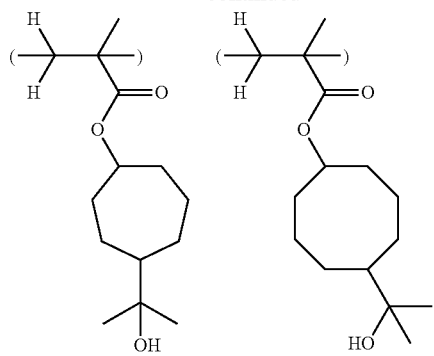
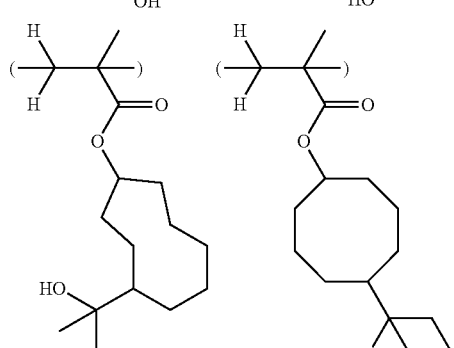
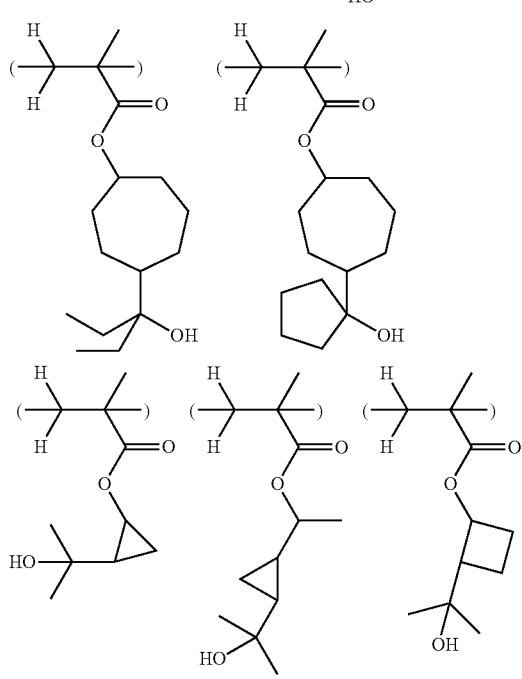
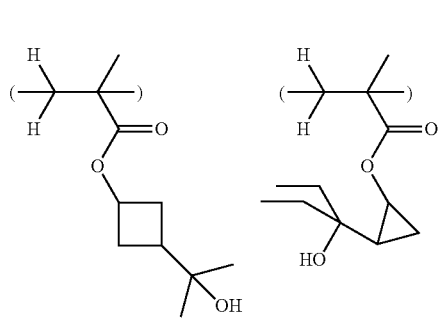

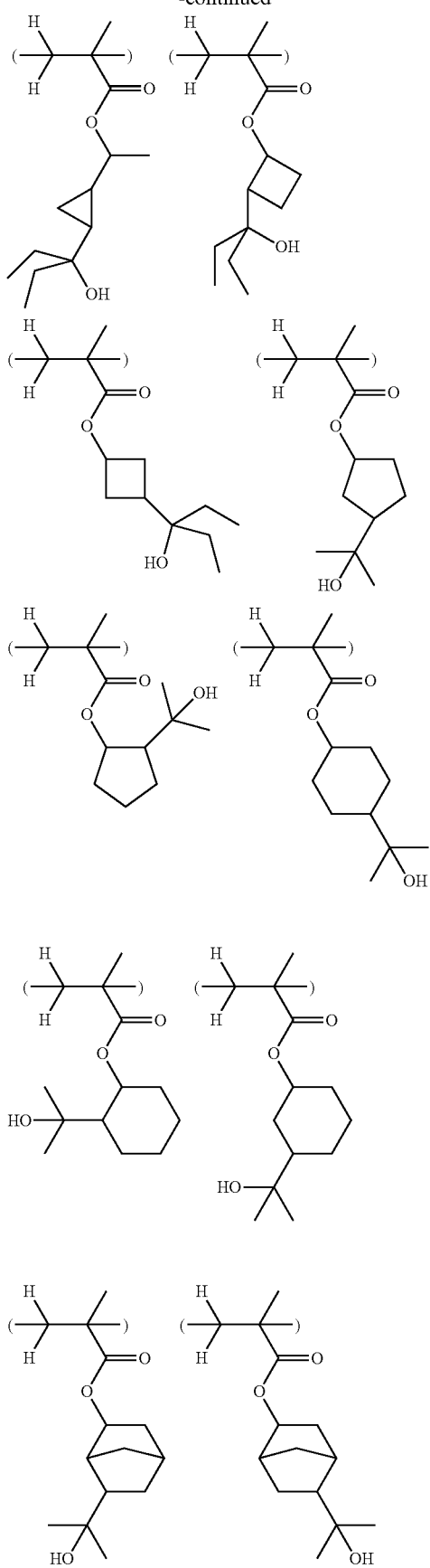
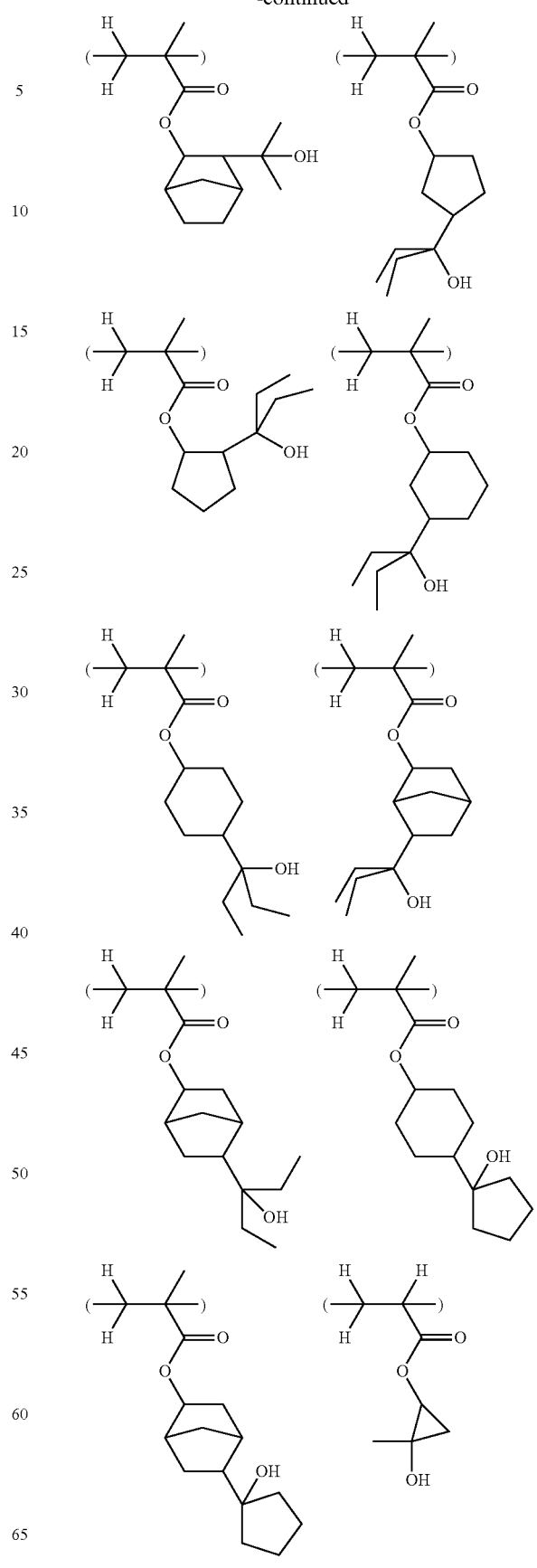

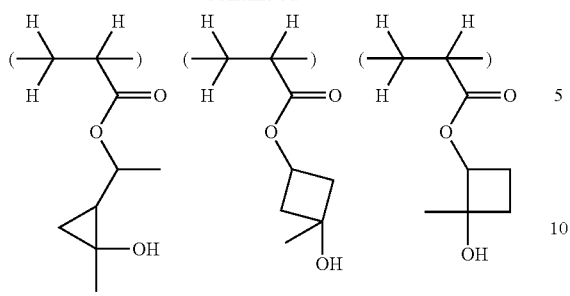
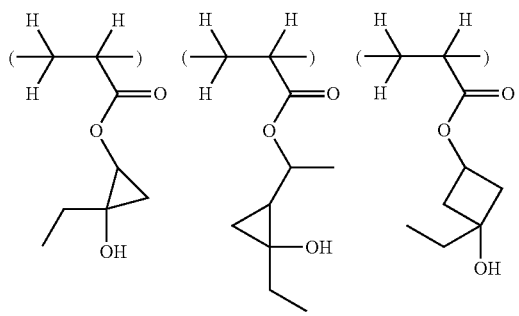
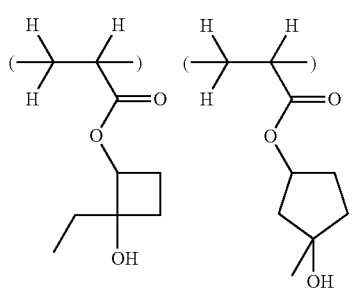
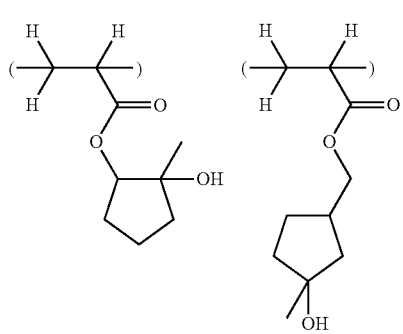
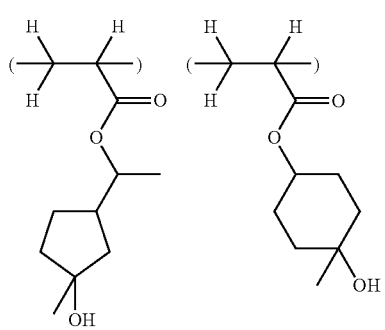
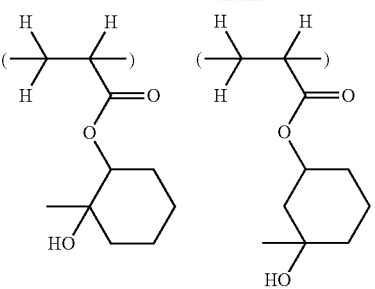
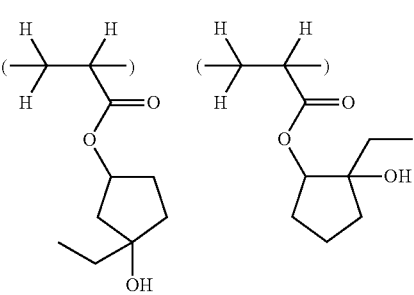
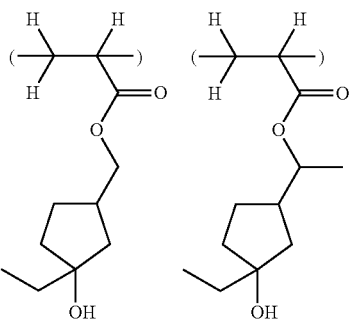
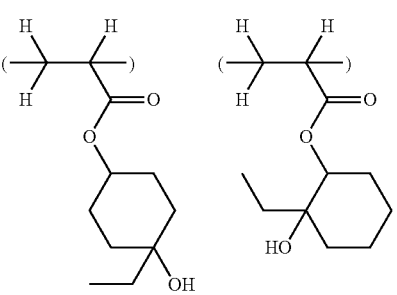
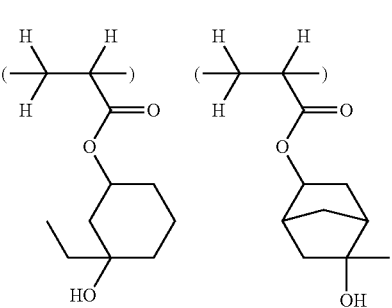

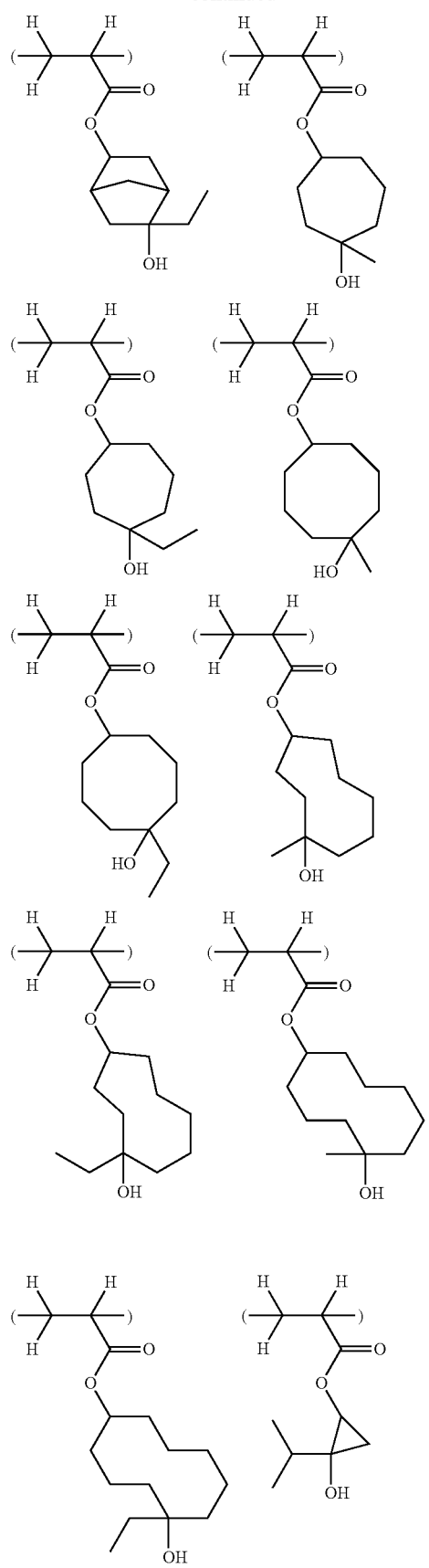
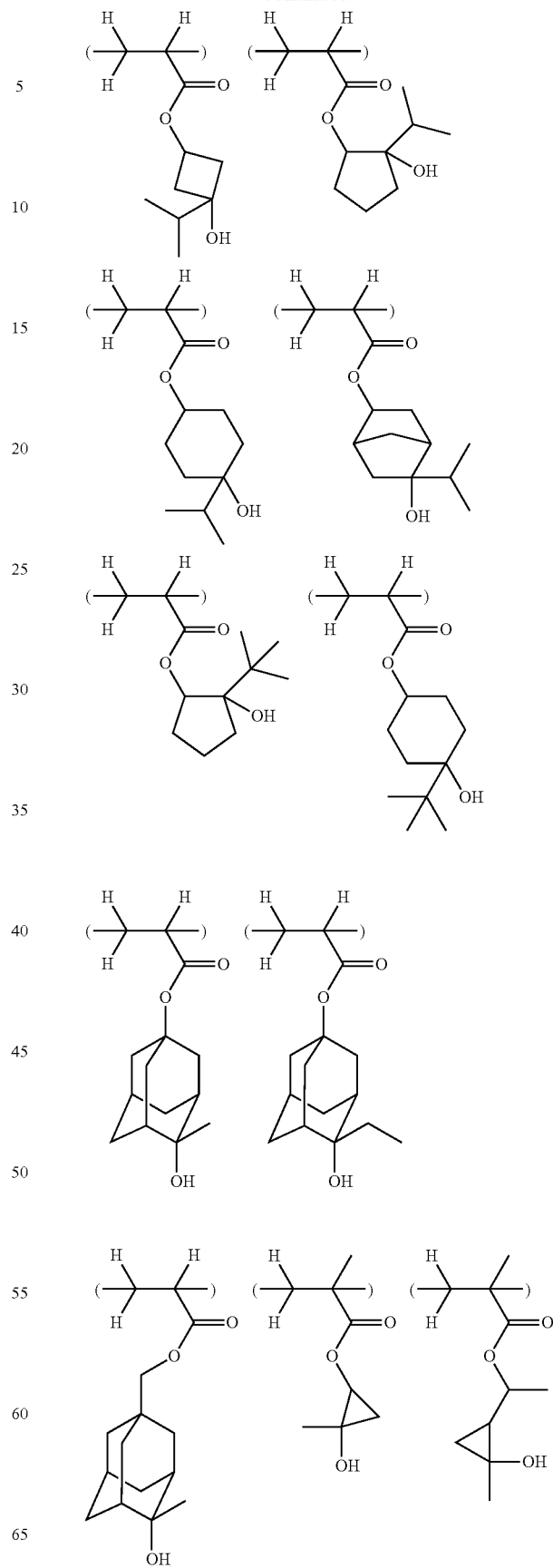

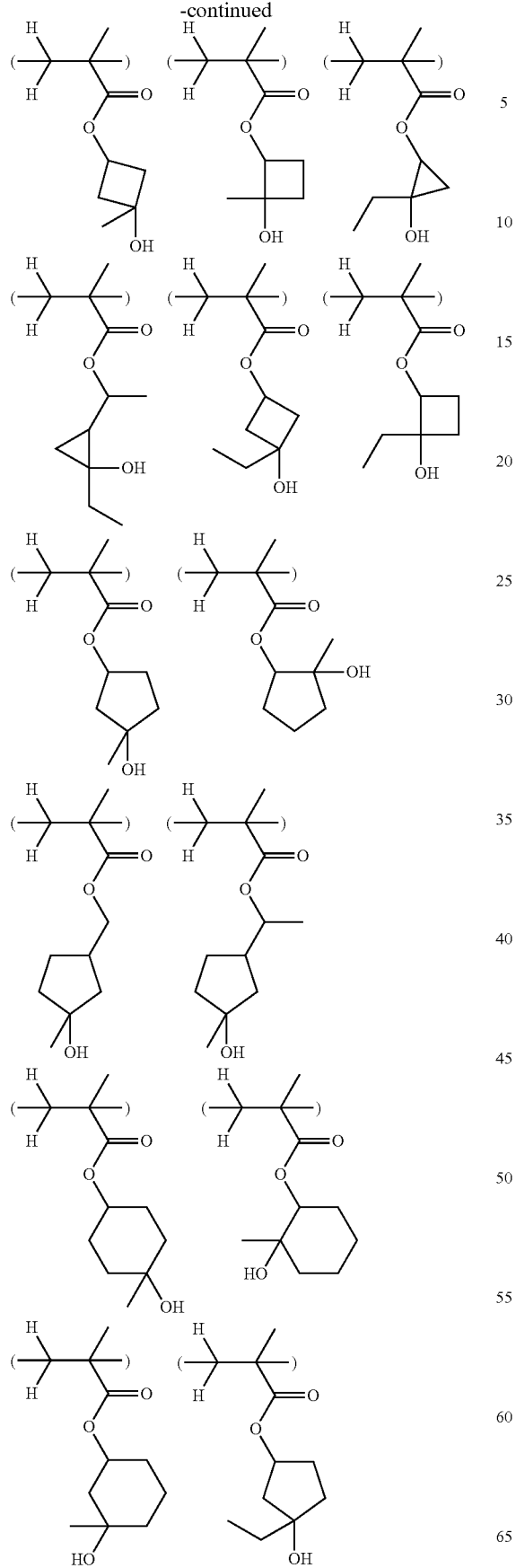
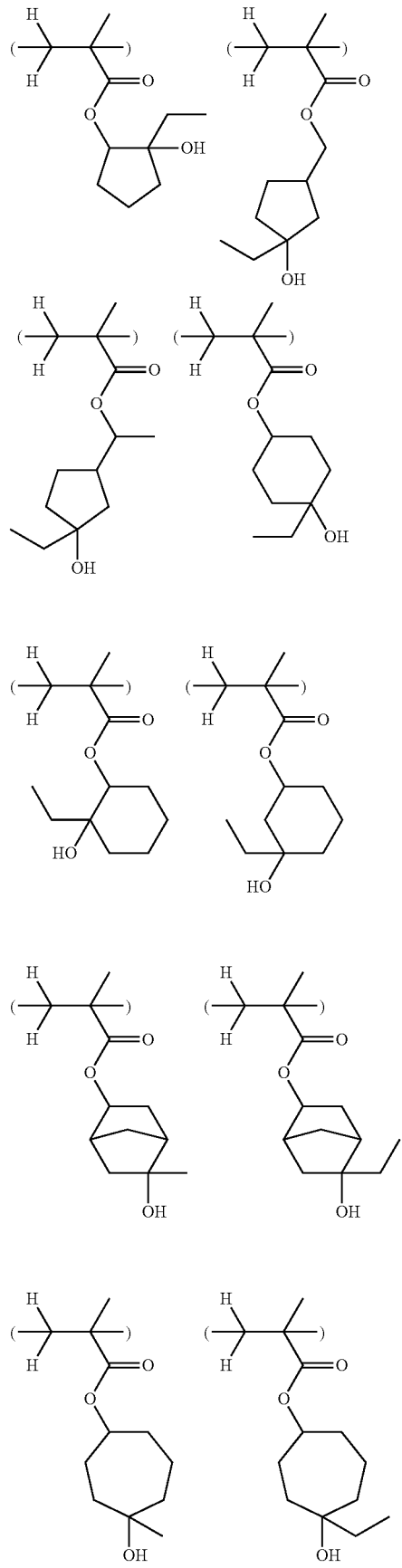

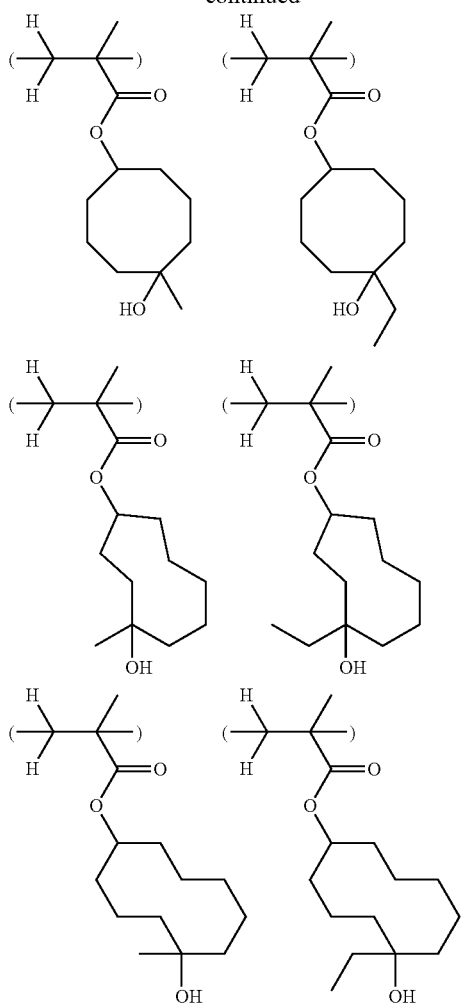
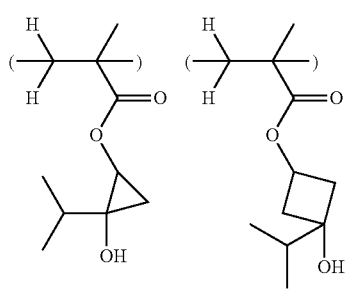
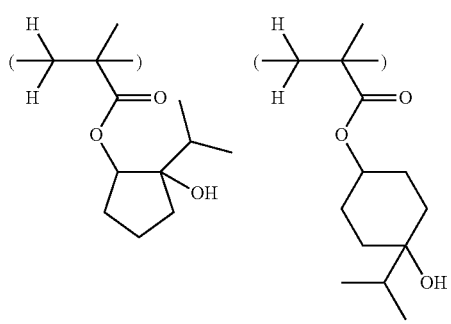
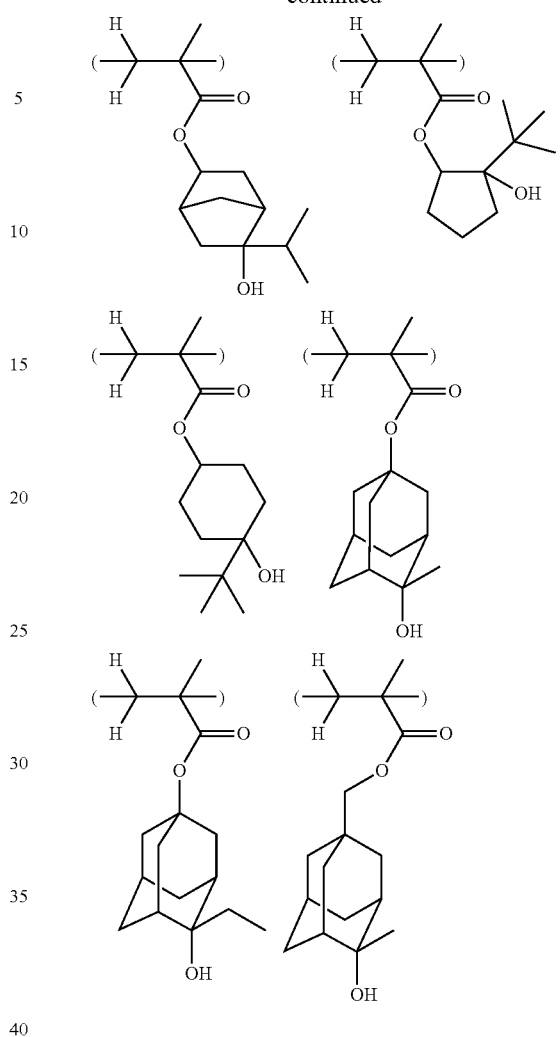

Each of the recurring units having formulae (1a) and (1b) has one tertiary alcoholic hydroxyl group as an acid labile group. Thus, in a resist composition using a polymer comprising such recurring units as base resin, after exposure, a process of eliminating a water molecule (referred to as "dehydration", hereinafter), under the action of strong acid generated in the exposed region, to form an olefin takes place. This process is illustrated below by referring to formula (1a-1) or (1b-1) corresponding to formula (1a) or (1b) wherein $R^2$ is methyl, as a typical example.

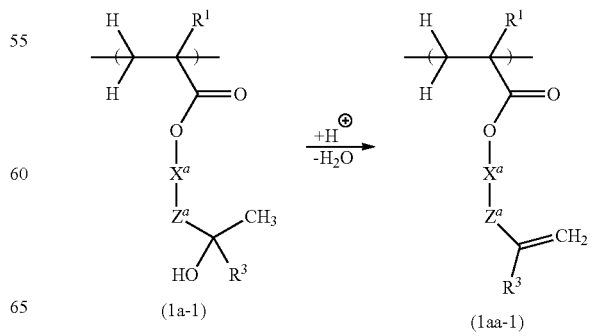

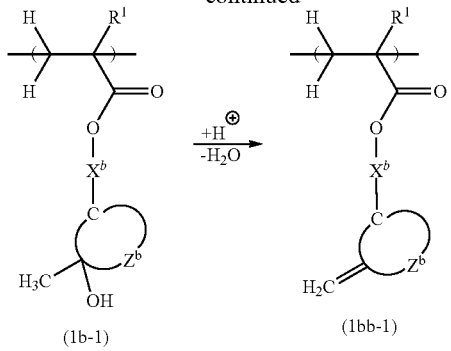

(1b-1)      (1bb-1)

Herein $R^1$, $R^3$, $X^a$, $X^b$, $Z^a$, and $Z^b$ are as defined above.

From the above-exemplified process, the following understanding is derived. Prior to exposure, the polymer has a high affinity to and high solubility in alkaline developer due to the presence of hydroxyl groups which are hydrophilic groups. After exposure, hydroxyl groups are lost in the exposed region of resist film, indicating a substantial drop of solubility in alkaline developer, that is, the exposed region becoming insolubilized in the developer. In addition, since only water molecule is lost after polarity switch, a change of carbon density is extremely small. Particularly when the polymer has a cyclic hydrocarbon group in its structure, only a polarity switch occurs while maintaining the robust alicyclic structure. That is, since the inventive polymer shows a very high dissolution contrast relative to alkaline developer, it serves as a base resin component which does not necessarily need insolubilization by a crosslinker. Since the polymer maintains a high carbon density and resin film thickness even after the polarity switch, it is less susceptible to bridging between pattern features and pattern collapse due to swell, which are considered problematic with negative resist materials of conventional polarity switch type and negative resist materials of crosslinking reaction type. In addition, the polymer has improved etch resistance. Consequently a finer size pattern can be resolved.

With respect to the recurring units corresponding to the structure of formula (1a), their use as a base resin in positive resist compositions is reported in the prior art (JP-A 2007-322660). Since this patent document intends to use a polymer as a base resin in a positive resist composition such that the exposed region of resist film may have an increased solubility in alkaline developer, in fact, a copolymer comprising recurring units of formula (1a) and recurring units of (meth)acrylic acid having a high affinity to alkaline developer, protected with an acid labile group is used as the base resin. The present invention is essentially different from the previous technology because it pertains to a negative resist composition wherein the exposed region of resist film has a reduced solubility in alkaline developer and becomes insolubilized in the developer.

In this sense, the inventive polymer does not contain recurring units having the following formula (i):

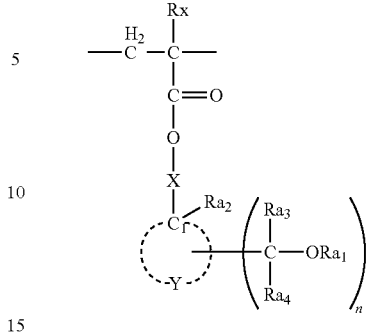

wherein Rx is hydrogen, alkyl or cyano, $Ra_1$ and $Ra_2$ are each independently hydrogen or an organic group, $Ra_3$ and $Ra_4$ are each independently an organic group, $Ra_3$ and $Ra_4$ may bond together to form a cyclic structure, X is a single bond or alkylene group, Y is an atomic group necessary to form a monocyclic hydrocarbon group with the carbon atom $C_1$, and n is 1 or 2.

To meet both a high solubility in alkaline developer of the unexposed region and a drop of solubility in alkaline developer of olefin formed in the exposed region, the total number of carbon atoms (exclusive of polymerizable functionality) in each of structural units of formulae (1a) and (1b) is such as to meet $6 \leq X^a + Z^a + R^2 + R^3 \leq 12$ when $Z^a$ is acyclic, or $5 \leq X^a + Z^a + R^2 + R^3 \leq 12$ when $Z^a$ is cyclic, and $5 \leq X^b + Z^b + R^2 \leq 12$. If the carbon count is less than 5, the unexposed region has a very high hydrophilicity and a high dissolution rate in developer, but a problem arises that the resist film at the boundary between exposed and unexposed regions is liable to swell by entrapping alkaline aqueous solution. If the carbon count exceeds 12, then the dissolution rate of the unexposed region in alkaline aqueous solution is reduced, and the dissolution contrast, that is, the difference in dissolution rate between exposed and unexposed regions is undesirably reduced.

In the recurring unit of formula (1a), $Z^a$ is preferably an alicyclic group, most preferably cyclopentane or cyclohexane ring because it is advantageous for acid diffusion length control and etch resistance. Likewise, in the recurring unit of formula (1b), the alicyclic group formed by $Z^b$ is preferably cyclopentane, cyclohexane or adamantane ring.

The monomers from which the recurring units having formulae (1a) and (1b) are derived have the following formulae (2a) and (2b), respectively.

(2a)

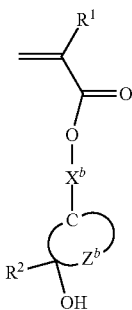

(2b)

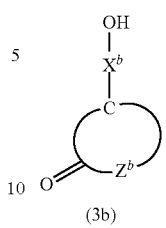

(3b)

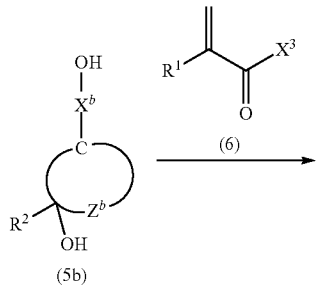

(5b)

Herein $R^1$ is hydrogen or methyl, $R^2$ and $R^3$ are each independently a straight, branched or cyclic $C_1$-$C_6$ monovalent hydrocarbon group, $R^2$ and $R^3$ may bond together to form an alicyclic group with the carbon atom to which they are attached, $X^a$ and $X^b$ are each independently a single bond, methylene or ethylidene, $Z^a$ is a straight, branched or cyclic $C_1$-$C_9$ divalent aliphatic hydrocarbon group, $Z^b$ is an atomic group necessary to form a $C_3$-$C_{10}$ alicyclic group with the carbon atoms to which it is attached, with the proviso that the total number of carbon atoms in each formula is such as to meet $6 \leq X^a + Z^a + R^2 + R^3 \leq 12$ when $Z^a$ is acyclic, or $5 \leq X^a + Z^a + R^2 + R^3 \leq 12$ when $Z^a$ is cyclic, and $5 \leq X^b + Z^b + R^2 + R^2 \leq 12$.

The monomers having formulae (2a) and (2b) may be synthesized by reactions as shown below although the synthesis route is not limited thereto.

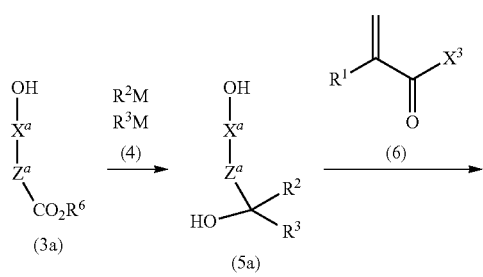

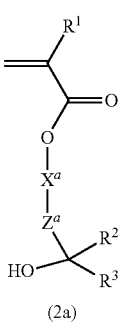

(2a)

Herein $R^1$ to $R^3$, $X^a$, and $Z^a$ are as defined above, with the proviso that the total carbon count is such as to meet $5 \leq X^a + Z^a + R^2 + R^3 \leq 12$. $R^6$ is a straight, branched or cyclic $C_1$-$C_{10}$ monovalent hydrocarbon group. $X^3$ is a halogen atom, hydroxyl group or acyloxy group. M is Li, Na, K, MgX or ZnX wherein X is a halogen atom.

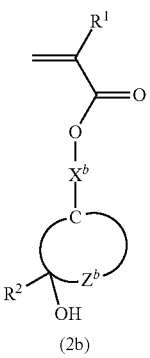

(2b)

Herein $R^1$, $R^2$, $X^b$, and $Z^b$ are as defined above, with the proviso that the total carbon count is such as to meet $5 \leq X^b + Z^b + R^2 \leq 12$. $X^3$ is a halogen atom, hydroxyl group or acyloxy group. M is Li, Na, K, MgX or ZnX wherein X is a halogen atom.

The first stage is addition reaction of a hydroxy-ester compound (3a) or hydroxy-ketone compound (3b) with an organometallic reagent (4) to form a diol compound (5a) or 5b).

The reaction may be performed by a standard procedure. For example, hydroxy-ester compound (3a) or hydroxy-ketone compound (3b) is dissolved in an ether solvent such as tetrahydrofuran or diethyl ether, then organometallic reagent (4) corresponding to substituent groups $R^2$ and $R^3$, for example, a Grignard reagent such as methylmagnesium chloride or ethylmagnesium chloride or alkyl-lithium reagent such as methyllithium is added to the solution, whereby addition reaction takes place to form diol compound (5a) or (5b) having tertiary alcohol. An appropriate amount of organometallic reagent (4) used is 3.0 to 10.0 moles, more preferably 3.0 to 5.0 moles per mole of the ester group of hydroxy-ester compound (3a) or hydroxy-ketone compound (3b). Less than 3.0 moles of organometallic reagent (4) may be too small for the addition reaction to the ester group to take place to completion, because 1 mole of organometallic reagent (4) is consumed by the hydroxyl group of hydroxy-ester compound (3a) or hydroxy-ketone compound (3b). More than 10.0 moles of organometallic reagent (4) may be disadvantageous in cost because of increased reactant expense. The reaction may be performed while cooling or heating if necessary, typically at a temperature of 0° C. to about the boiling point of the solvent. It is desirable from the standpoint of yield that the reaction time is determined so as to drive the reaction to completion by monitoring the reaction process by gas chromatography (GC) or silica gel thin-layer chromatography (TLC). Usually, the reaction time is about 0.5 to 24 hours. From the reaction mixture, the desired diol compound (5a) or (5b) is recovered through an ordinary aqueous workup. If necessary, the compound may be purified by a standard technique such as distillation, chromatography or recrystallization.

The second stage is reaction of diol compound (5a) or (5b) with an esterifying agent (6) to form monomer (2a) or (2b).

The reaction may be performed by a standard procedure. The preferred esterifying agent (6) is an acid chloride of formula (6) wherein $X^3$ is chlorine, a carboxylic acid of formula (6) wherein $X^3$ is hydroxyl, or an acid anhydride of formula (6) wherein $X^3$ is acyloxy. When an acid chloride is used as the esterifying agent, the reaction may be performed in a solventless system or in a solvent (e.g., methylene chloride, acetonitrile, toluene or hexane) by sequentially or simultaneously adding diol compound (5a) or (5b), a corresponding acid chloride (e.g., methacryloyl chloride), and a base (e.g., triethylamine, pyridine or 4-dimethylaminopyridine), and optionally cooling or heating the reaction system. When a carboxylic acid is used as the esterifying agent, the reaction may be performed in a solvent (e.g., toluene or hexane) by heating diol compound (5a) or (5b) and a corresponding carboxylic acid (e.g., methacrylic acid) in the presence of an acid catalyst, and optionally removing water formed by the reaction from the reaction system. Examples of the acid catalyst used herein include mineral acids such as hydrochloric acid, sulfuric acid, nitric acid and perchloric acid and organic acids such as p-toluenesulfonic acid and benzenesulfonic acid. When an acid anhydride is used as the esterifying agent, the reaction may be performed in a solventless system or in a solvent (e.g., methylene chloride, acetonitrile, toluene or hexane) by sequentially or simultaneously adding diol compound (5a) or (5b), a corresponding acid anhydride (e.g., methacrylic anhydride), and a base (e.g., triethylamine, pyridine or 4-dimethylaminopyridine), and optionally cooling or heating the reaction system. It is desirable from the standpoint of yield that the reaction time is determined so as to drive the reaction to completion by monitoring the reaction process by GC or silica gel TLC. Usually, the reaction time is about 0.5 to 24 hours. From the reaction mixture, the desired monomer (2a) or (2b) is recovered through an ordinary aqueous workup. If necessary, the monomer may be purified by a standard technique such as distillation, chromatography or recrystallization.

In addition to the recurring units having the formula (1a) and/or (1b), the polymer may further comprise recurring units having the formula (1c).

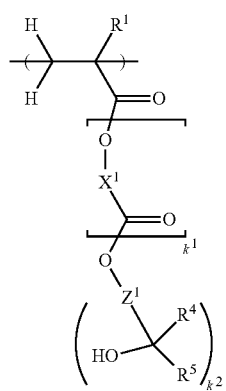

(1c)

Herein $R^1$ is hydrogen or methyl, $R^4$ and $R^5$ are each independently a straight, branched or cyclic $C_1$-$C_{10}$ monovalent hydrocarbon group, $R^4$ and $R^5$ may bond together to form an alicyclic group with the carbon atom to which they are attached, $X^1$ is a straight, branched or cyclic $C_1$-$C_{20}$ divalent hydrocarbon group in which any constituent —$CH_2$— moiety may be replaced by —O— or —C(=O)—, $Z^1$ is a straight, branched or cyclic $C_1$-$C_{20}$ tri- to pentavalent aliphatic hydrocarbon group in which any constituent —$CH_2$— moiety may be replaced by —O— or —C(=O)—, $k^1$ is 0 or 1, and $k^2$ is an integer of 2 to 4.

Typical of the straight, branched or cyclic $C_1$-$C_{10}$ monovalent hydrocarbon group represented by $R^4$ and $R^5$ are alkyl groups including methyl, ethyl, propyl, isopropyl, n-butyl, s-butyl, t-butyl, cyclopentyl, cyclohexyl, 2-ethylhexyl, n-octyl, norbornyl, tricyclodecanyl, and adamantyl.

Examples of the straight, branched or cyclic $C_1$-$C_{20}$ divalent hydrocarbon group represented by $X^1$ are given below, but not limited thereto.

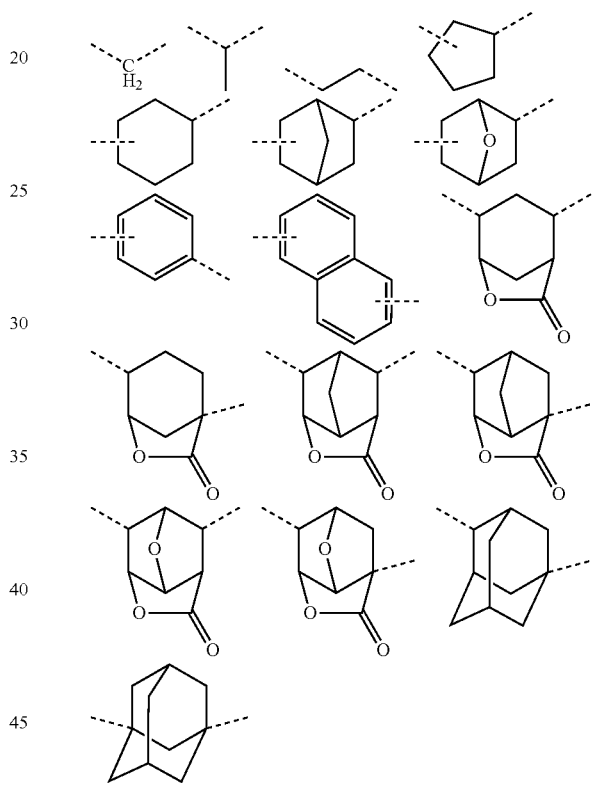

Examples of the straight, branched or cyclic $C_1$-$C_{20}$ tri- to pentavalent aliphatic hydrocarbon group of $Z^1$ are given below, but not limited thereto.

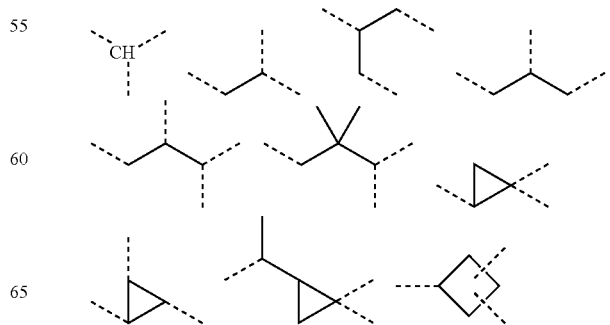

-continued

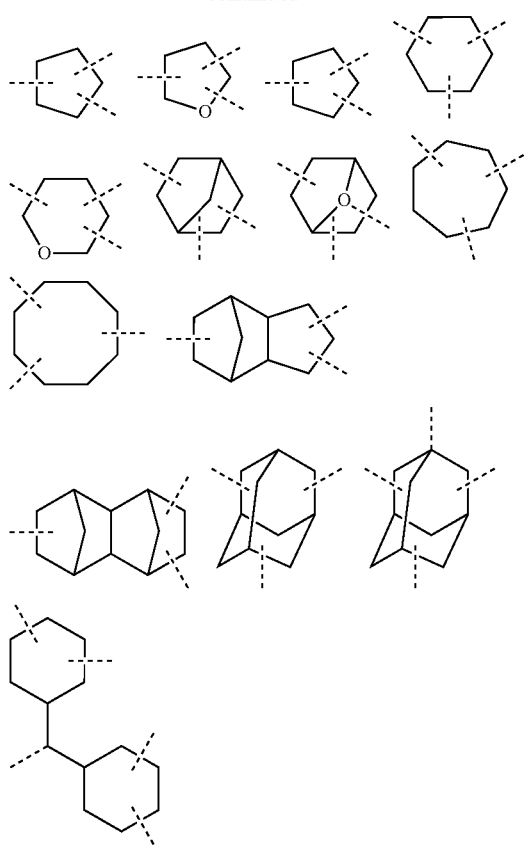
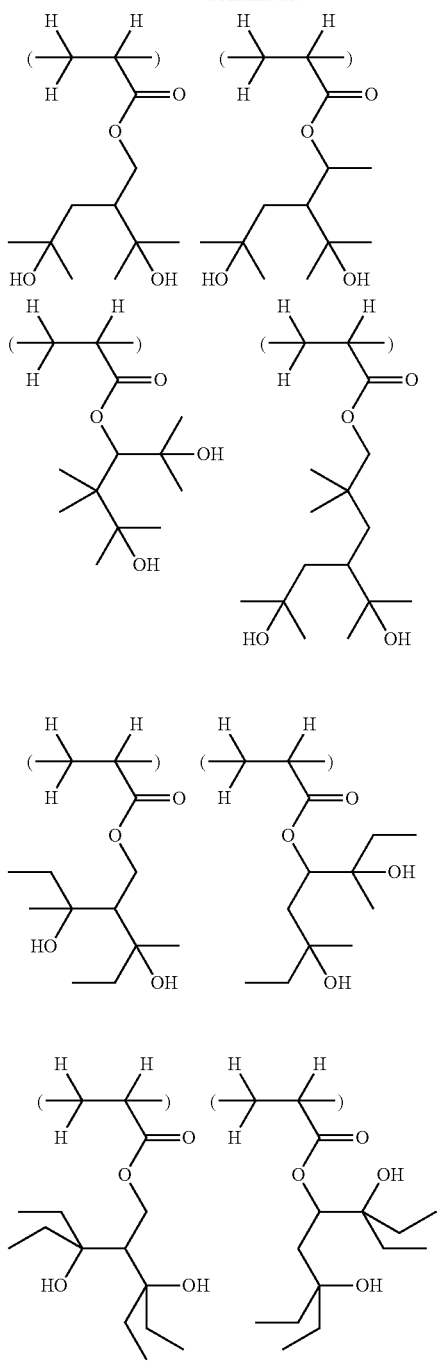

When the recurring units having formula (1c) are copolymerized with the recurring units having formula (1a) and/or (1b), the dissolution rate of the unexposed region in alkaline developer may be further improved. Like the units of formulae (1a) and (1b), the unit of formula (1c) has two to four tertiary alcoholic hydroxyl groups which are acid labile groups. Prior to exposure, the polymer has a high affinity to and high solubility in alkaline developer by virtue of a plurality of highly polar, hydrophilic groups thereon. After exposure, a plurality of hydroxyl groups are lost in the exposed region of resist film, indicating a substantial drop of solubility in alkaline developer, that is, the exposed region becoming insolubilized in the developer.

Examples of suitable recurring units having formula (1c) are shown below, but not limited thereto.

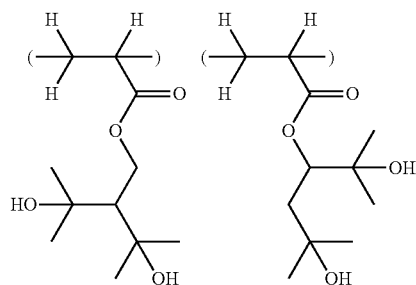
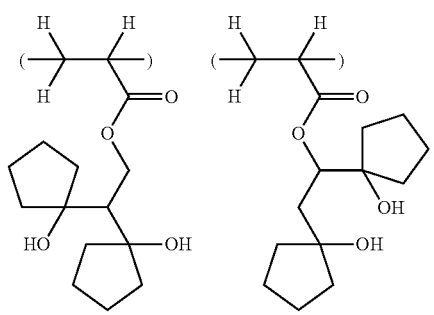

-continued
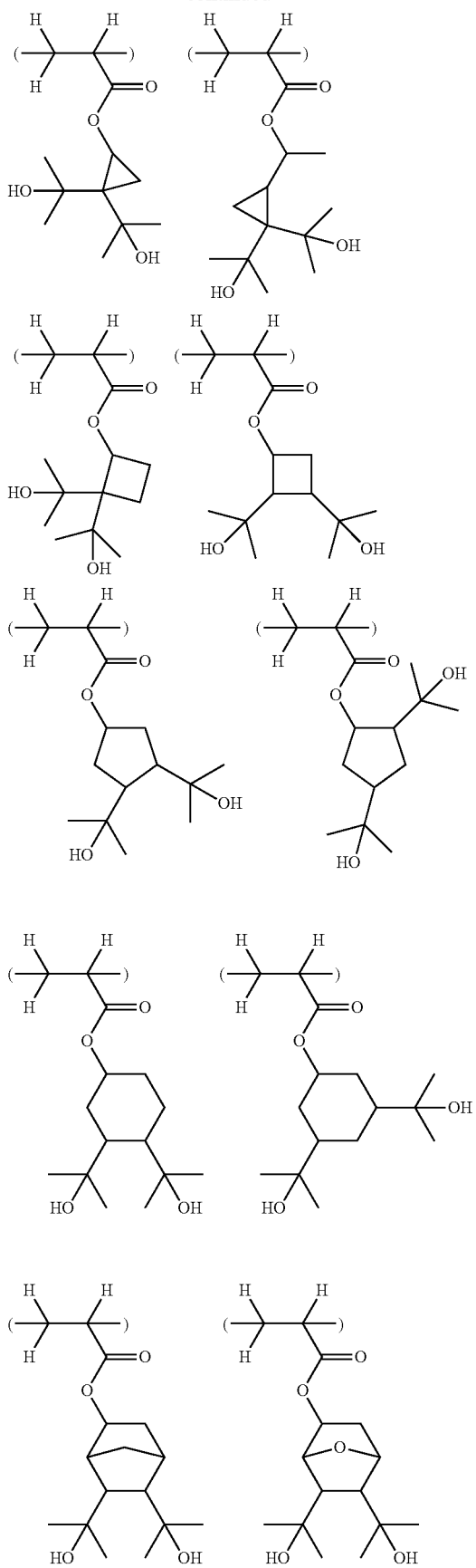
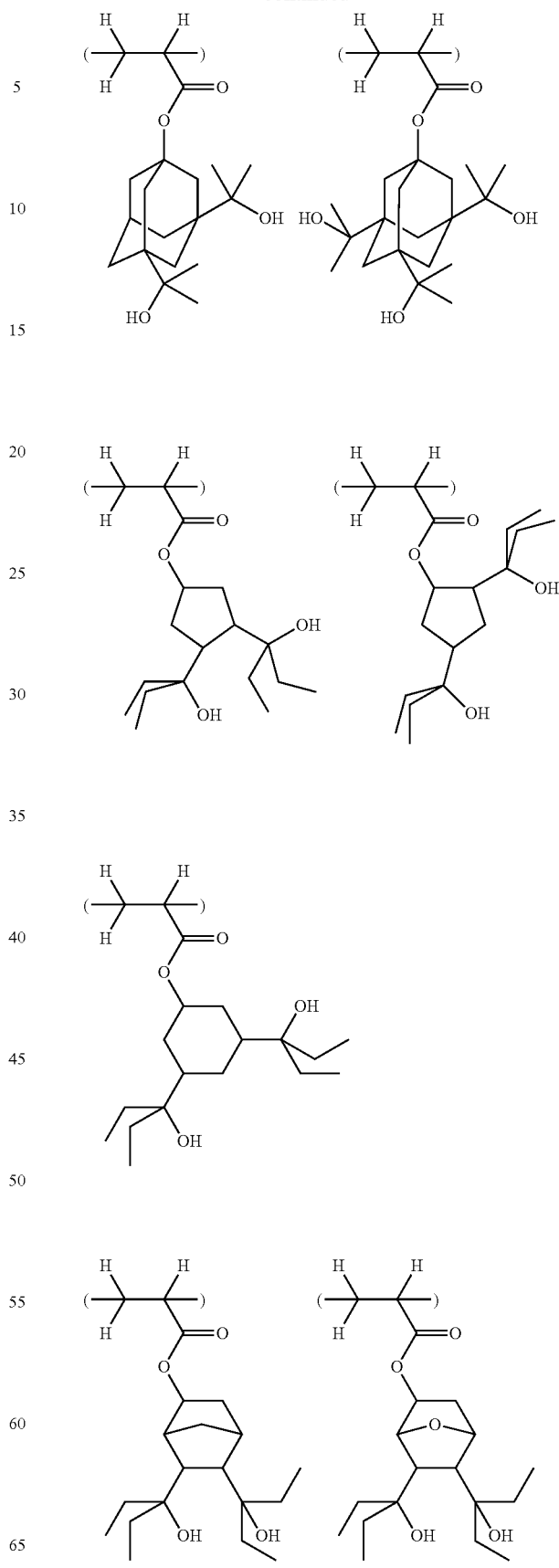

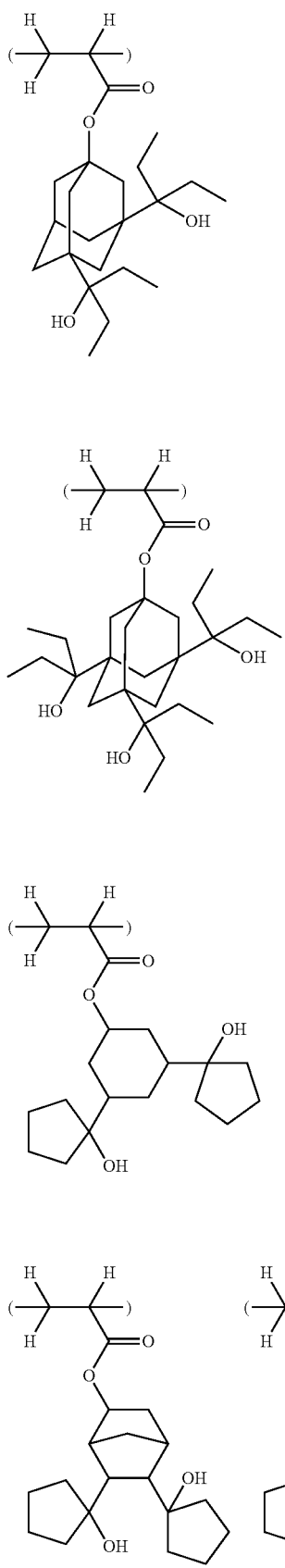
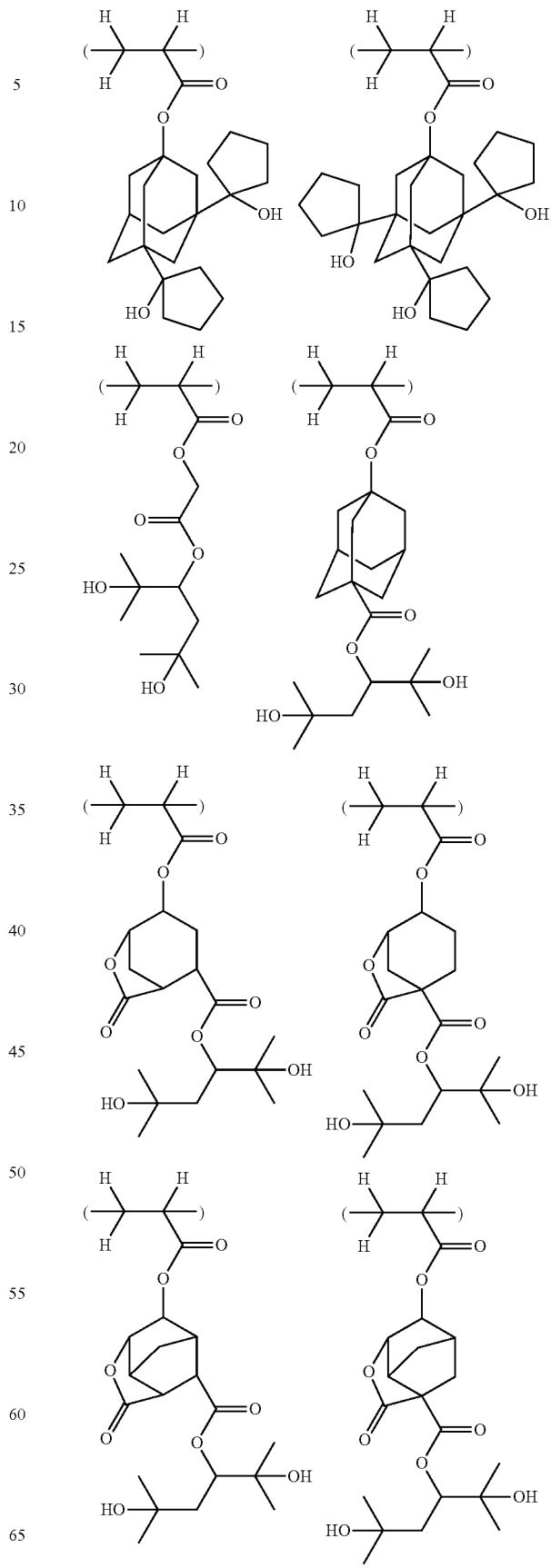

39
-continued
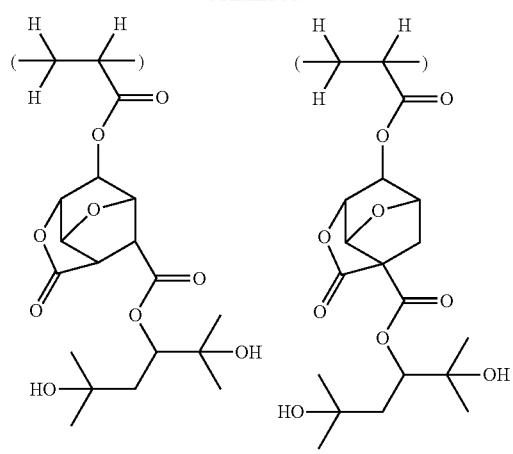
40
-continued
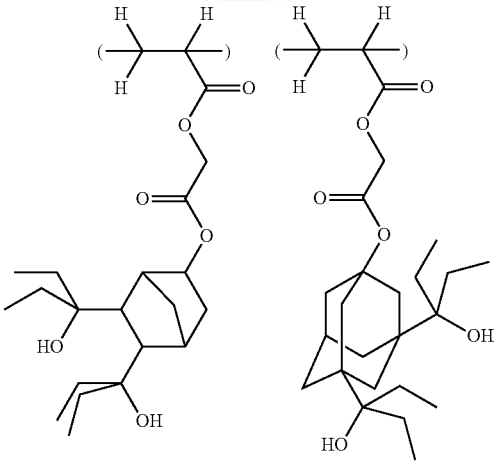

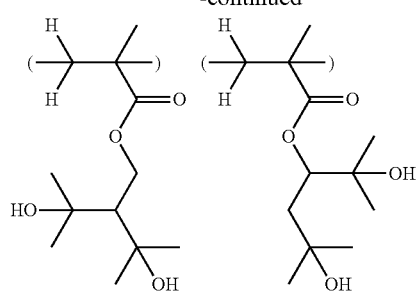
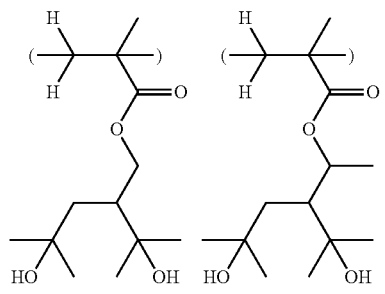
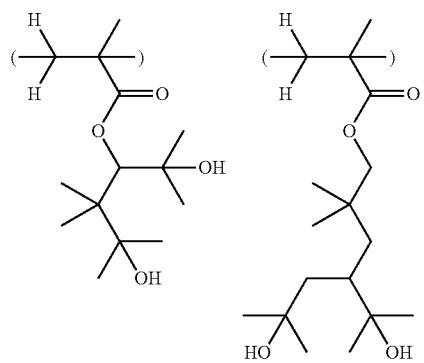
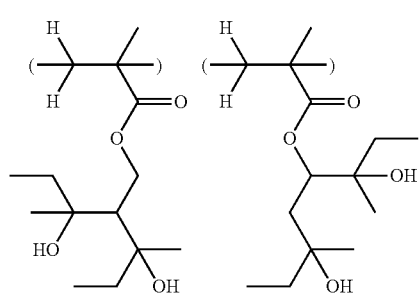
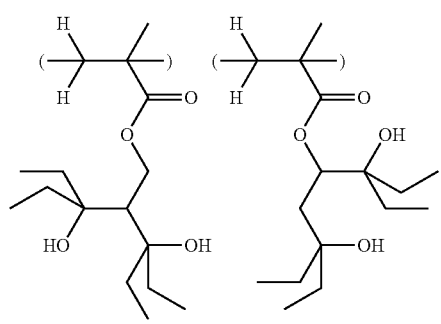
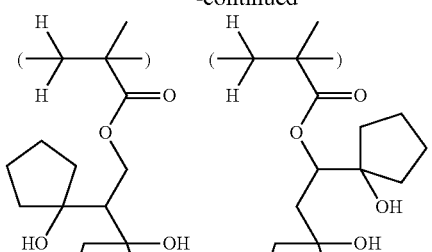
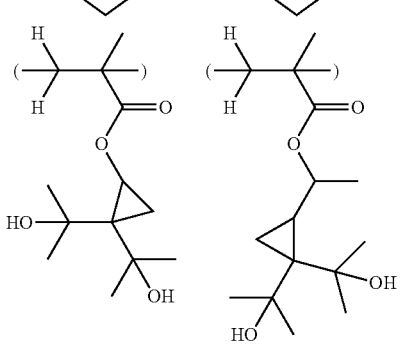
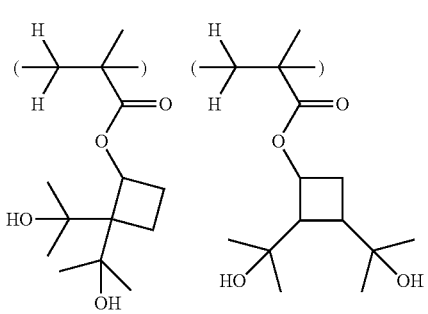
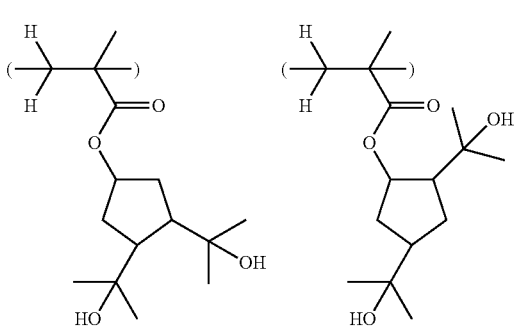
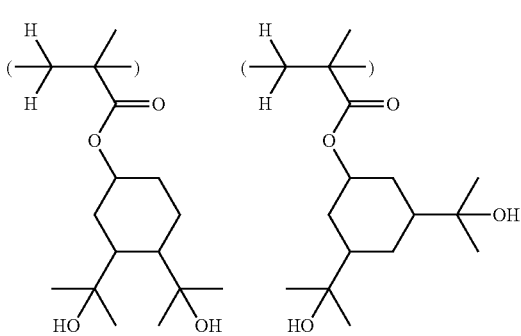

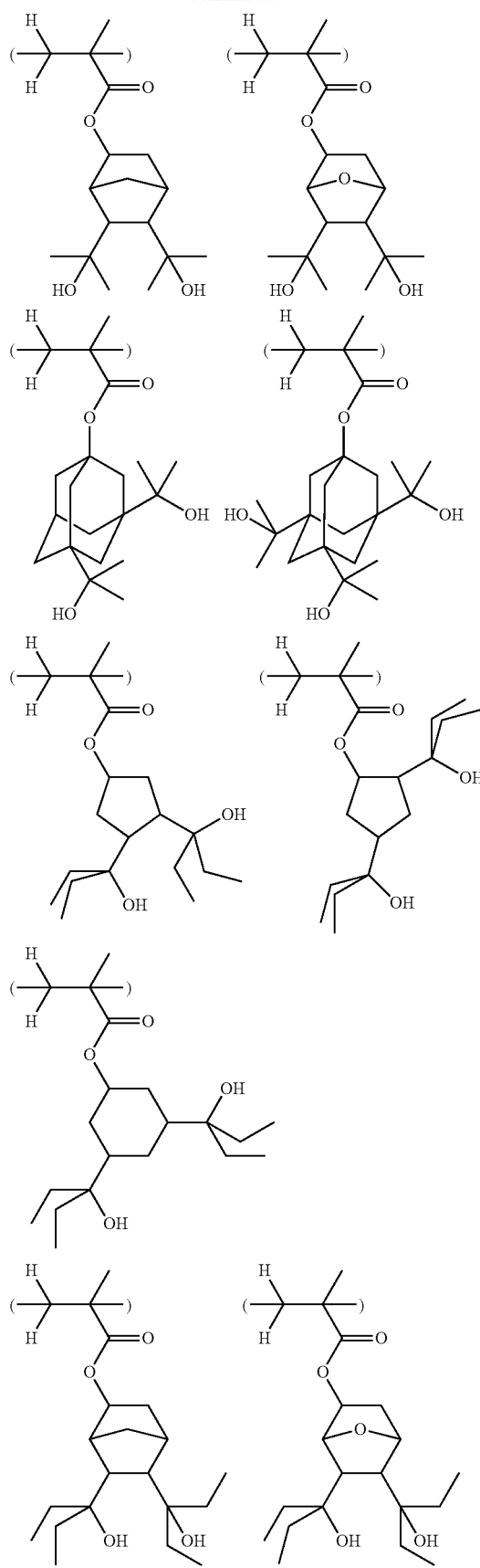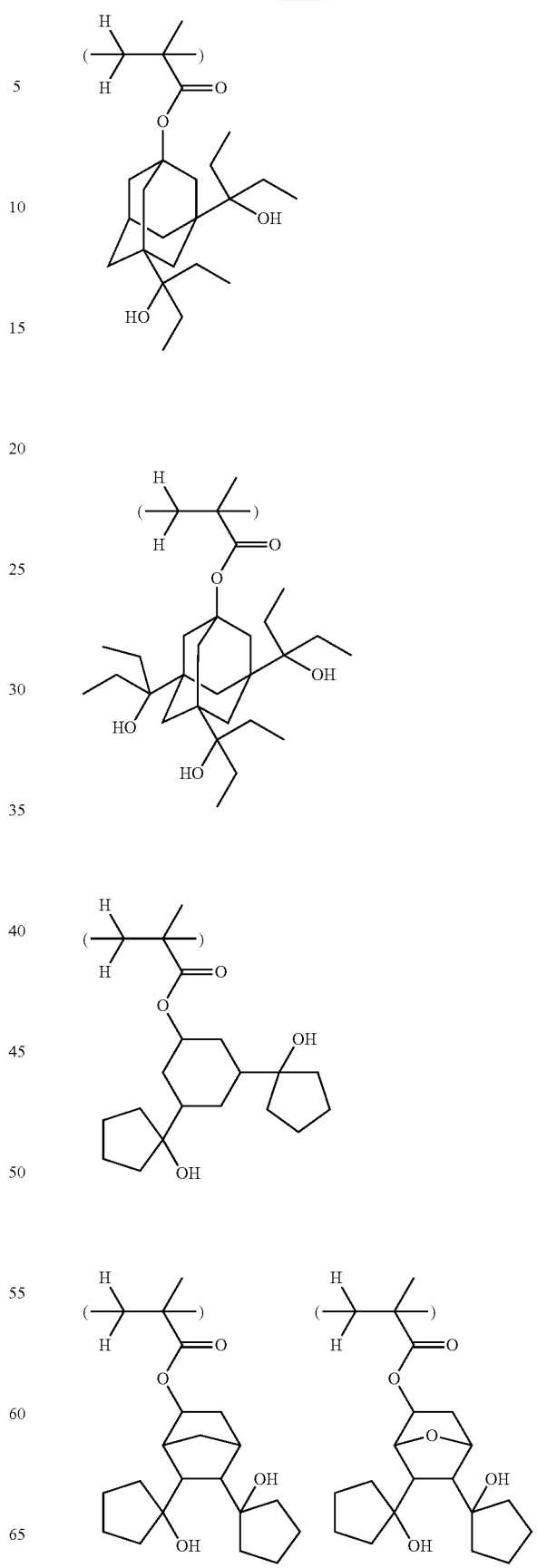

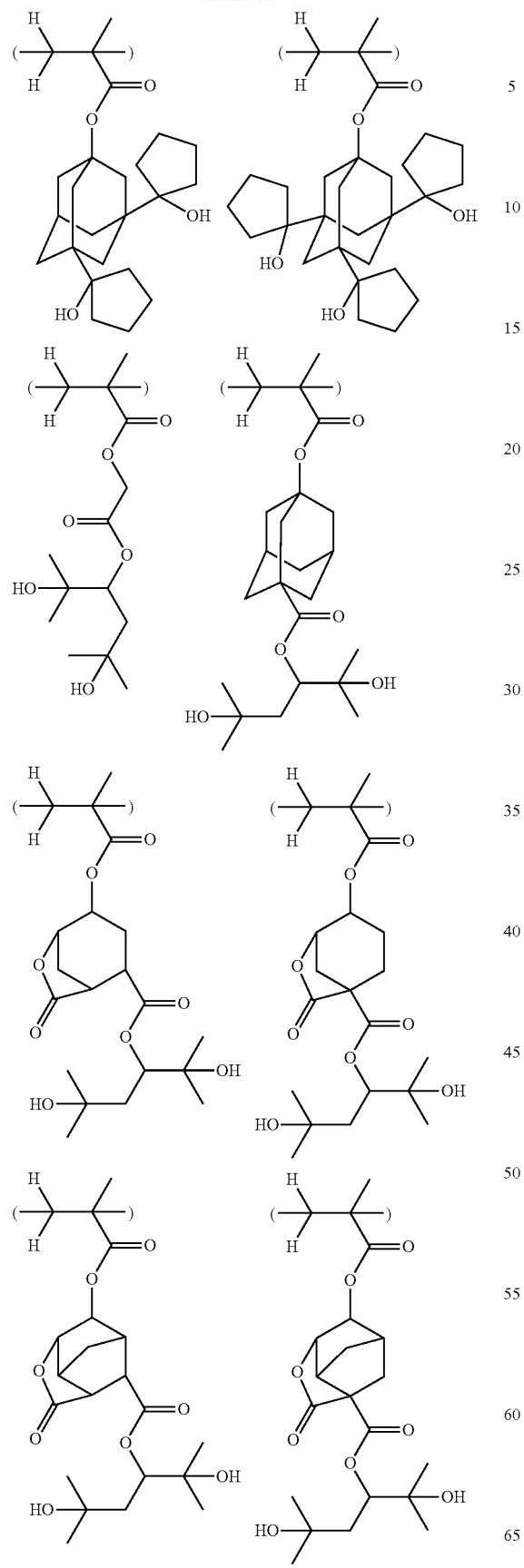
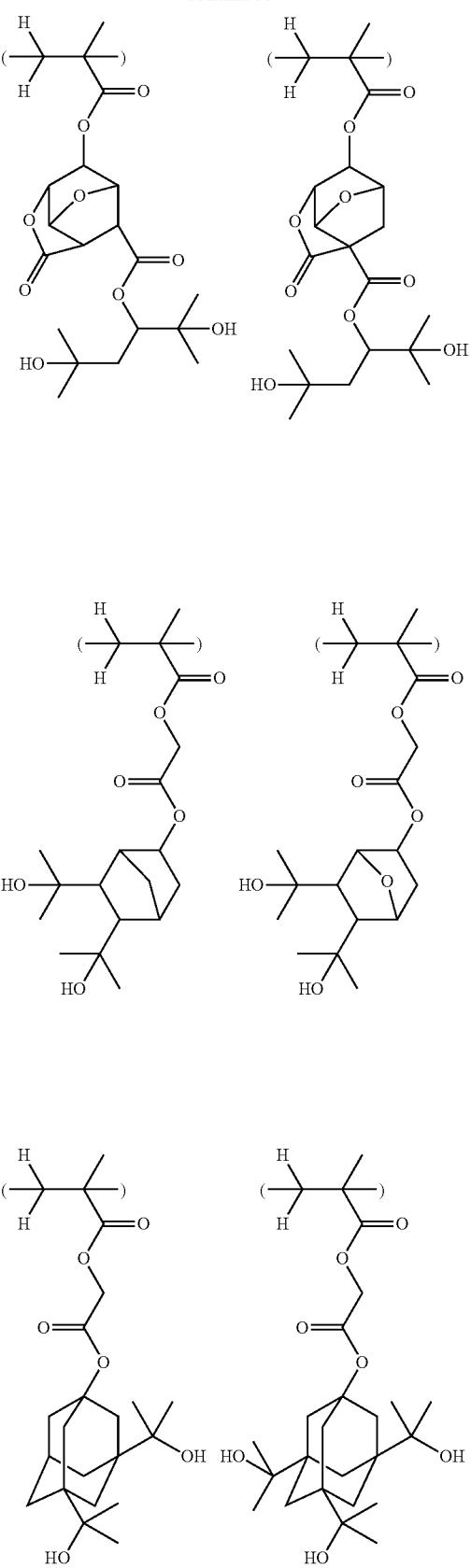

-continued

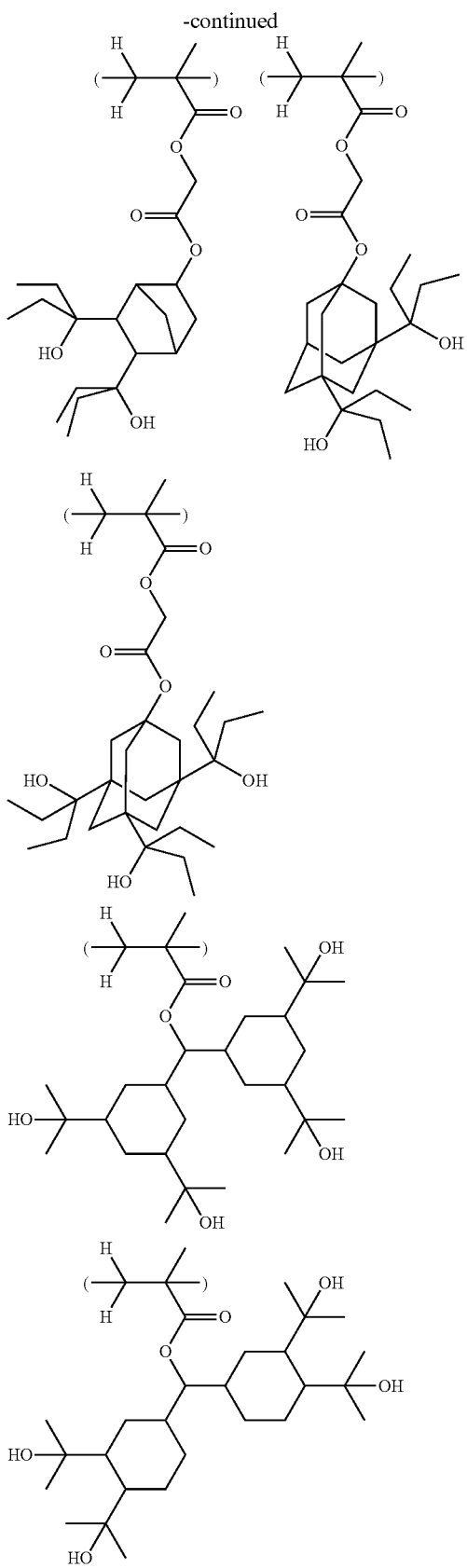

In addition to the recurring units of formula (1a) and/or (1b), the inventive polymer may further comprise recurring units of at least one type selected from recurring units having formulae (A) to (D) for the purpose of solubility control.

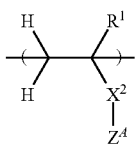

(A)

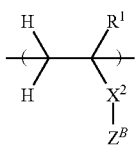

(B)

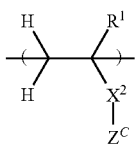

(C)

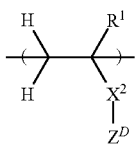

(D)

Herein $R^1$ is hydrogen or methyl. $Z^A$ is a $C_1$-$C_{20}$ fluoroalcohol-containing group. $Z^B$ is a $C_1$-$C_{20}$ phenolic hydroxyl-containing group. $Z^C$ is a $C_1$-$C_{20}$ carboxyl-containing group. $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety. $X^2$ is a single bond, methylene, ethylene, phenylene, fluorinated phenylene, naphthylene, —O—$R^{01}$—, or —C(=O)—$Z^2$—$R^{01}$—, wherein $Z^2$ is oxygen or NH, and $R^{01}$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

The recurring unit of formula (A) has a fluoroalcohol-containing group having high affinity to alkaline aqueous solution. Preferred examples of the fluoroalcohol-containing unit include recurring units having a 1,1,1,3,3,3-hexafluoro-2-propanol residue and 2-hydroxy-2-trifluoromethyloxolane structure, as described in JP-A 2007-297590, JP-A 2008-111103, JP-A 2008-122932, and JP-A 2012-128067. Although these units have a tertiary alcoholic hydroxyl group or hemiacetal structure, they are not reactive with acid because of fluorine substitution.

Since the recurring units of formulae (A) to (C) are structural units having hydroxyl group's proton with a high acidity, the polymer becomes higher in alkaline solubility as the proportion of these units incorporated is increased. On the other hand, excessive incorporation of these units can adversely affect a polarity switch (or alkali insolubilizing effect) that is brought about by dehydration reaction taking place in recurring unit of formula (1a) or (1b) by acid. Accordingly, the recurring units of formulae (A) to (C) are preferably incorporated in such proportions that the alkali solubility of the unexposed region may be supplemented and the alkali insolubilizing effect of the exposed region not be impaired.

Illustrative, non-limiting examples of the recurring unit having formula (A) are shown below.
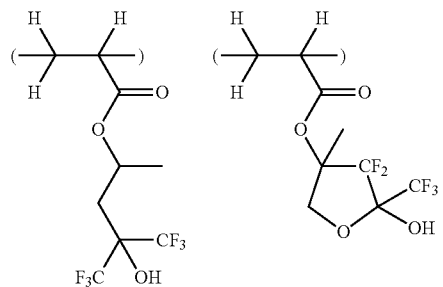
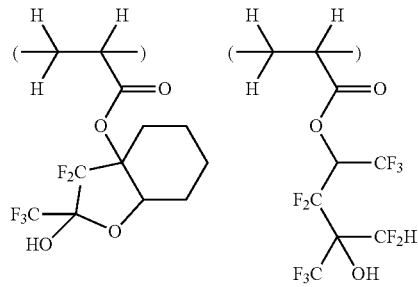
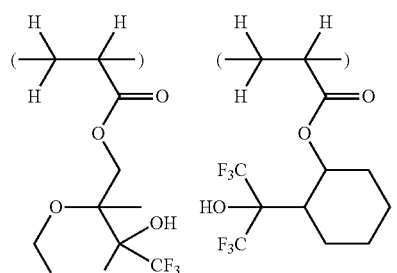
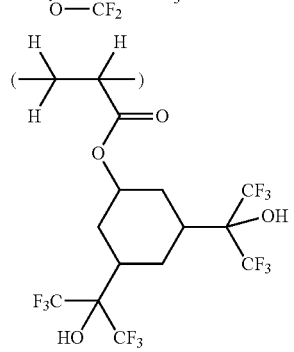
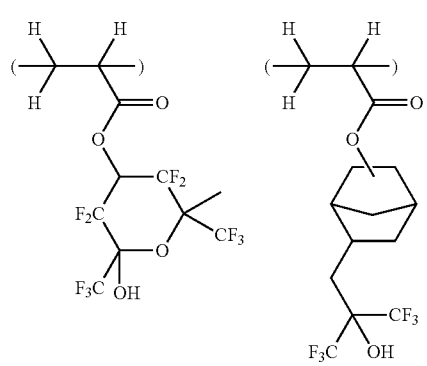
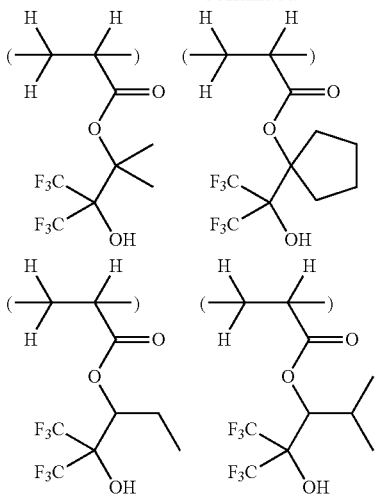
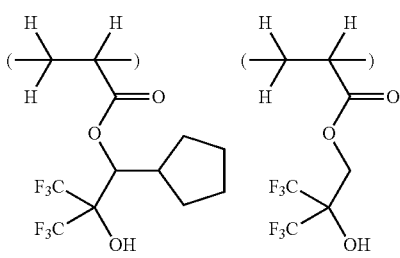
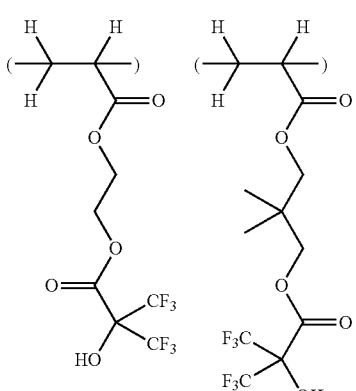
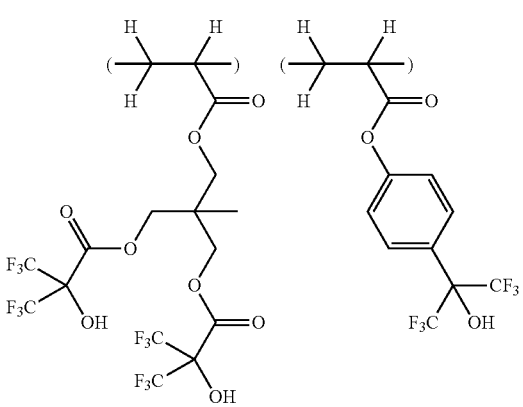

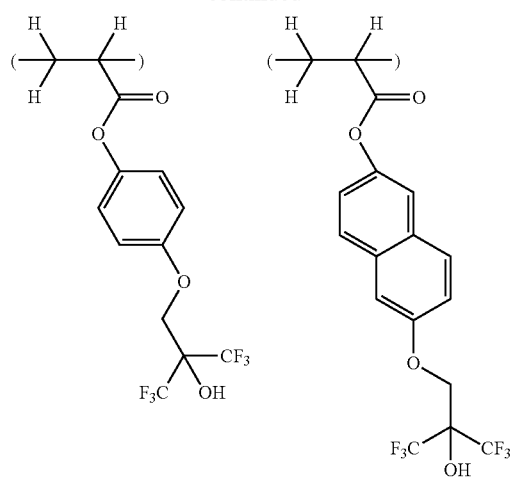
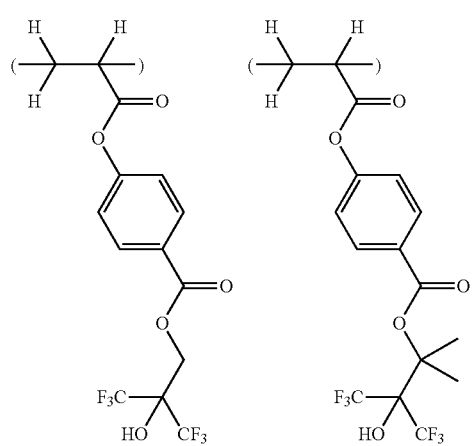
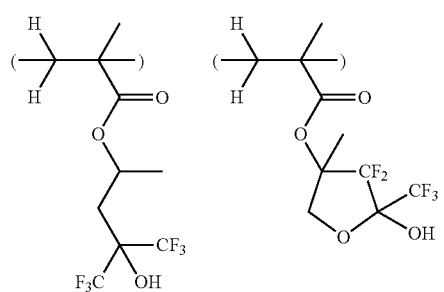
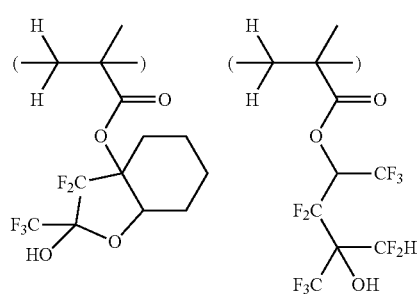
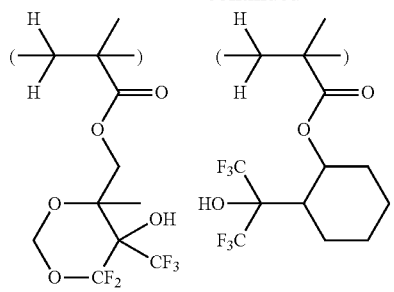
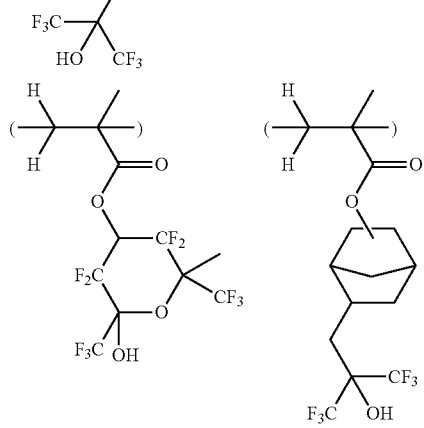
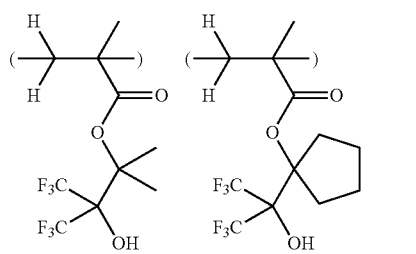
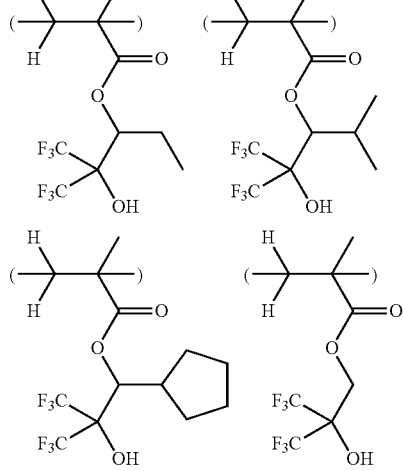

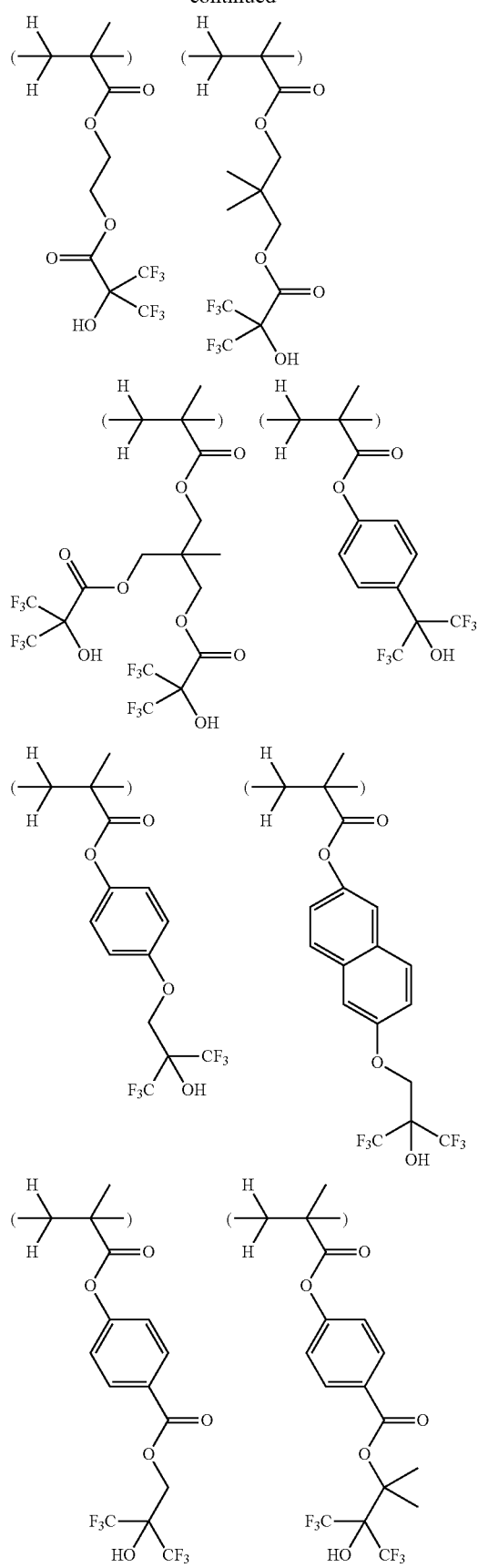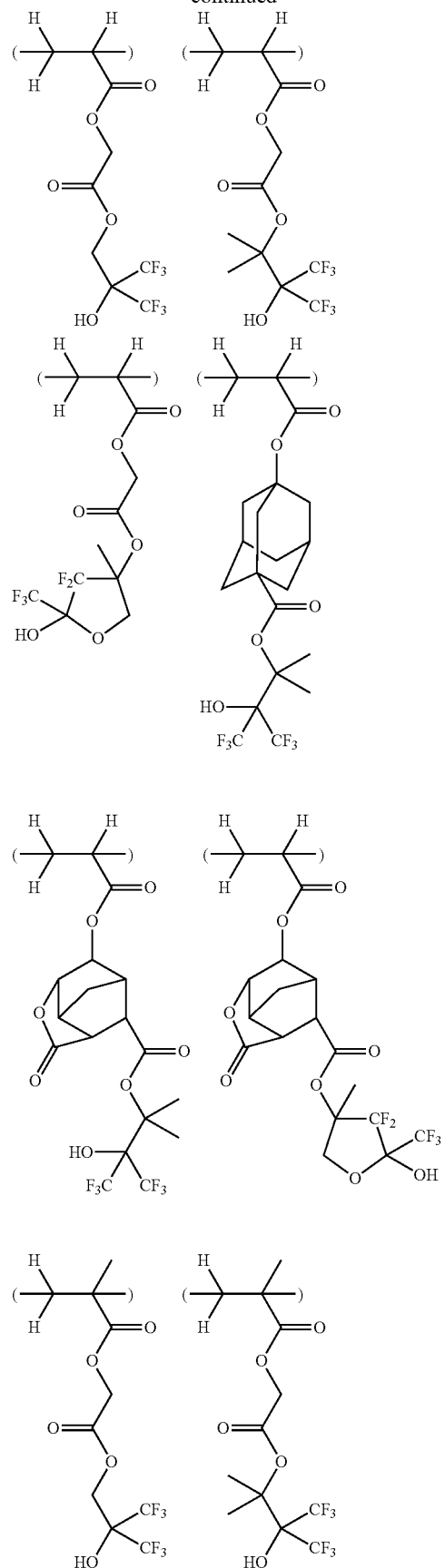

-continued
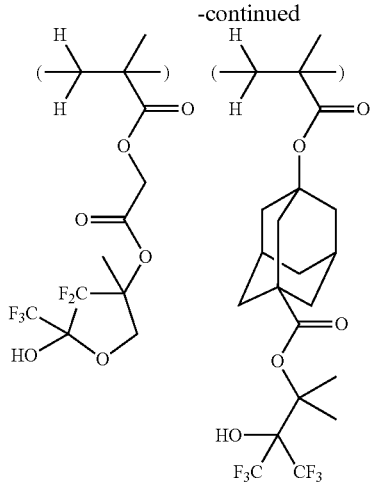
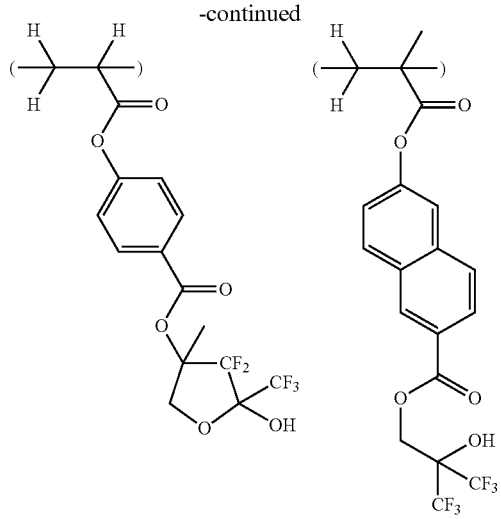
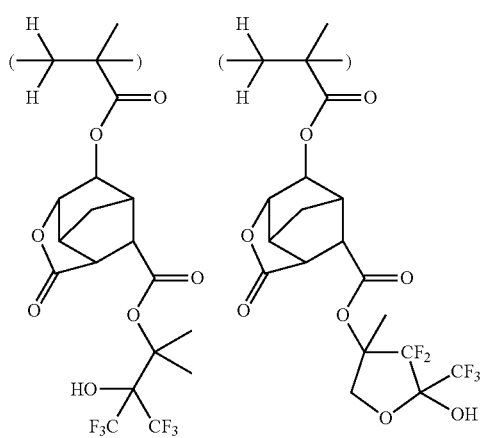
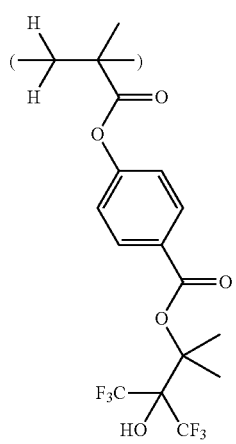
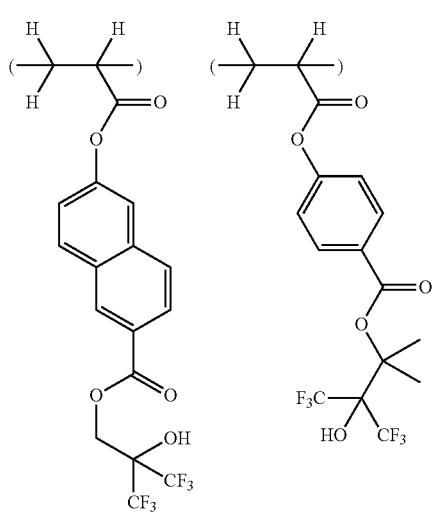
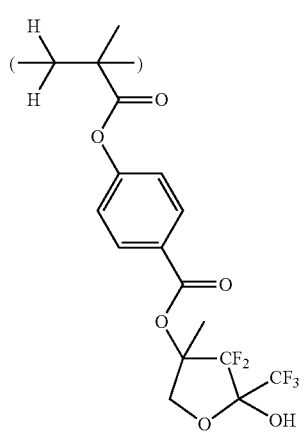
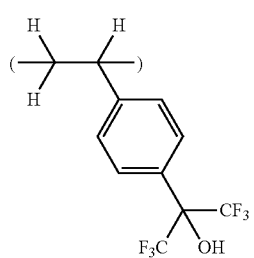

-continued
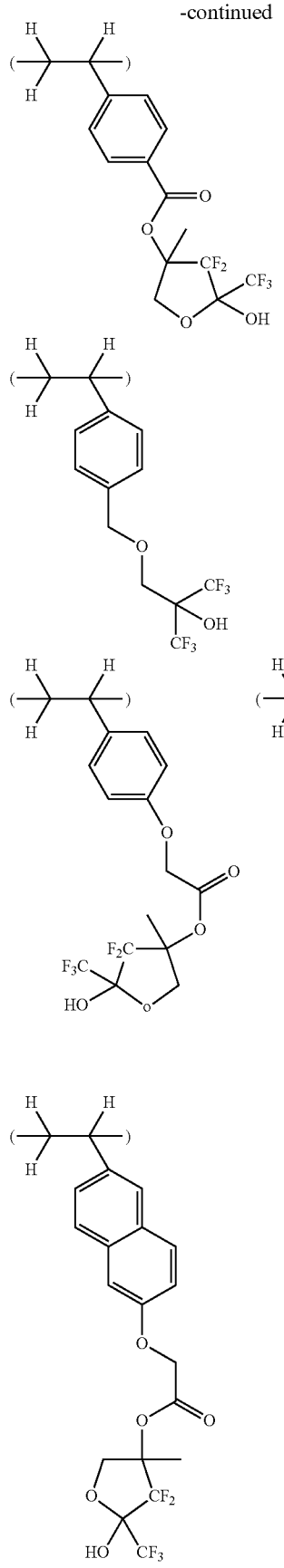
Illustrative, non-limiting examples of the recurring unit having formula (B) are shown below.
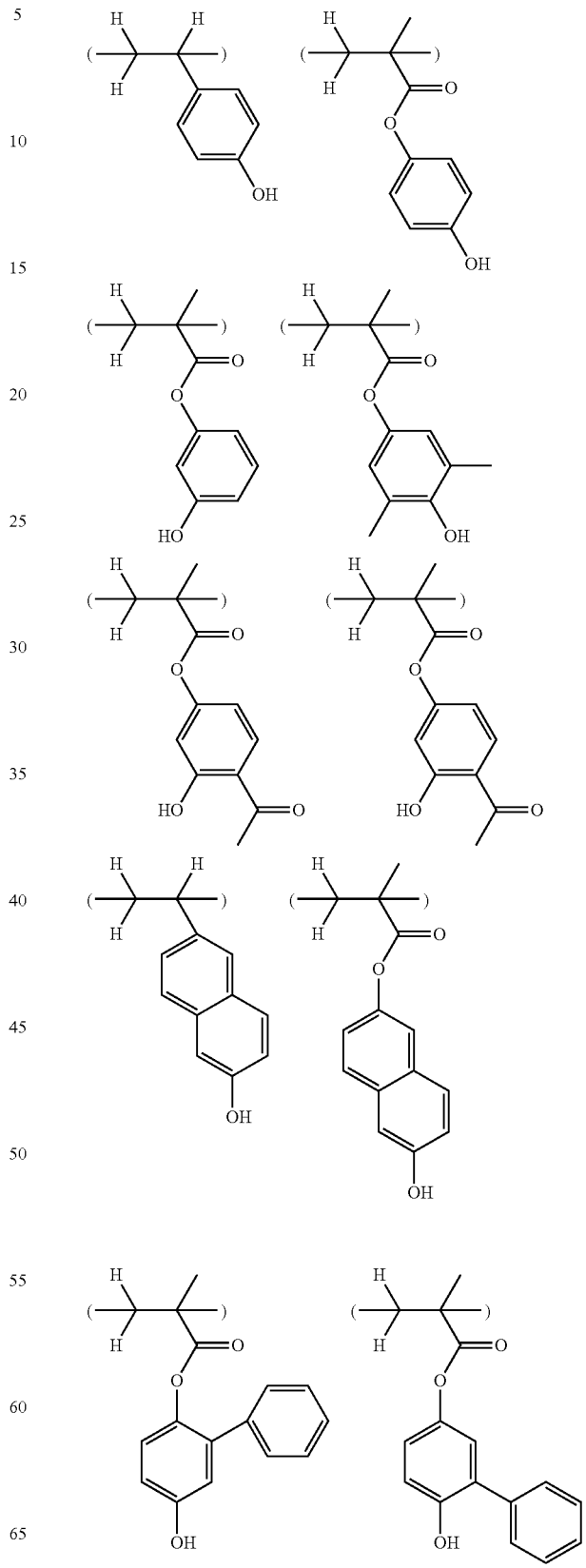

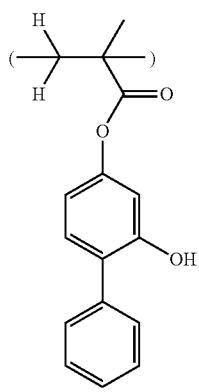

Illustrative, non-limiting examples of the recurring unit having formula (C) are shown below.

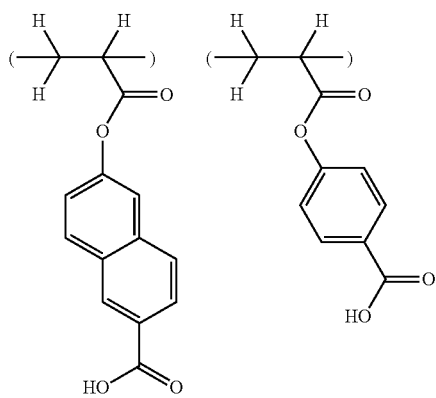

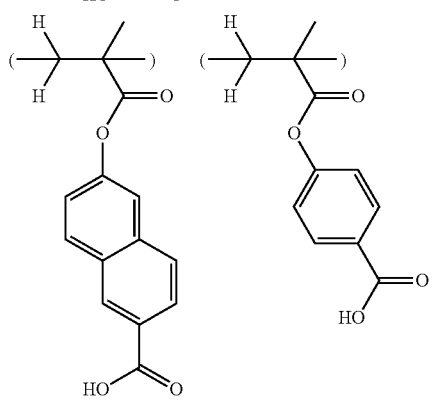

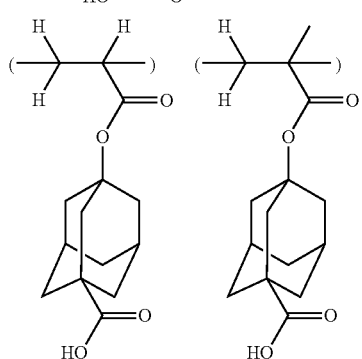

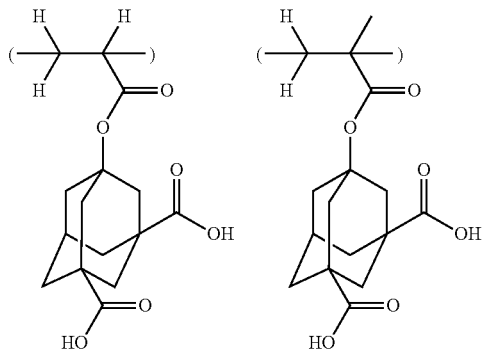

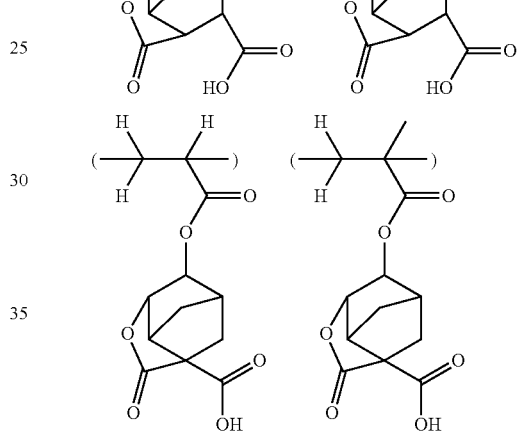

It is possible that the fluoroalcohol is protected with an acyl group or acid labile group in the polymer, so that the fluoroalcohol-containing unit corresponding to formula (A) may be generated by hydrolysis in alkaline developer or deprotection with the acid generated after exposure. Suitable such recurring units include the units described in JP-A 2012-128067 (U.S. Pat. No. 8,916,331), specifically units in paragraphs [0036]-[0040] and units (2a), (2b) and (2f) in paragraph [0041].

Illustrative, non-limiting examples of the recurring unit having formula (D) are shown below.

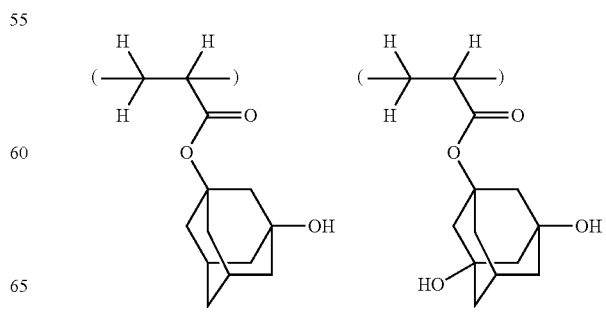

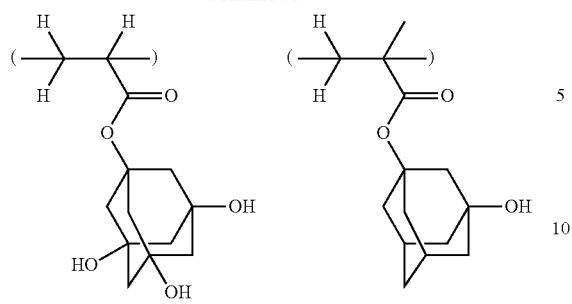
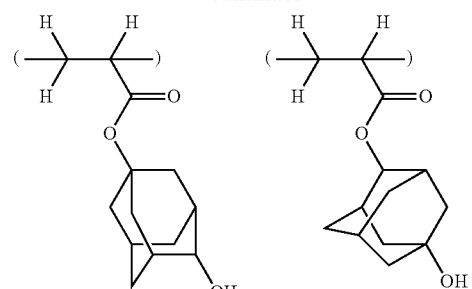
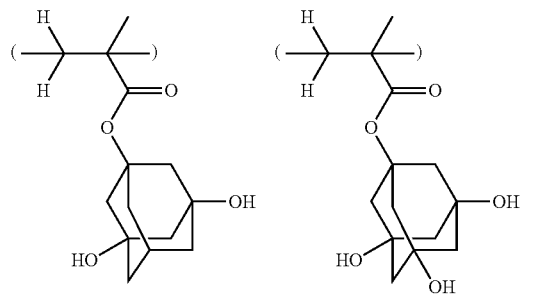
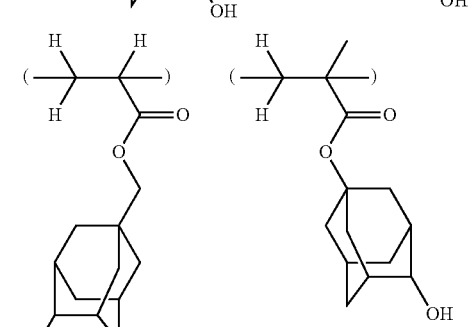
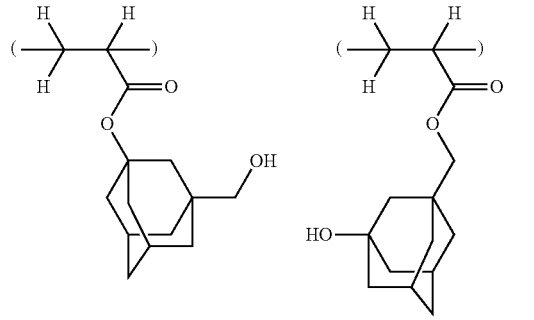
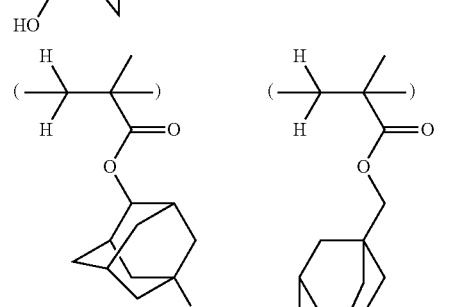
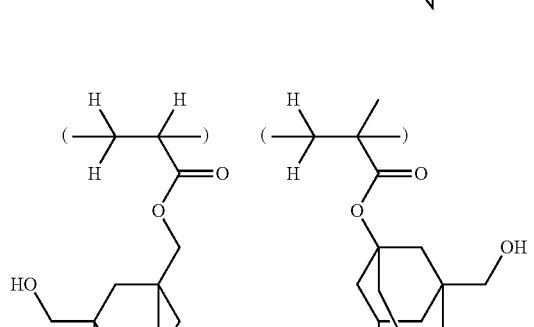
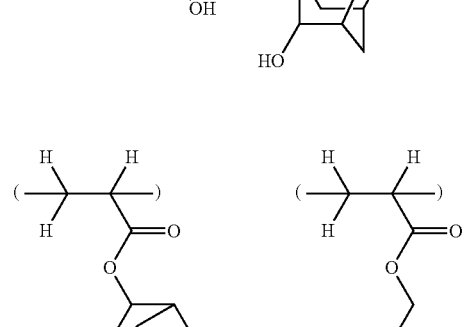
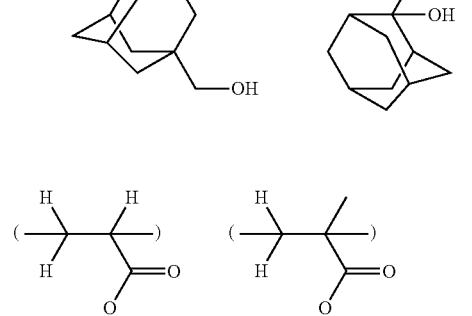
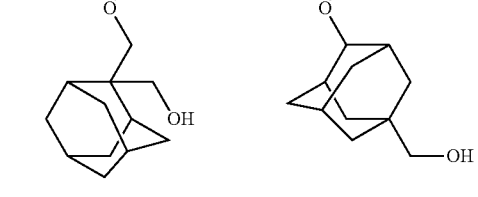

63
-continued
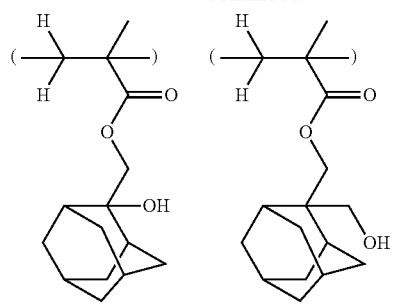
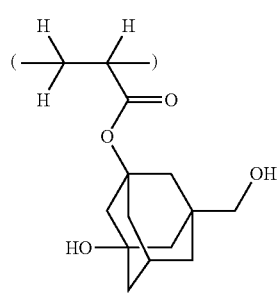
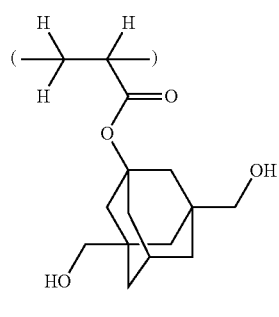
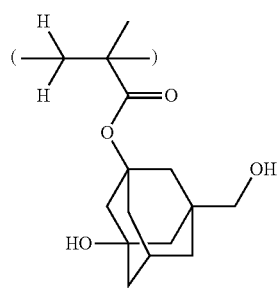
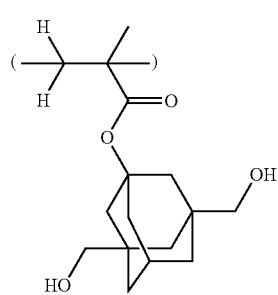
64
-continued
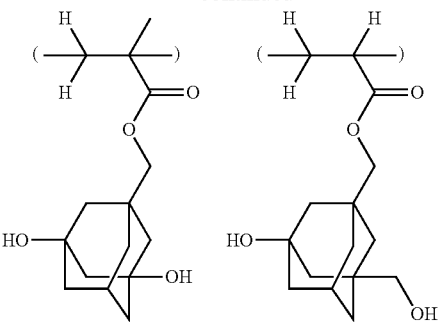
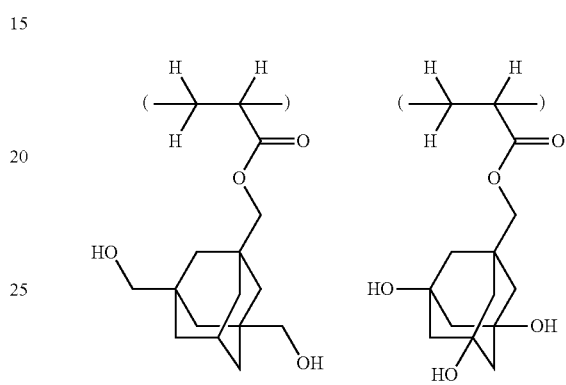
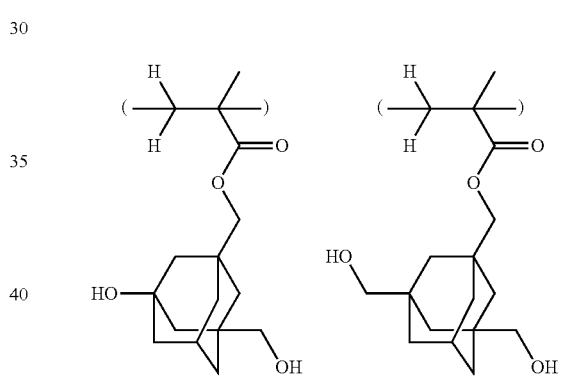
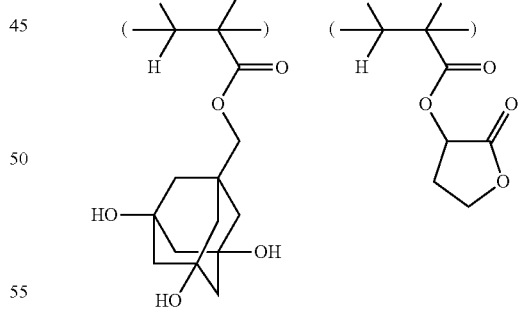
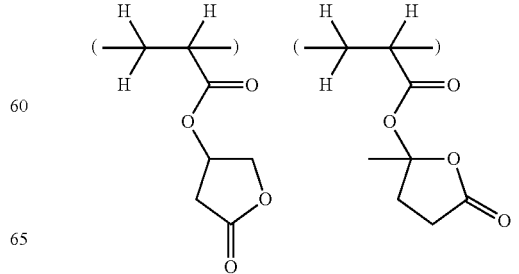

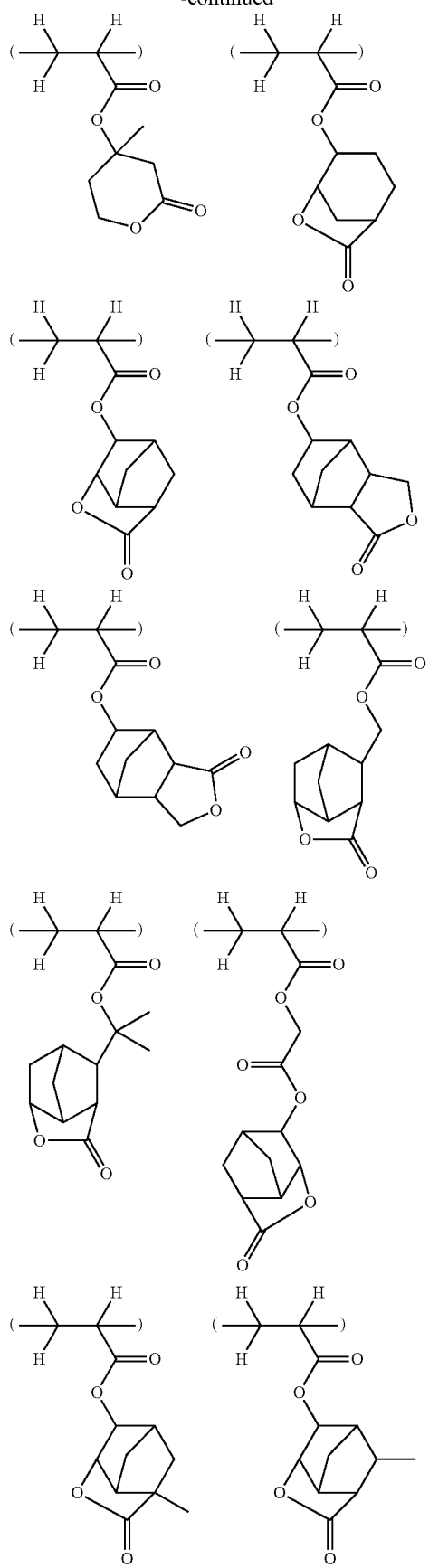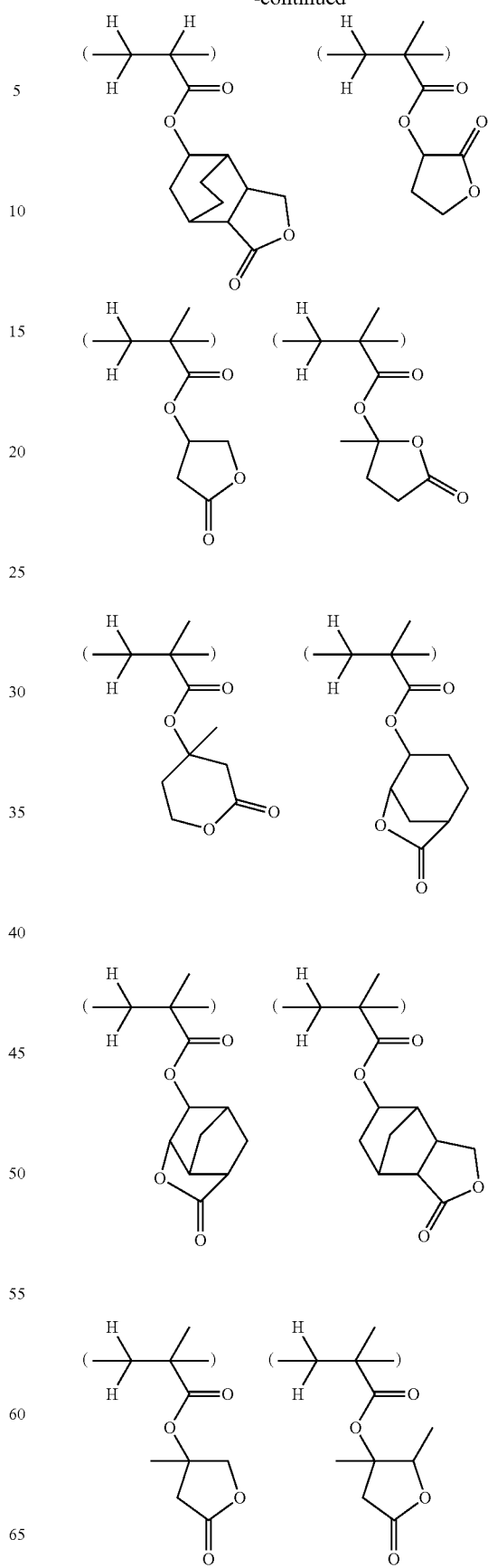

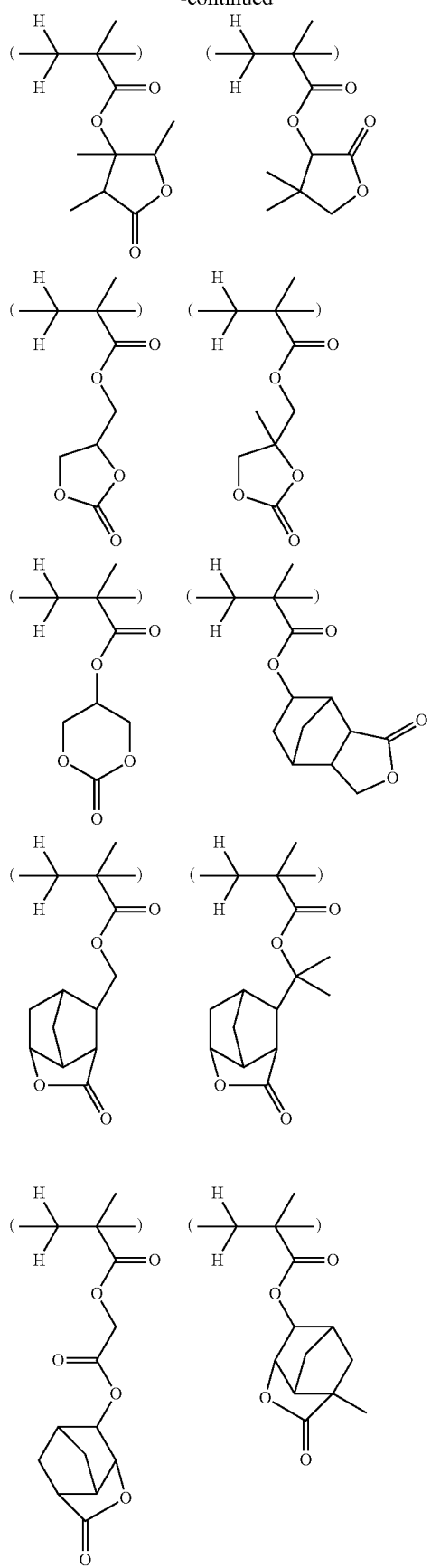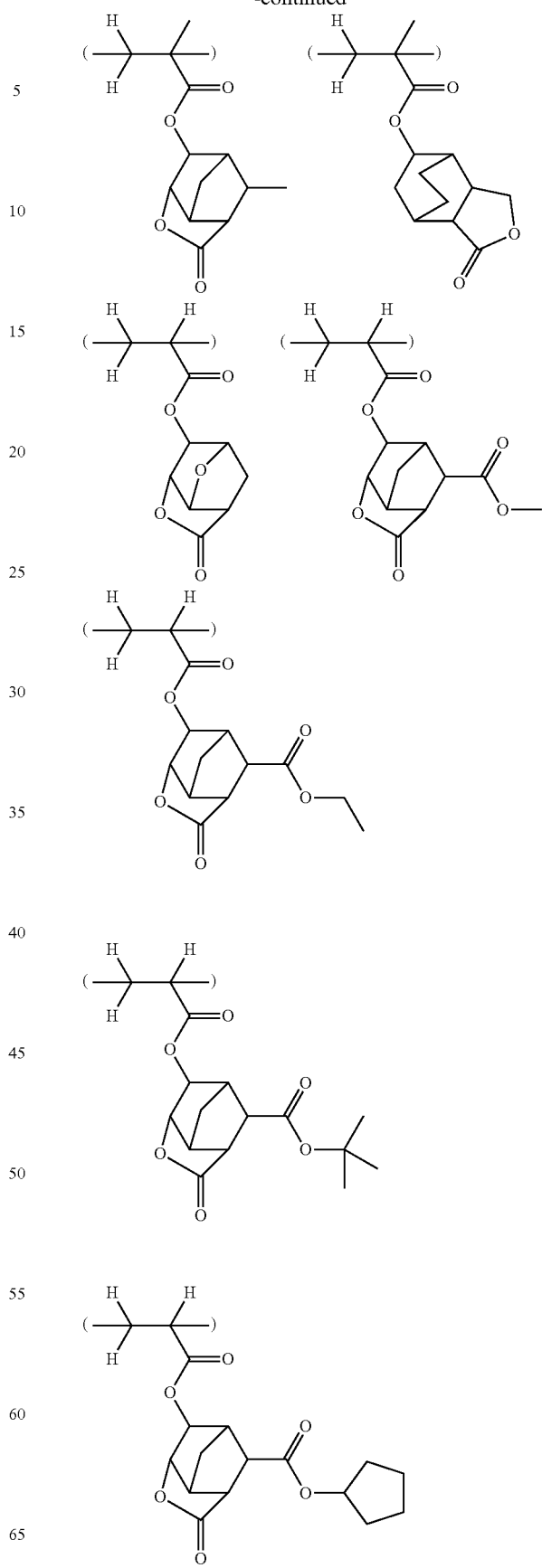

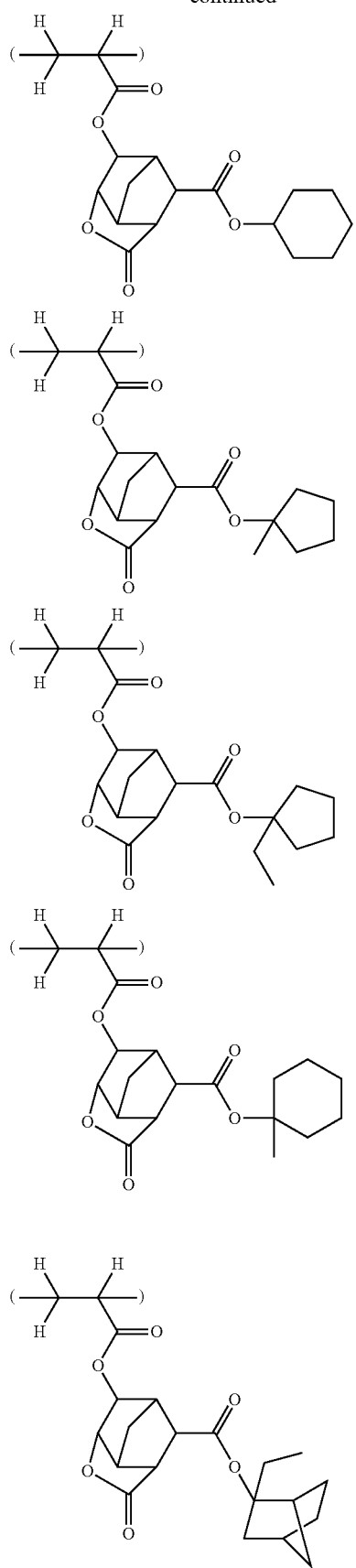
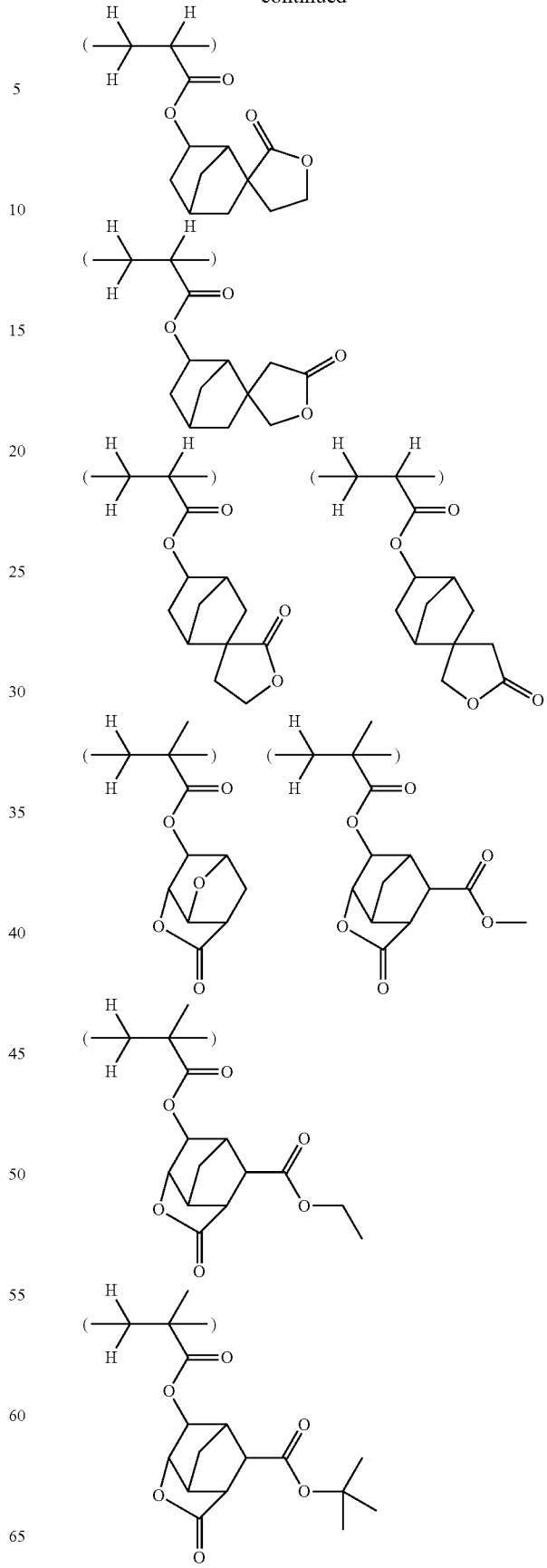

71
-continued
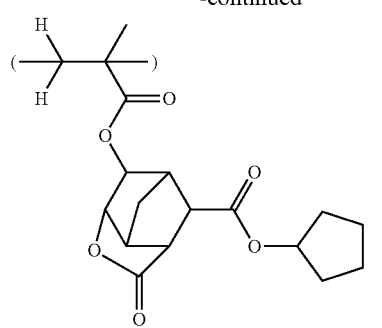
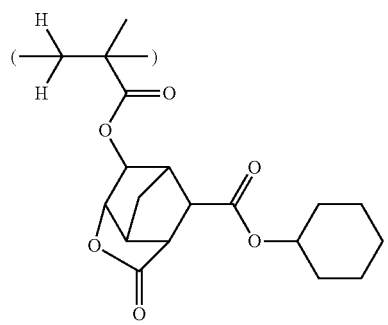
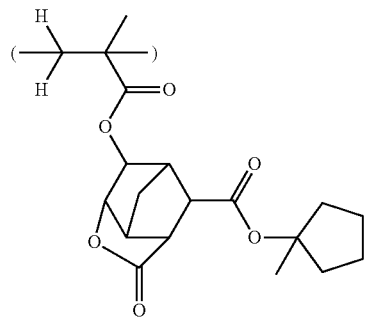
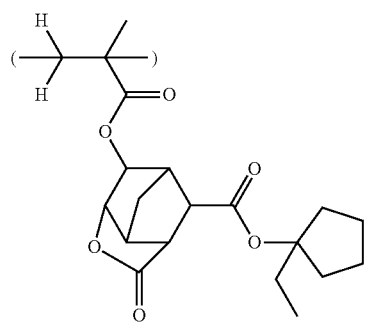
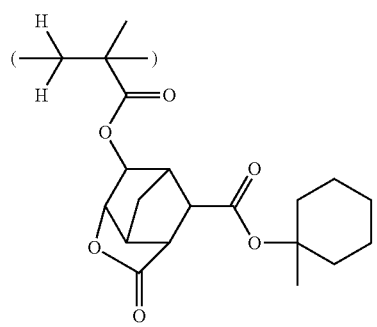
72
-continued
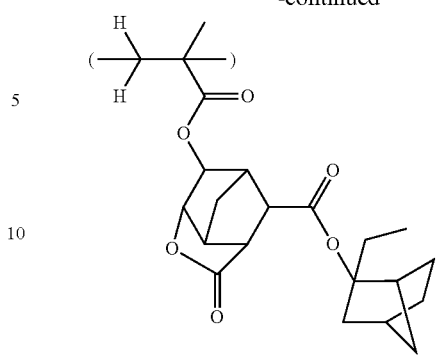
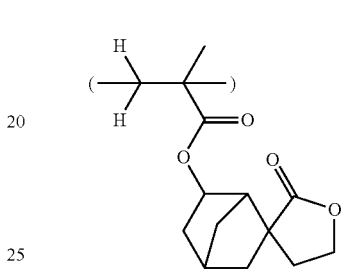
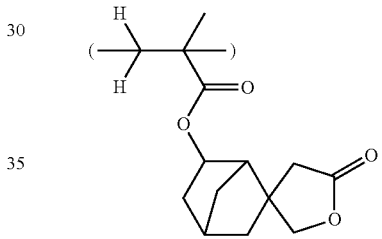
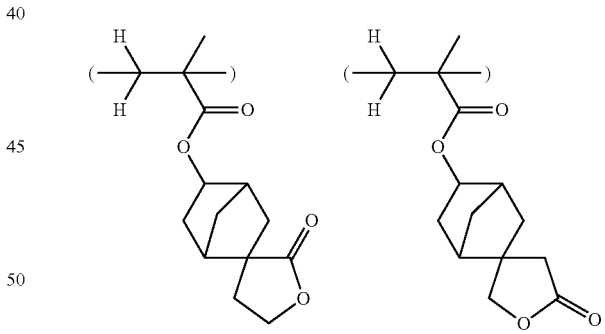
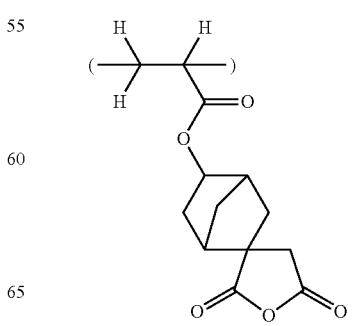

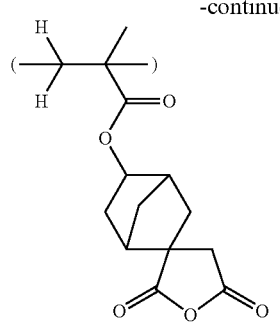
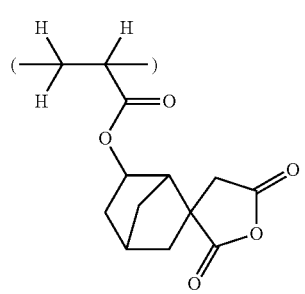
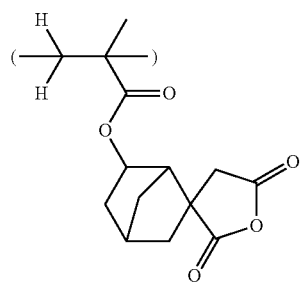
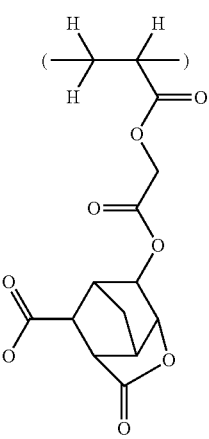
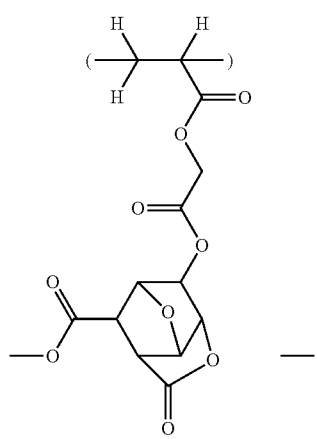
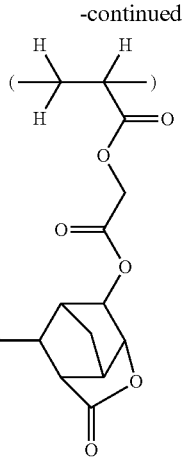
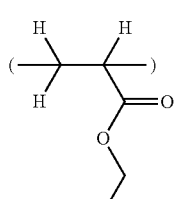
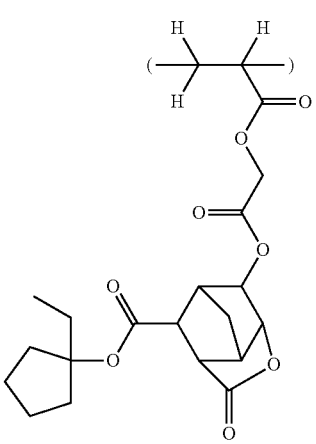
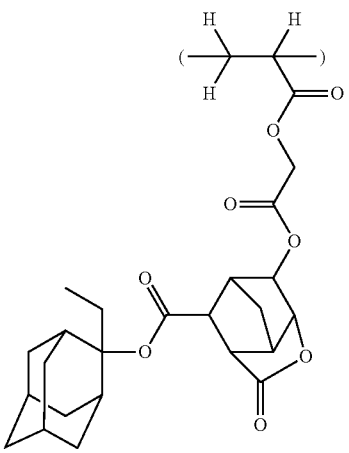

75
-continued
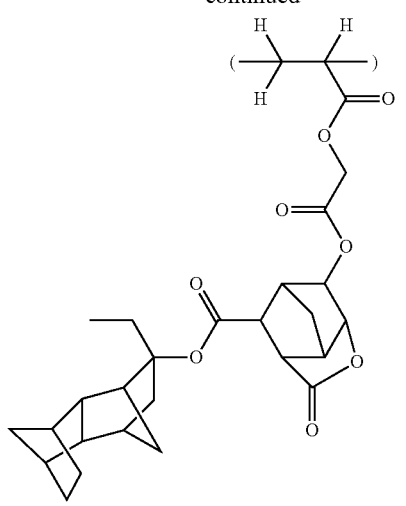
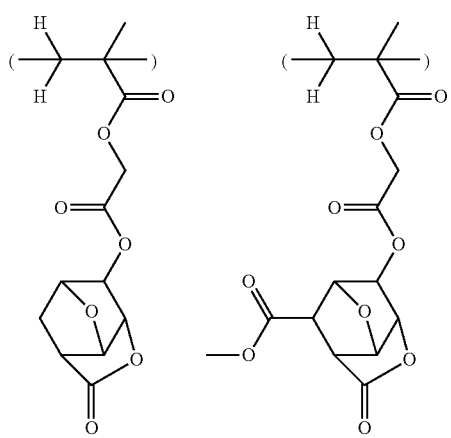
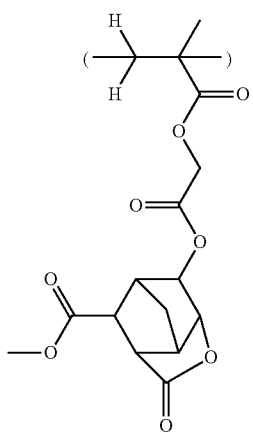
76
-continued
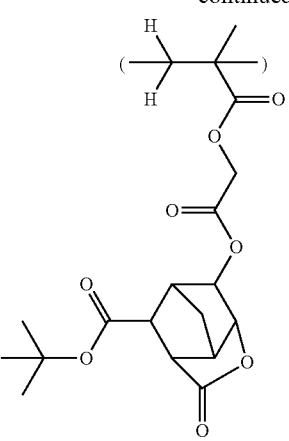
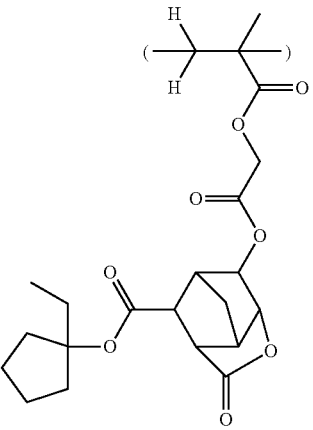
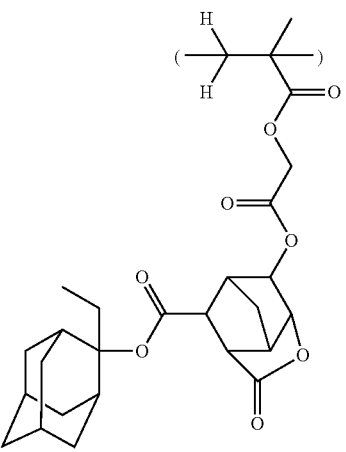

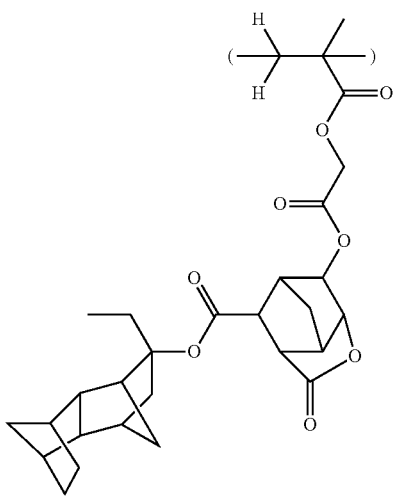
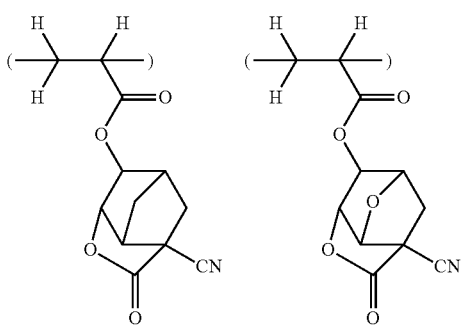
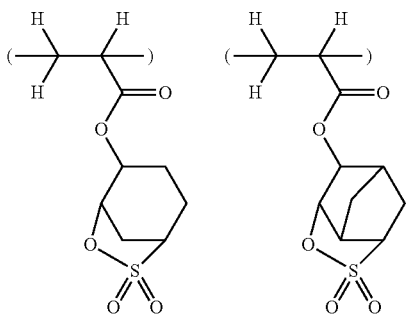
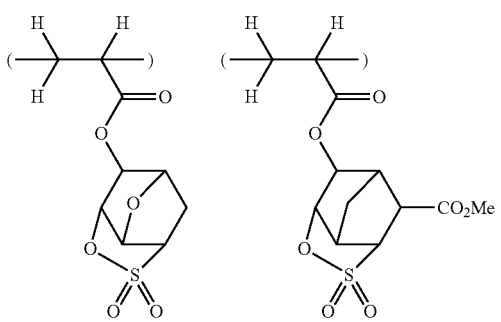
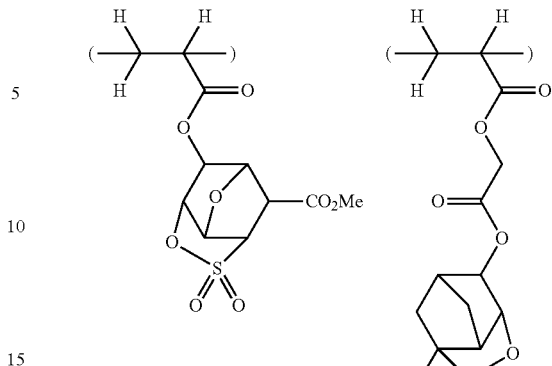
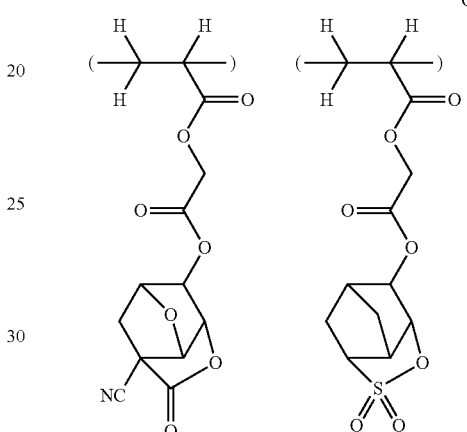
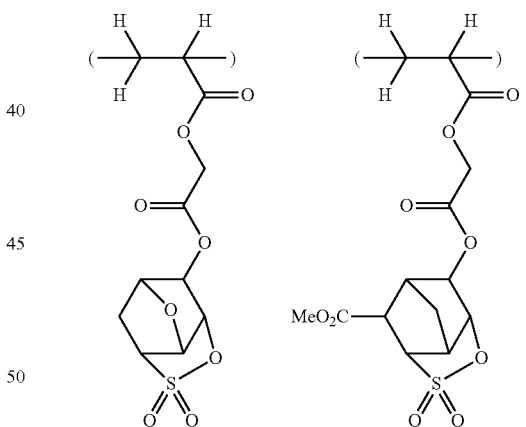
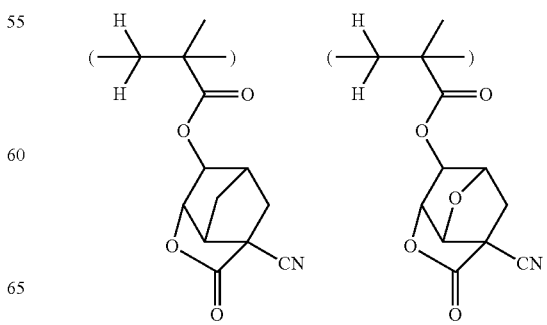

79
-continued
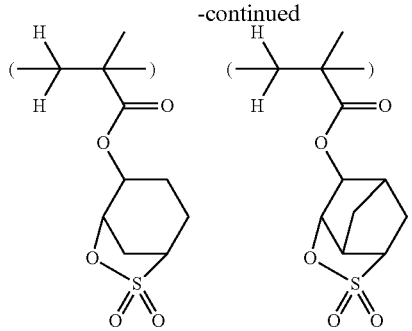
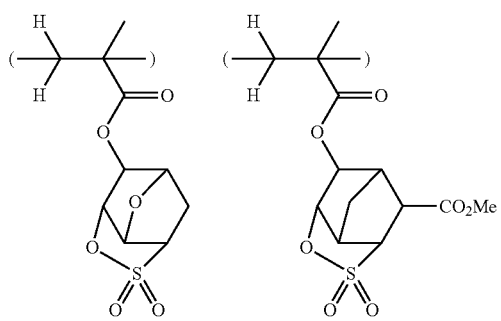
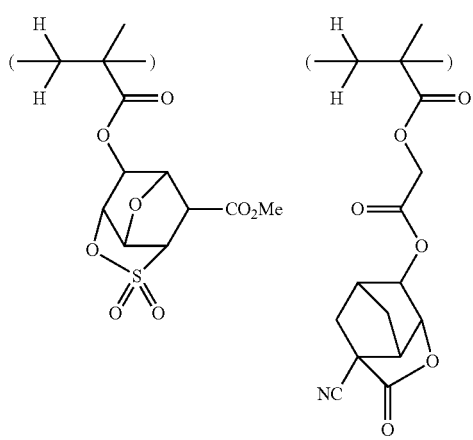
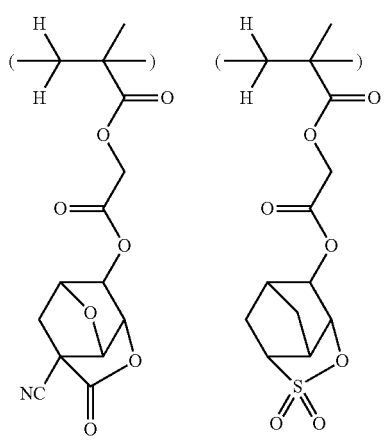
80
-continued
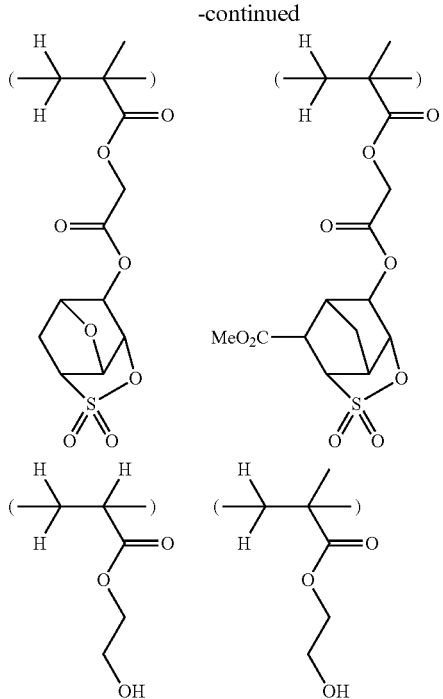
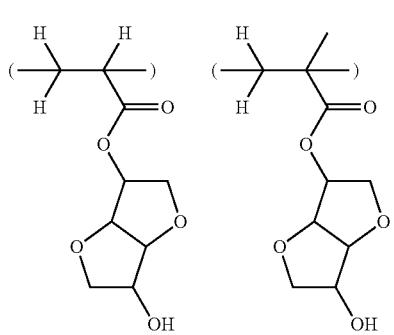
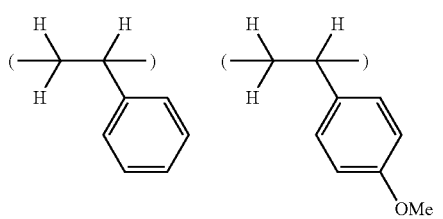
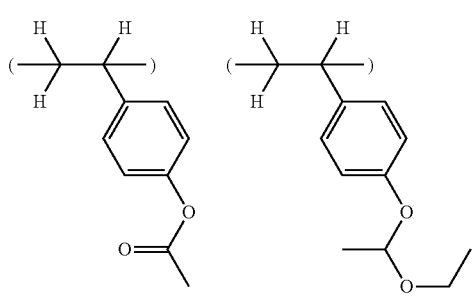

-continued

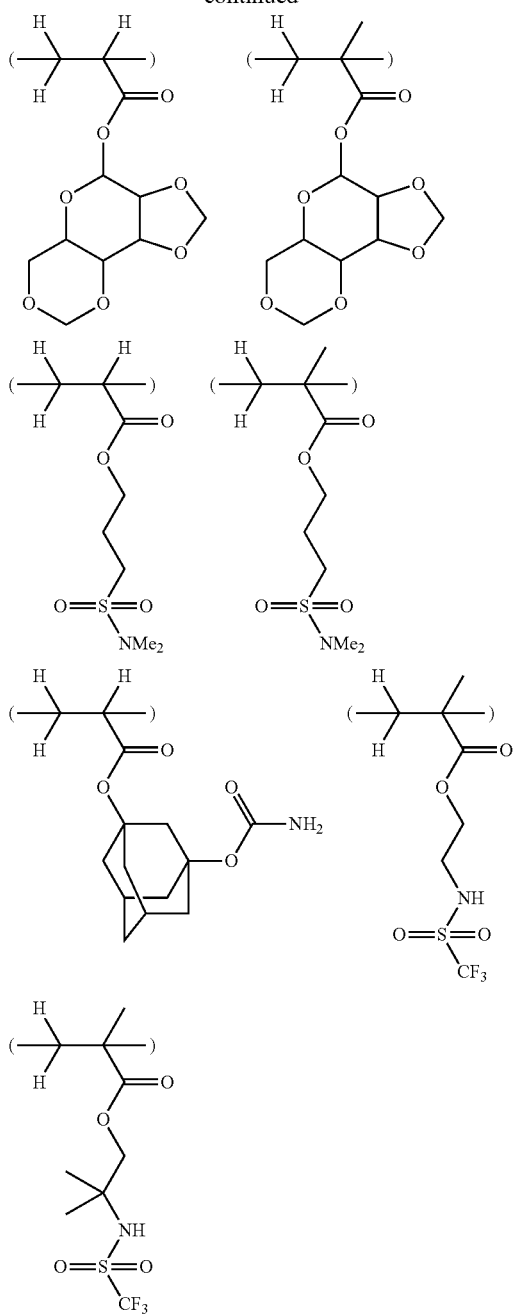

In addition to the foregoing units, the inventive polymer may further comprise recurring units of at least one type selected from recurring units having formulae (f1) to (f3).

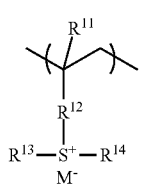
(f1)

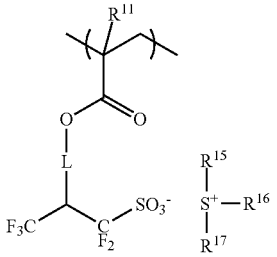
(f2)

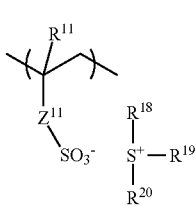
(f3)

Herein $R^{11}$ is each independently hydrogen or methyl. $R^{12}$ is a single bond, phenylene, —O—$R^{21}$—, or —C(=O)—$Z^{22}$—$R^{21}$— wherein $Z^{22}$ is oxygen or NH and $R^{21}$ is a straight, branched or cyclic $C_1$-$C_6$ alkylene group, straight, branched or cyclic $C_2$-$C_6$ alkenylene group or phenylene group, which may contain a carbonyl (—CO—), ester (—COO—), ether (—O—) or hydroxyl moiety. L is a single bond or —$Z^{33}$—C(=O)—O— wherein $Z^{33}$ is a straight, branched or cyclic $C_1$-$C_{20}$ divalent hydrocarbon group which may be substituted with a heteroatom. $Z^{11}$ is a single bond, methylene, ethylene, phenylene, fluorinated phenylene, —O—$R^{22}$—, or —C(=O)—$Z^{44}$—$R^{22}$— wherein $Z^{44}$ is oxygen or NH and $R^{22}$ is a straight, branched or cyclic $C_1$-$C_6$ alkylene group, straight, branched or cyclic $C_2$-$C_6$ alkenylene group or phenylene group, which may contain a carbonyl, ester, ether or hydroxyl moiety. $M^-$ is a non-nucleophilic counter ion.

$R^{13}$ to $R^{20}$ are each independently a straight, branched or cyclic $C_1$-$C_{20}$ monovalent hydrocarbon group which may be substituted with or separated by a heteroatom. Suitable monovalent hydrocarbon groups include alkyl groups such as methyl, ethyl, n-propyl, isopropyl, n-butyl, t-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl, and thienyl; and aralkyl groups such as benzyl, 1-phenylethyl, and 2-phenylethyl, with the aryl groups being preferred. Also included are modified forms of the foregoing groups in which at least one hydrogen atom is replaced by a heteroatom such as oxygen, sulfur, nitrogen or halogen, or in which a heteroatom such as oxygen, sulfur or nitrogen intervenes, and as a result, a hydroxyl group, cyano group, carbonyl group, ether bond, ester bond, sulfonic acid ester bond, carbonate bond, lactone ring, sultone ring, carboxylic acid anhydride, or haloalkyl group forms or intervenes. Also, a pair of $R^{13}$ and $R^{14}$ may bond together to form a ring with the sulfur atom to which they are attached, and any two or more of $R^{15}$, $R^{16}$ and $R^{17}$, or any two or more of $R^{18}$, $R^{19}$ and $R^{20}$ may bond together to form a ring with the sulfur atom to which they are attached.

When L is —$Z^{33}$—C(=O)—O—, examples of the optionally heteroatom-substituted, straight, branched or cyclic $C_1$-$C_{20}$ divalent hydrocarbon group represented by $Z^{33}$ are shown below, but not limited thereto.

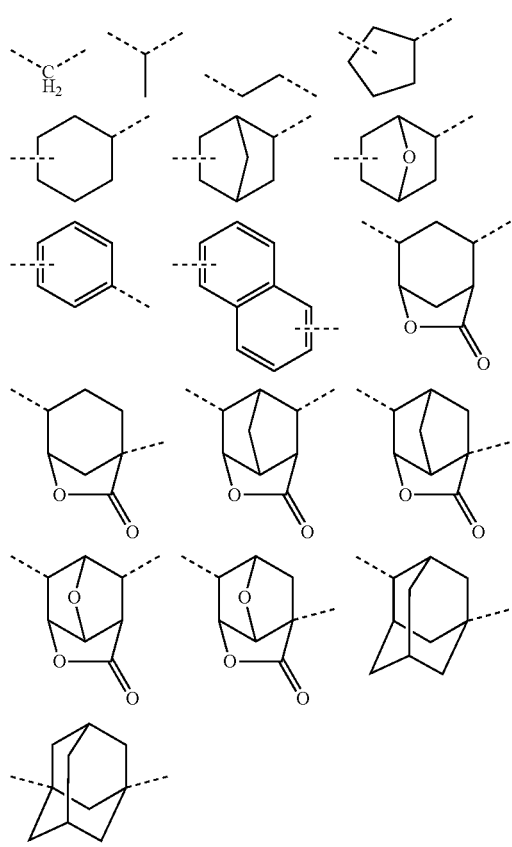

When a pair of $R^{13}$ and $R^{14}$ bond together to form a ring with the sulfur atom to which they are attached, and any two or more of $R^{15}$, $R^{16}$ and $R^{17}$, or any two or more of $R^{18}$, $R^{19}$ and $R^{20}$ bond together to form a ring with the sulfur atom to which they are attached, examples of the ring are shown below, but not limited thereto.

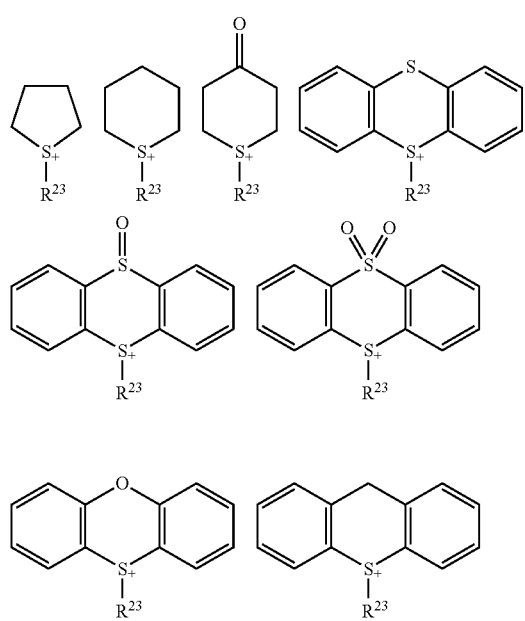

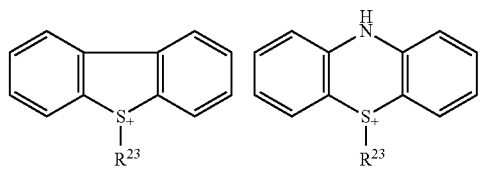

In the formulae, $R^{23}$ is a straight, branched or cyclic $C_1$-$C_{20}$ monovalent hydrocarbon group which may be substituted with or separated by a heteroatom. Suitable monovalent hydrocarbon groups are as exemplified above for $R^{13}$ to $R^{20}$.

Illustrative, non-limiting examples of the sulfonium cation in formulae (f2) and (f3) are given below.

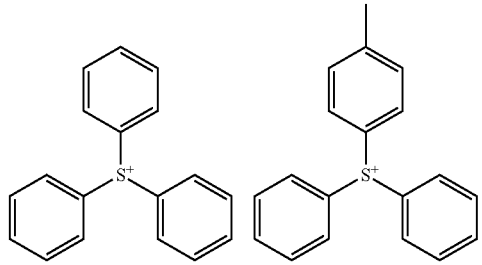

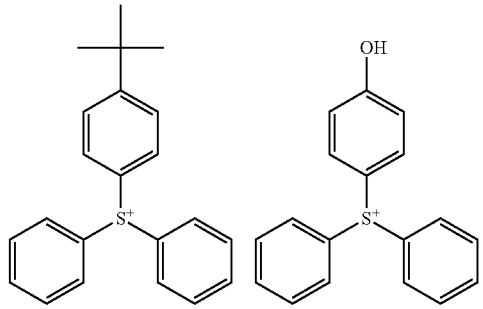

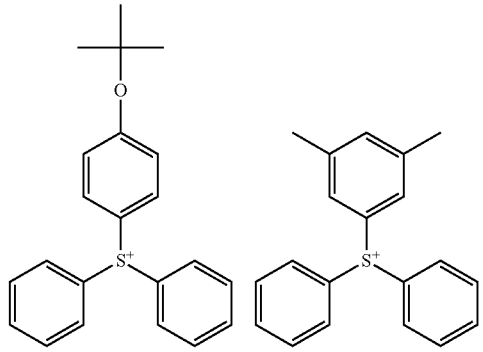

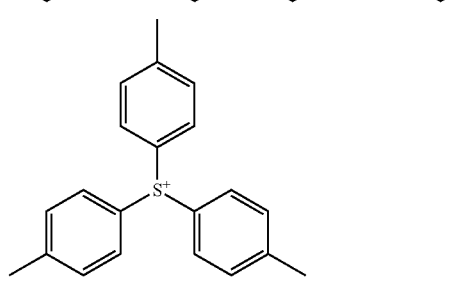

-continued
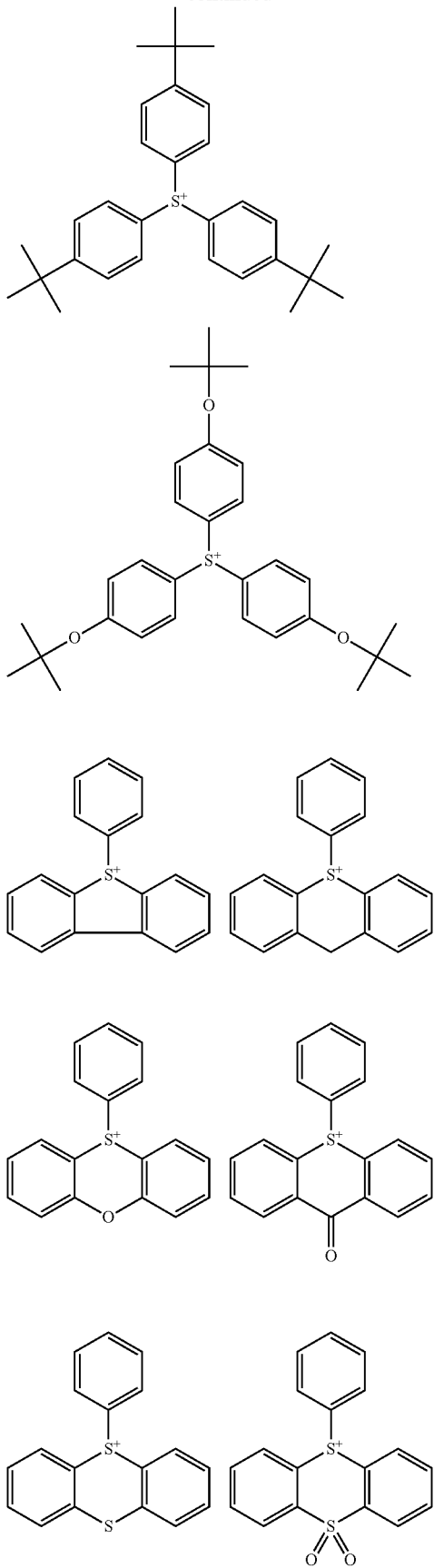
-continued
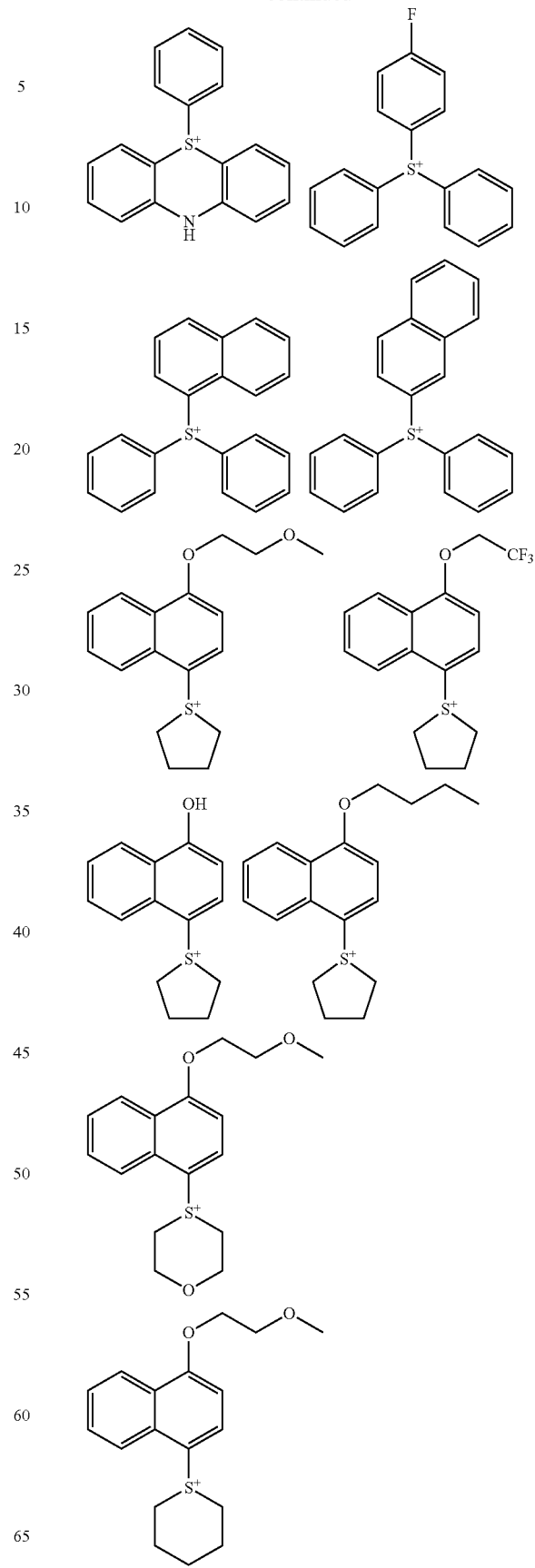

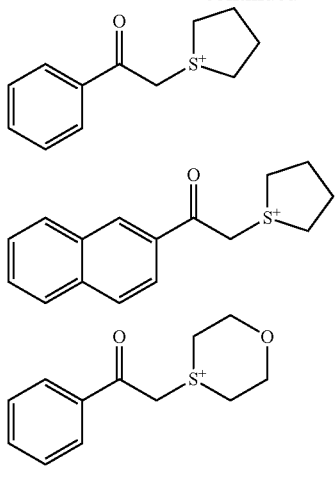

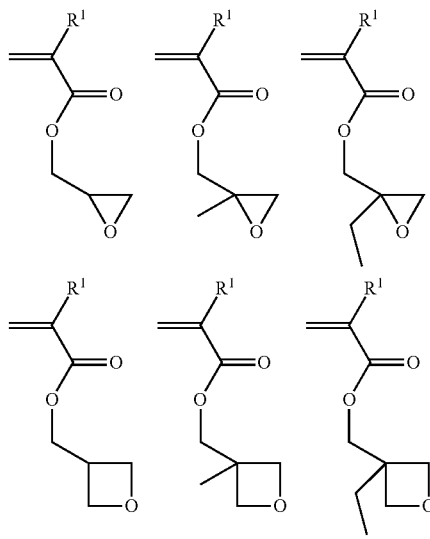

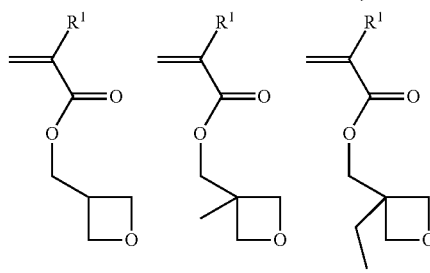

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; and methidates such as tris(trifluoromethylsulfonyl)methide and tris(perfluoroethylsulfonyl)methide.

Also included are a sulfonate which is fluorinated at α-position as represented by the formula (F-1) and a sulfonate which is fluorinated at α- and β-positions as represented by the formula (F-2).

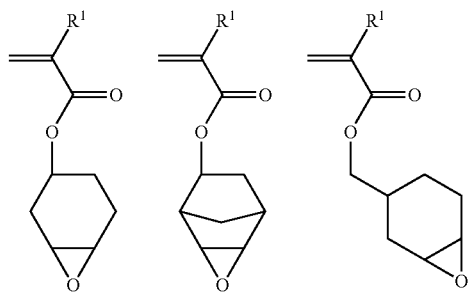

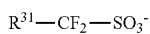

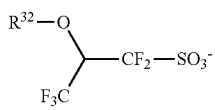

In formula (F-1), $R^{31}$ is hydrogen, or a straight, branched or cyclic $C_1$-$C_{20}$ alkyl group, straight, branched or cyclic $C_2$-$C_{20}$ alkenyl group or $C_6$-$C_{20}$ aryl group, which may have an ether, ester, carbonyl moiety, lactone ring or fluorine atom. In formula (F-2), $R^{32}$ is hydrogen, or a straight, branched or cyclic $C_1$-$C_{30}$ alkyl group, straight, branched or cyclic $C_2$-$C_{30}$ acyl group, straight, branched or cyclic $C_2$-$C_{20}$ alkenyl group, $C_6$-$C_{20}$ aryl group or $C_6$-$C_{20}$ aryloxy group, which may have an ether, ester, carbonyl moiety or lactone ring.

Furthermore, recurring units (g) having an oxirane or oxetane ring may be copolymerized. When recurring units (g) are copolymerized, it is expected that when the polymer is used in a resist composition, the exposed region of a resist film is crosslinked, leading to improvements in insolubilization in alkaline developer and etch resistance of negative pattern. Examples of monomers providing recurring units (g) having an oxirane or oxetane ring are shown below, but not limited thereto. Note that $R^1$ is as defined above.

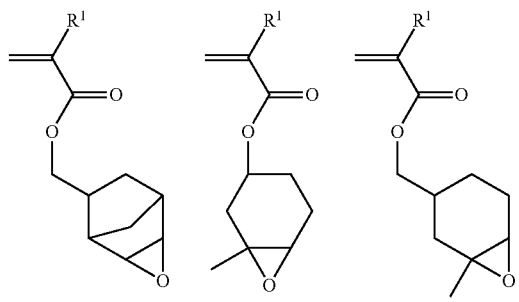

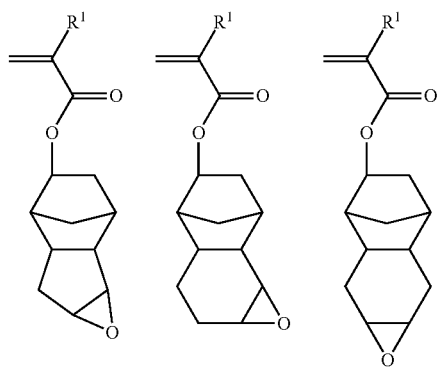

-continued
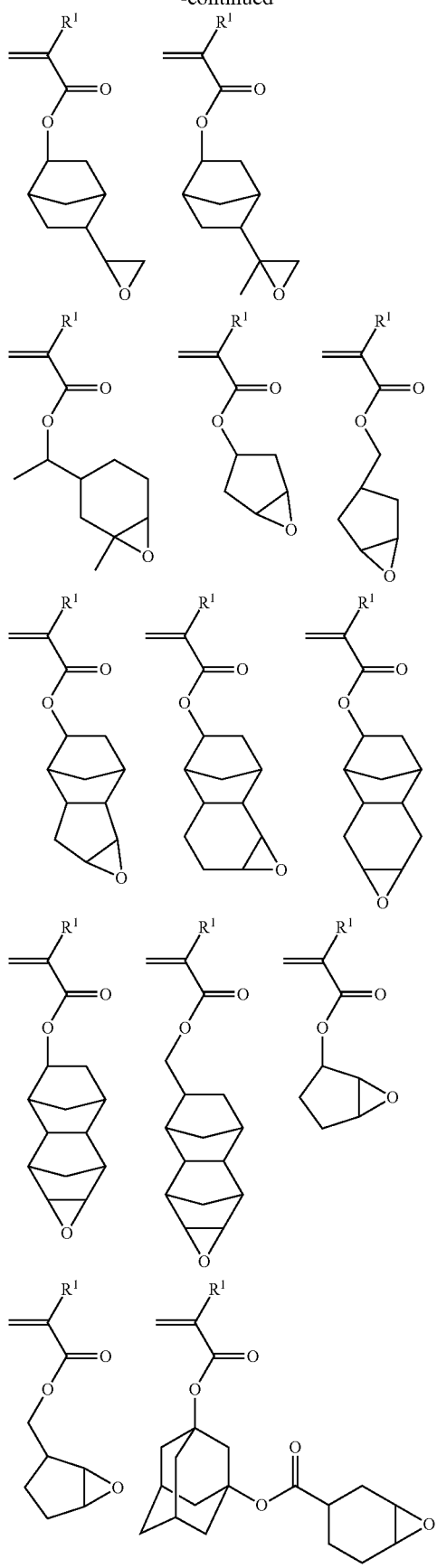
-continued
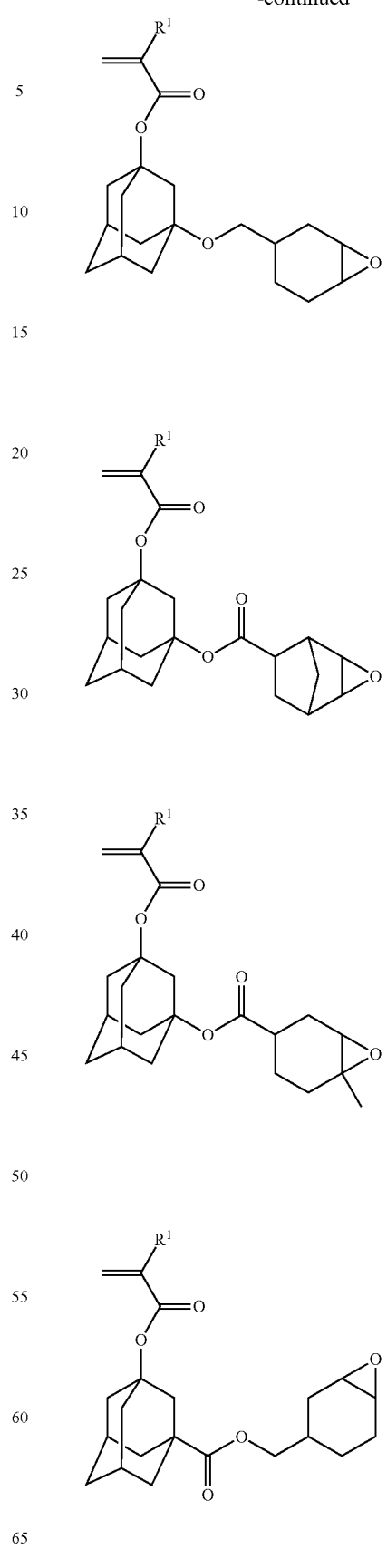

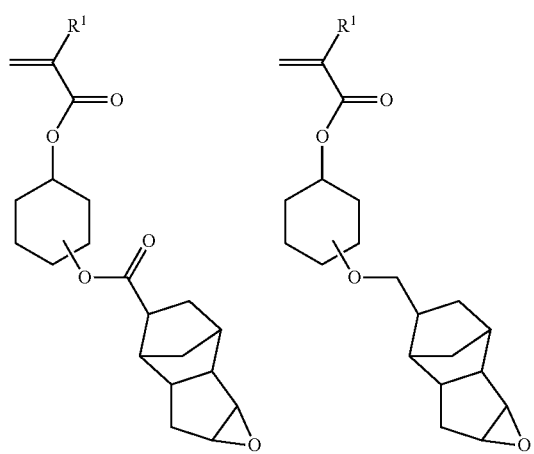
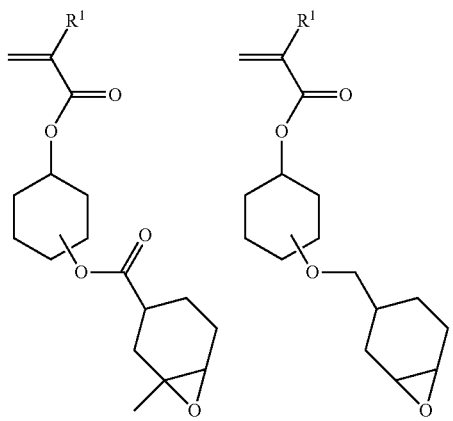
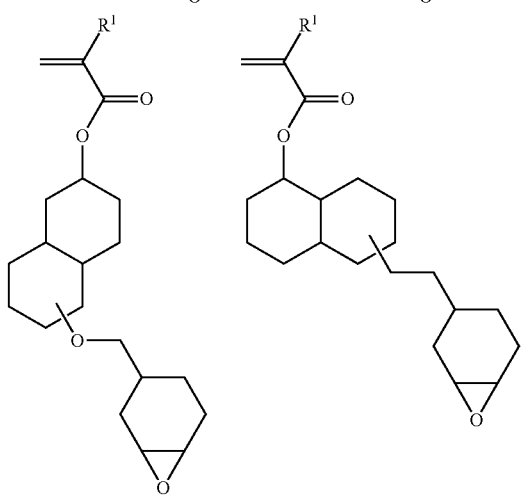
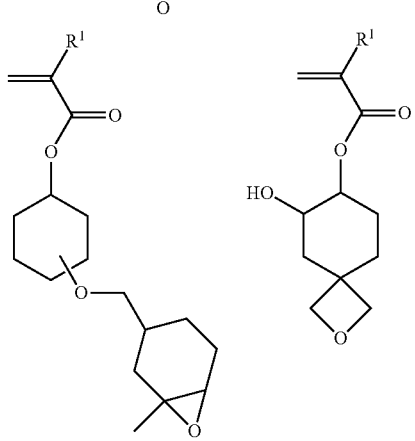
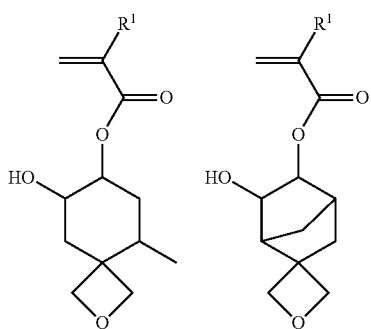

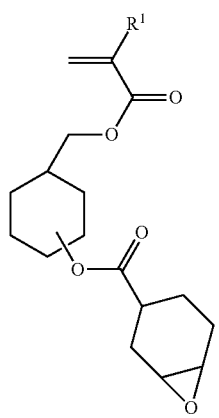

In addition to the foregoing units, the polymer may further comprise recurring units (h) derived from carbon-to-carbon double bond-bearing monomers. Examples include recurring units derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo [4.4.0.1$^{2,5}$.1$^{7,10}$]dodecene derivatives, unsaturated acid anhydrides such as itaconic anhydride, and other monomers shown below. In the following examples, R$^1$ is as defined above.

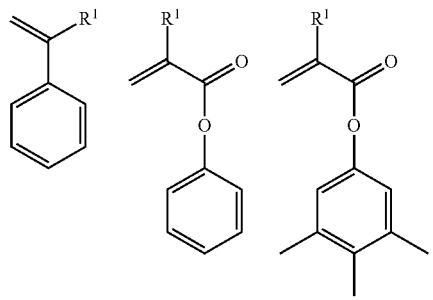

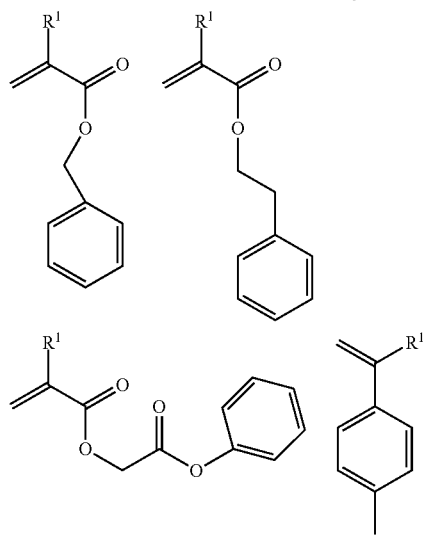

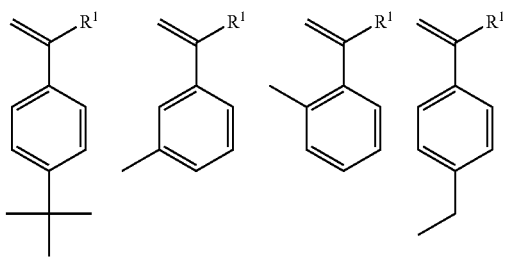

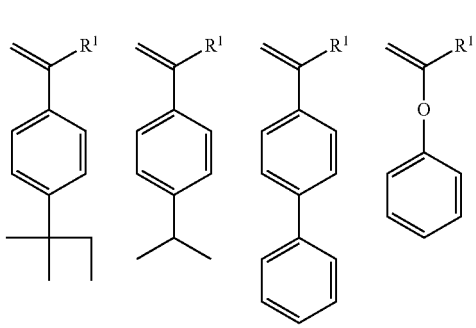

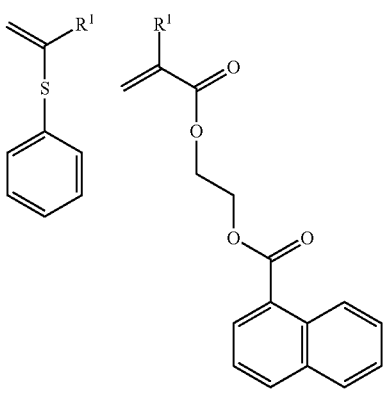

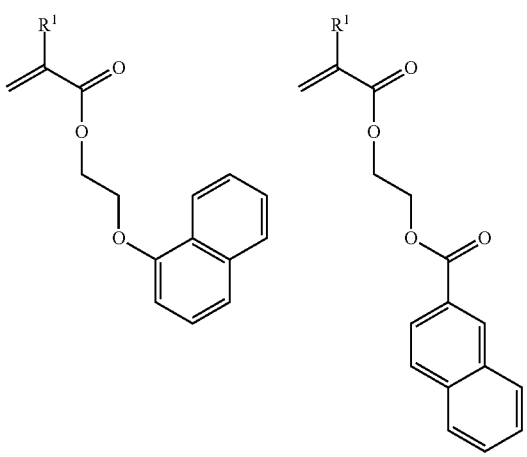

95
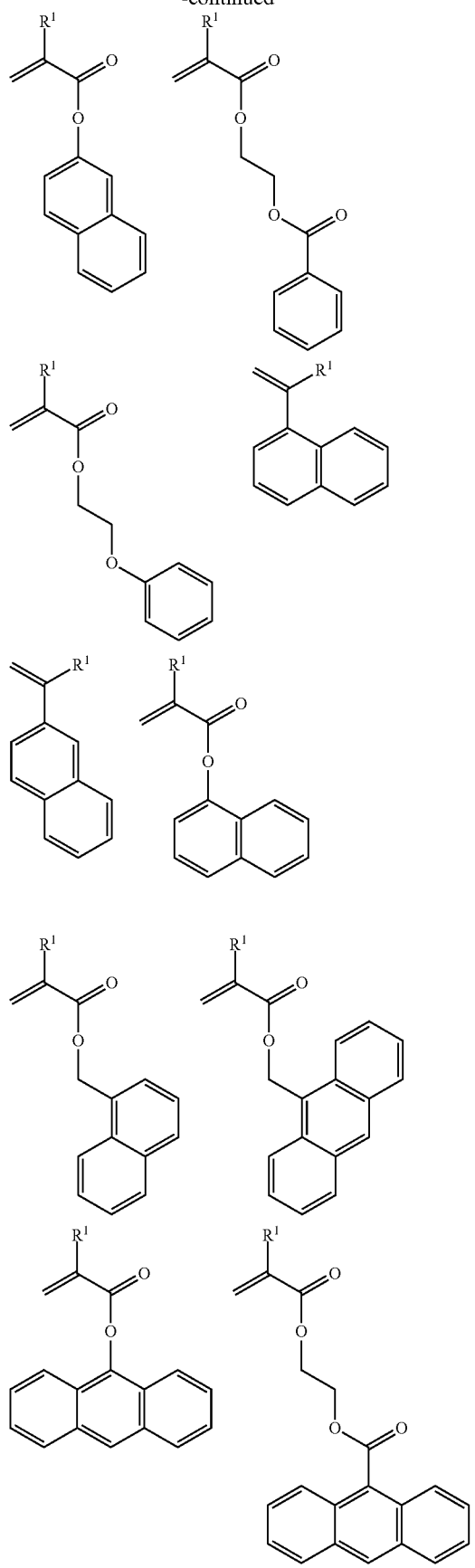
-continued
96
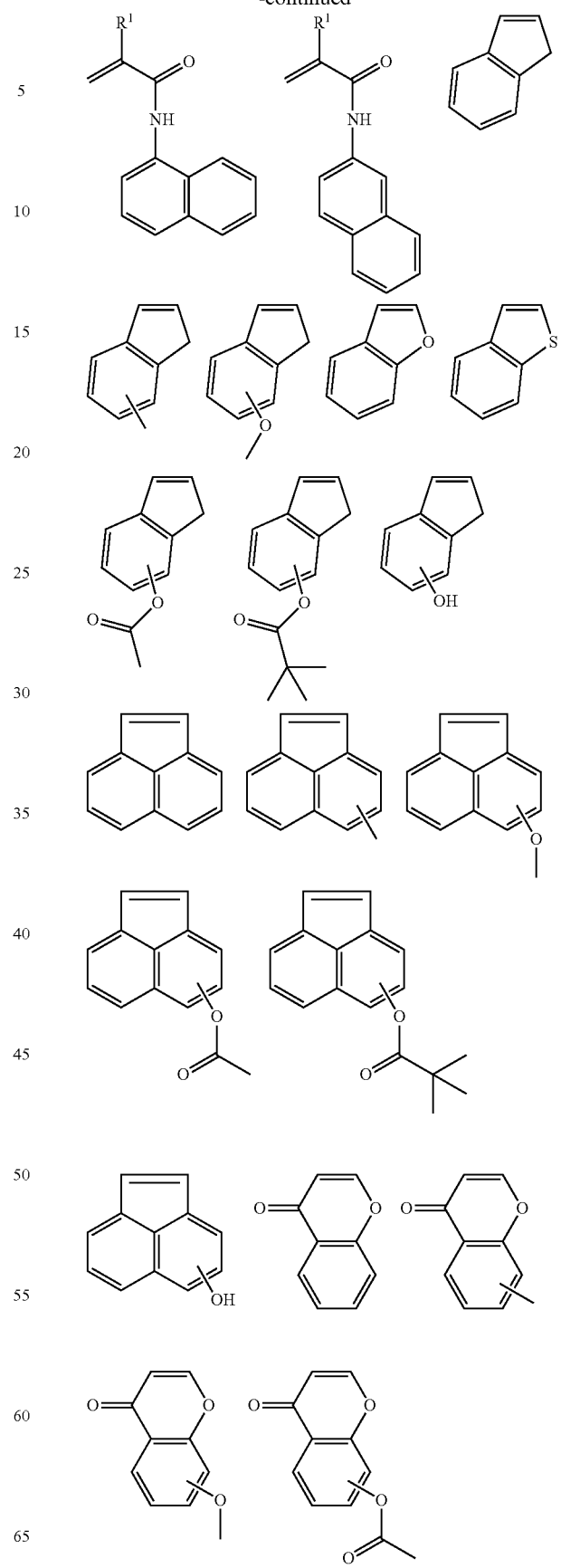
-continued

-continued

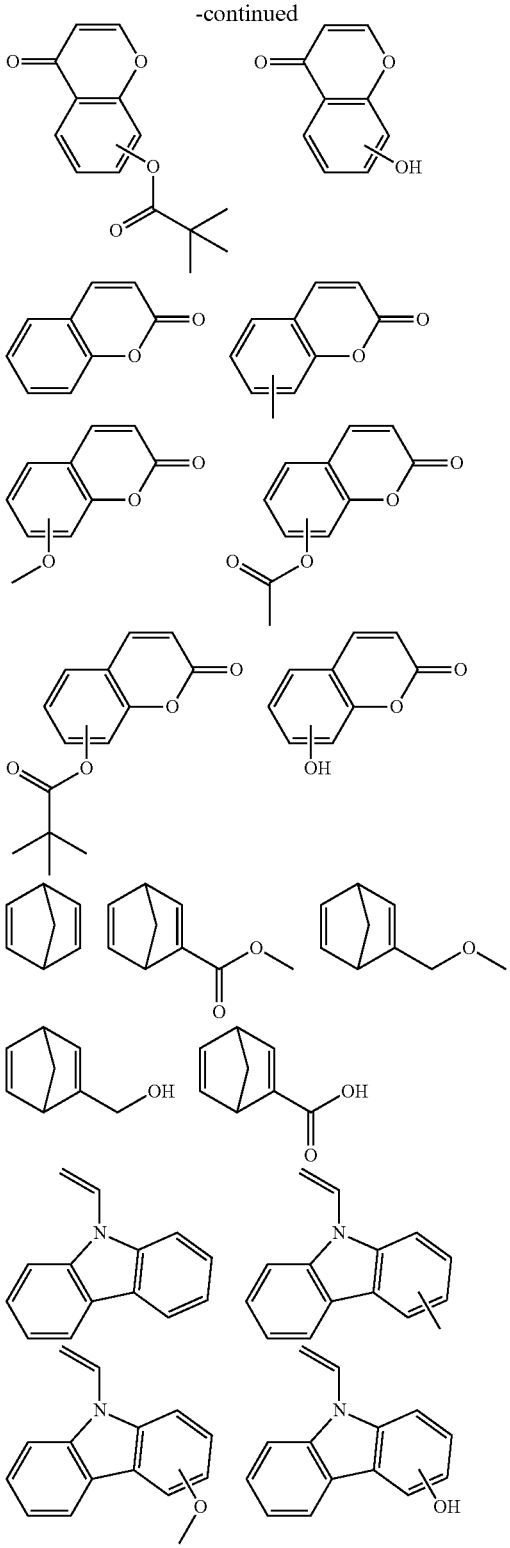

In the polymer, the recurring units derived from the inventive monomer and other monomers are preferably incorporated in the following molar fractions (mol %):

(I) more than 0 mol % to 100 mol %, preferably 5 to 80 mol %, and more preferably 10 to 60 mol % of constituent units of at least one type selected from formulae (1a) and (1b);

(II) 0 mol % to less than 100 mol %, preferably 0 to 90 mol %, and more preferably 0 to 80 mol % of constituent units of at least one type selected from formula (1c), when used, at least 1 mol %, more preferably at least 4 mol %;

(III) 0 mol % to less than 100 mol % preferably 5 to 95 mol %, and more preferably 10 to 90 mol % of constituent units of at least one type selected from formulae (A) to (D), when used, at least 4 mol %, more preferably at least 5 mol %;

(IV) 0 to 30 mol %, preferably 0 to 20 mol %, and more preferably 0 to 10 mol % of constituent units of at least one type selected from formulae (f1) to (f3); and (V) 0 to 80 mol %, preferably 0 to 70 mol %, and more preferably 0 to 50 mol % of constituent units of at least one type selected from units (g) and (h).

The polymer may be synthesized by any desired methods, for example, by dissolving one or more monomers corresponding to the selected recurring units in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, a copolymer may be obtained by dissolving hydroxystyrene or hydroxyvinylnaphthalene and another monomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The inventive polymer should preferably have a weight average molecular weight (Mw) in the range of 1,000 to 500,000, and more preferably 3,000 to 50,000, as measured versus polystyrene standards by GPC using tetrahydrofuran solvent. Outside the range, there may result an extreme decline of etch resistance, a failure to provide a differential dissolution rate before and after exposure, and a lowering of resolution. Also preferably, the polymer has a molecular weight distribution or dispersity (Mw/Mn) of 1.20 to 2.20, more preferably 1.30 to 1.80.

Resist Composition

The inventive polymer is advantageously used as a base resin in a resist composition. Specifically, the polymer is used as a base resin and combined with any desired components including an organic solvent, acid generator, dissolution regulator, basic compound, surfactant, and acetylene alcohol to formulate a resist composition.

The resist composition comprising the inventive polymer has a very high sensitivity in that the dissolution rate in alkaline developer of the polymer in the exposed region is reduced by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Inclusion of a dissolution regulator may lead to an increased difference in dissolution rate between exposed and unexposed regions and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified negative resist composition. Typical of the acid generator used herein is a photoacid generator (PAG) capable of generating an acid in response to actinic light or radiation. Preferably the PAG is used in an amount of 0.5 to 30 parts, more preferably 1 to 20 parts by weight per 100 parts by weight of the base resin. The PAG is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used. These compounds may be used alone or in admixture. Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection. Where the base polymer having recurring units (f1), (f2) or (f3) of acid generator copolymerized therein is used, the acid generator of addition type is not essential.

The preferred acid generators are those having the formulae (Z1) and (Z2).

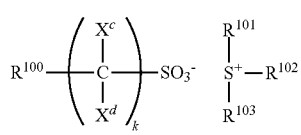
(Z1)

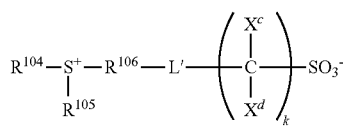
(Z2)

Herein $R^{100}$ is hydrogen, fluorine, or a straight, branched or cyclic $C_1$-$C_{35}$ monovalent hydrocarbon group which may be substituted with or separated by a heteroatom. $X^c$ and $X^d$ are each independently hydrogen, fluorine, or trifluoromethyl, k is an integer of 1 to 4. $R^{101}$, $R^{102}$, and $R^{103}$ are each independently an optionally substituted, straight or branched $C_1$-$C_{10}$ alkyl, $C_1$-$C_{10}$ oxoalkyl or $C_2$-$C_{10}$ alkenyl group, or an optionally substituted $C_6$-$C_{18}$ aryl, $C_7$-$C_{19}$ aralkyl or aryloxoalkyl group, or any two or more of $R^{101}$, $R^{102}$, and $R^{103}$ may bond together to form a ring with the sulfur atom to which they are attached. $R^{104}$ and $R^{105}$ are each independently a straight, branched or cyclic $C_1$-$C_{20}$ monovalent hydrocarbon group which may be substituted with or separated by a heteroatom, or $R^{104}$ and $R^{105}$ may bond together to form a ring with the sulfur atom to which they are attached. $R^{106}$ is a straight, branched or cyclic $C_1$-$C_{20}$ divalent hydrocarbon group which may be substituted with or separated by a heteroatom. L' is a single bond, ether bond, or a straight, branched or cyclic $C_1$-$C_{20}$ divalent hydrocarbon group which may be substituted with or separated by a heteroatom. As used herein, the phrase "hydrocarbon group which may be substituted with or separated by a heteroatom" means that one or more or even all hydrogen atoms may be substituted by heteroatoms or a heteroatom may intervene in a carbon-carbon bond.

Also preferred are acid generators having the formulae (Z3) and (Z4).

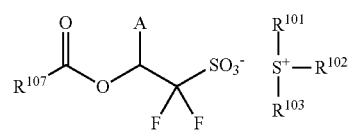
(Z3)

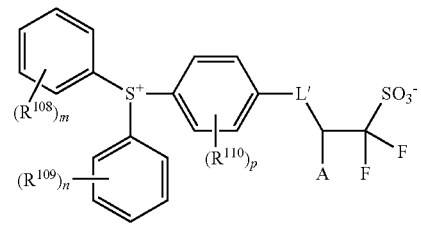
(Z4)

Herein A is hydrogen or trifluoromethyl. $R^{101}$, $R^{102}$, and $R^{103}$ are as defined above. $R^{107}$ is a straight, branched or cyclic $C_1$-$C_{35}$ monovalent hydrocarbon group which may be substituted with or separated by a heteroatom. $R^{108}$, $R^{109}$, and $R^{110}$ are each independently hydrogen or a straight, branched or cyclic $C_1$-$C_{20}$ monovalent hydrocarbon group which may be separated by a heteroatom. Each of m and n is an integer of 0 to 5, p is an integer of 0 to 4. L' is a single bond, ether bond, or a straight, branched or cyclic $C_1$-$C_{20}$ divalent hydrocarbon group which may be substituted with or separated by a heteroatom.

When the acid generator is one having formula (Z3) or (Z4), preferably formula (Z3) or (Z4) wherein A is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of the acid generators having formulae (Z1) to (Z4) are shown below. Notably A is as defined above.

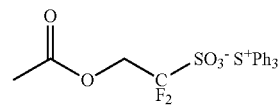

101
-continued
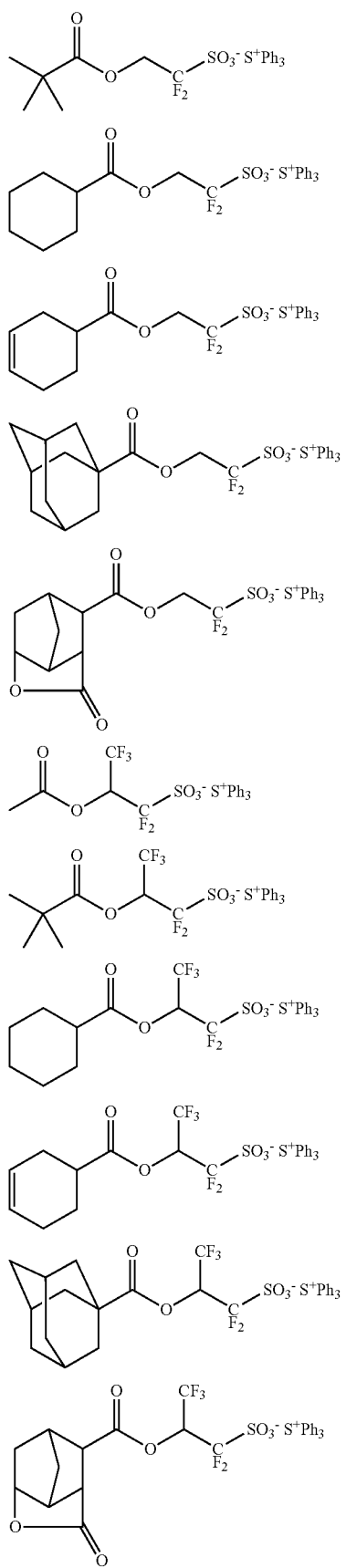
102
-continued
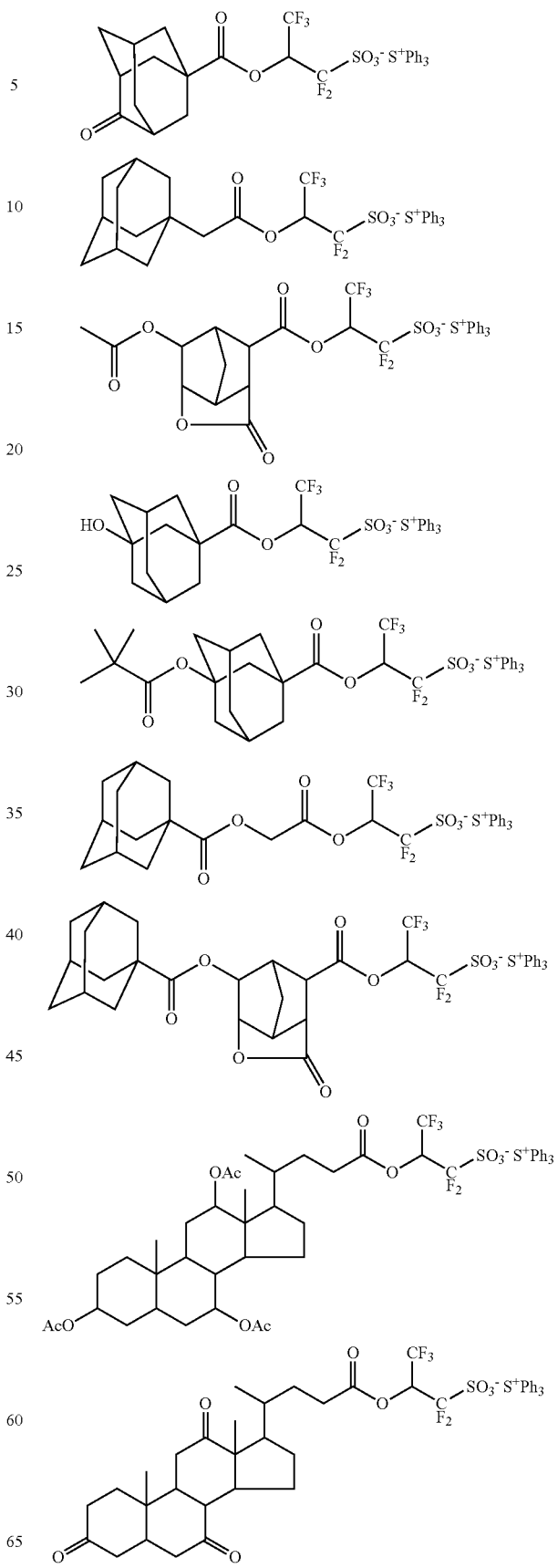

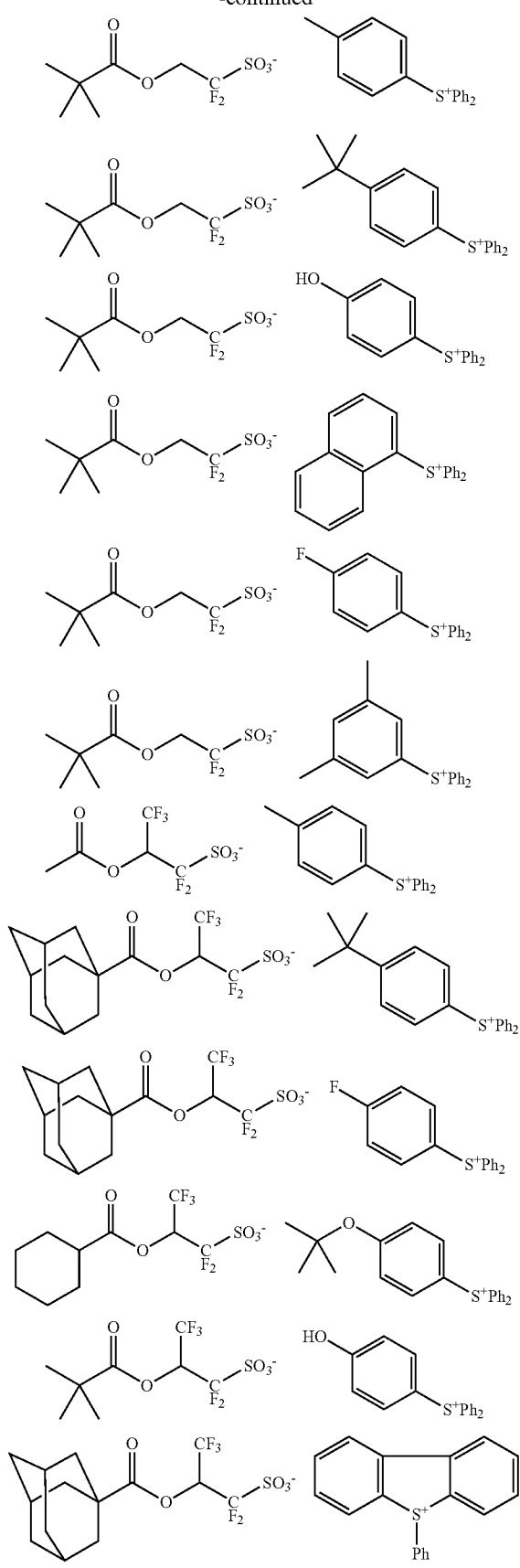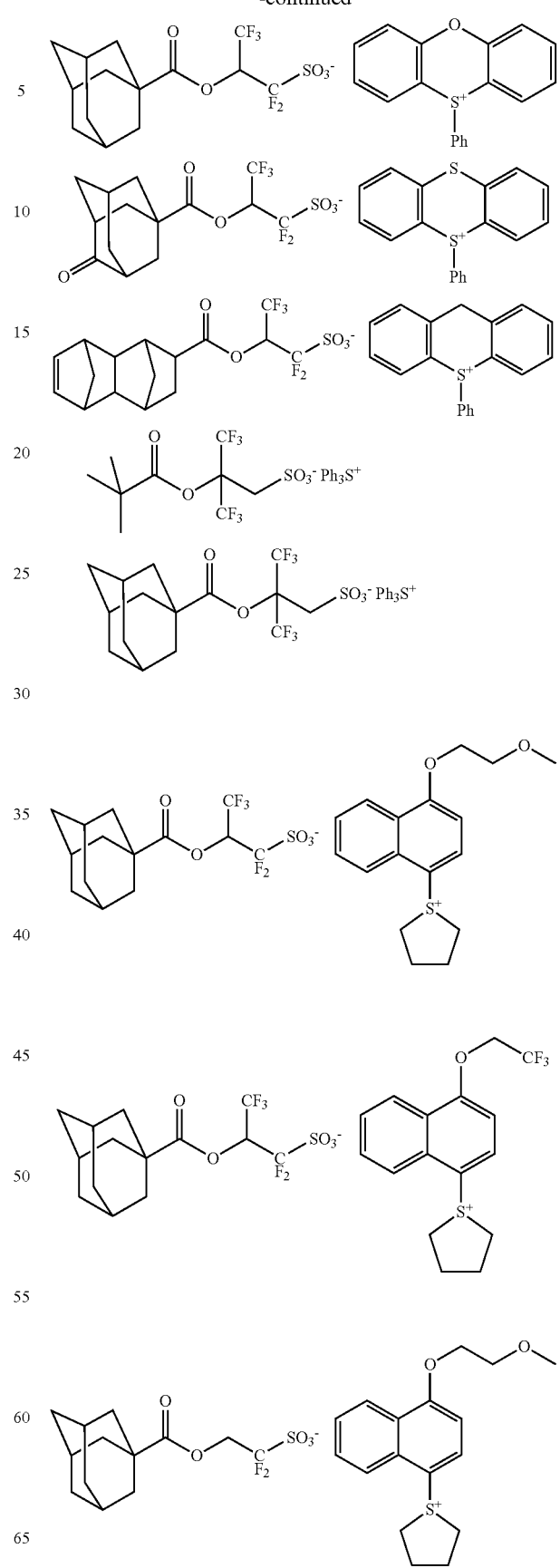

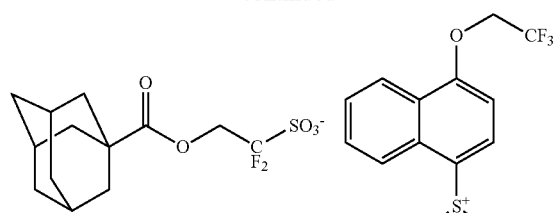
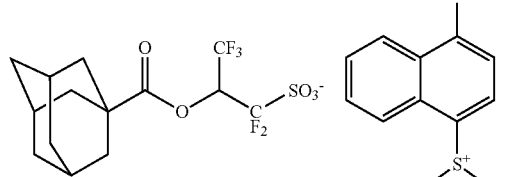
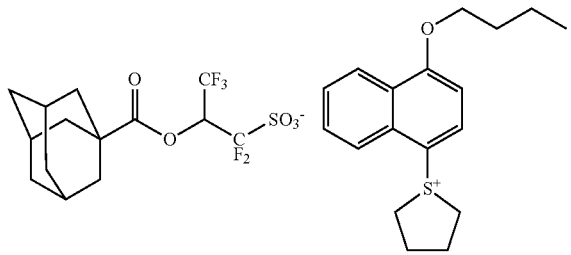
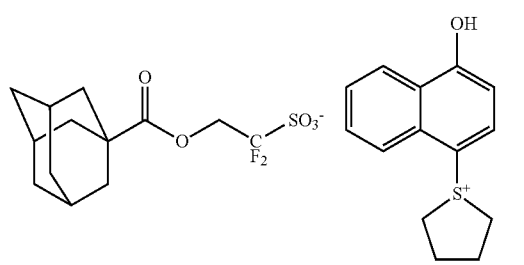
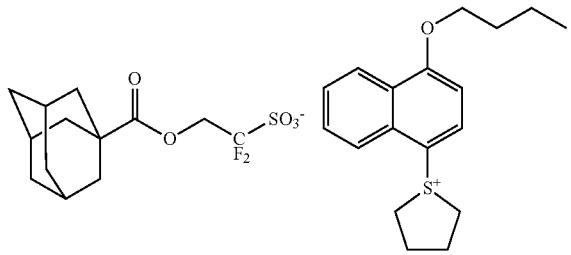
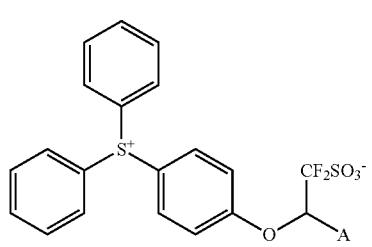
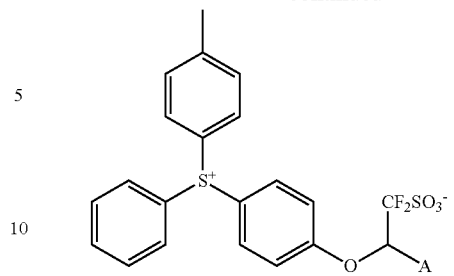
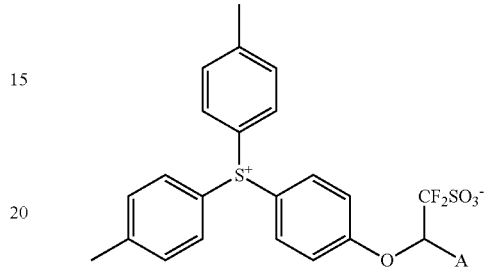
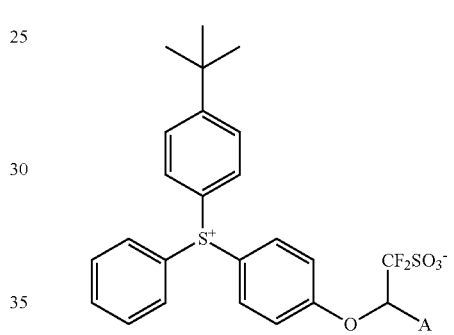
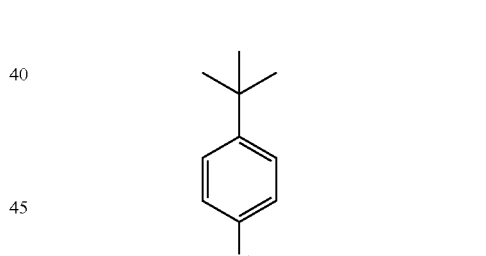
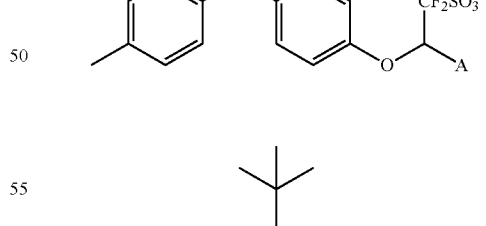
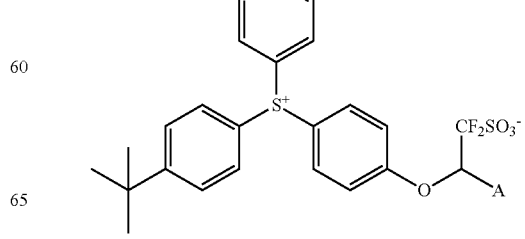

107
-continued
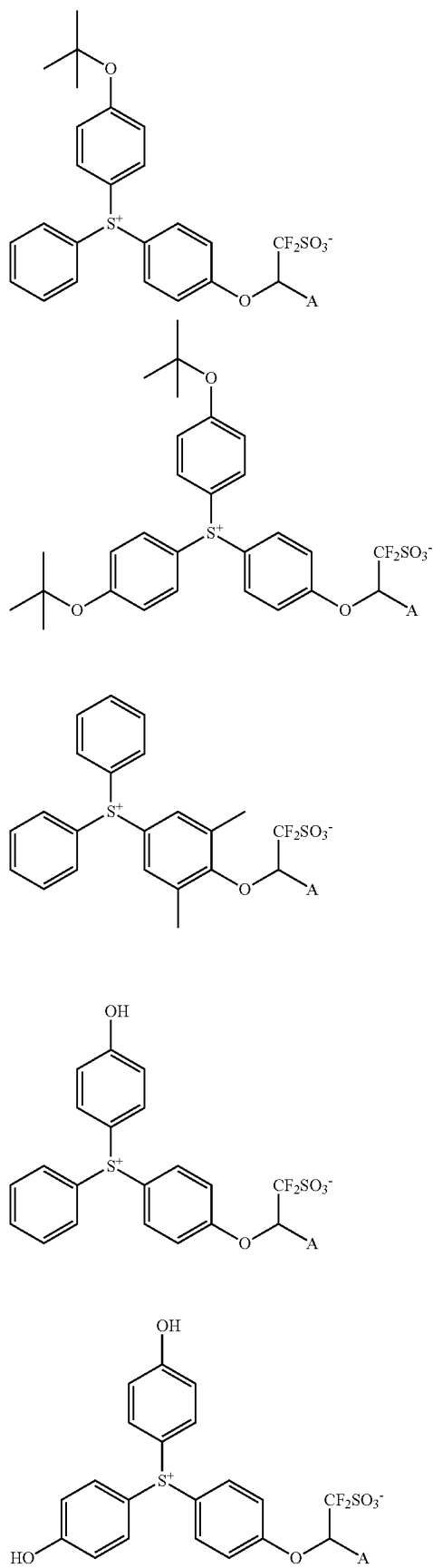
108
-continued
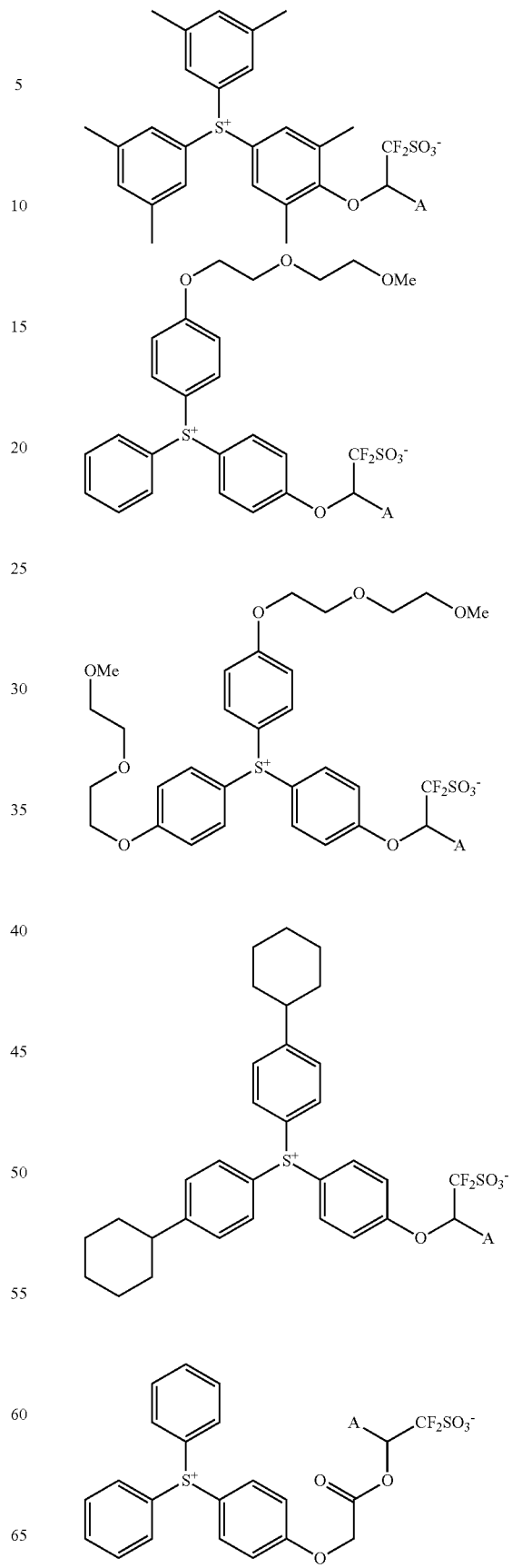

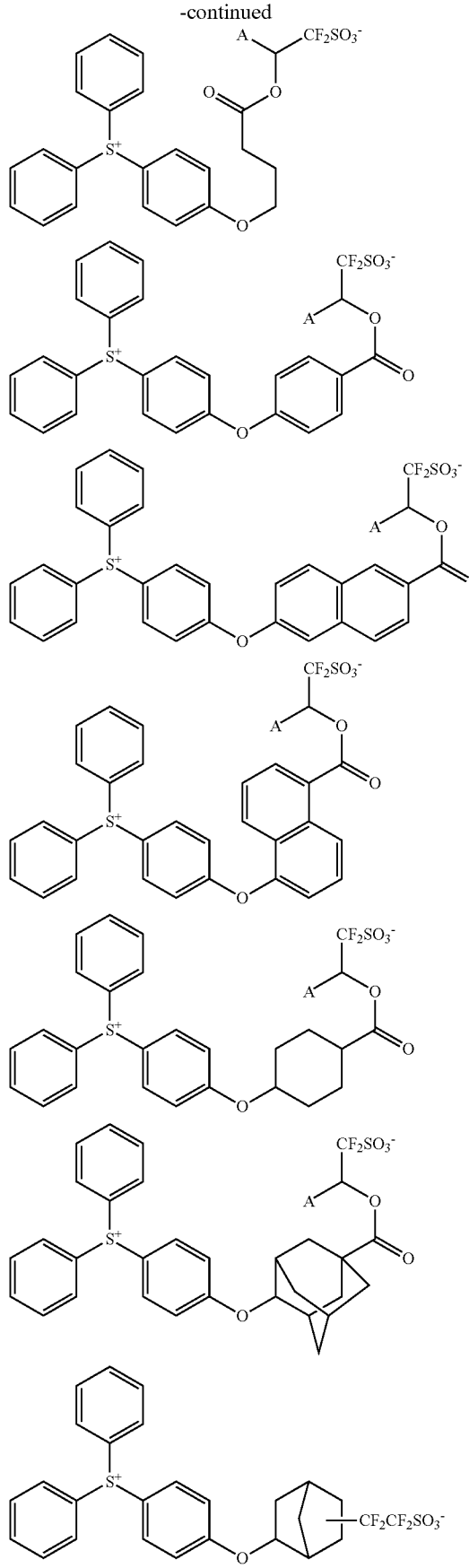
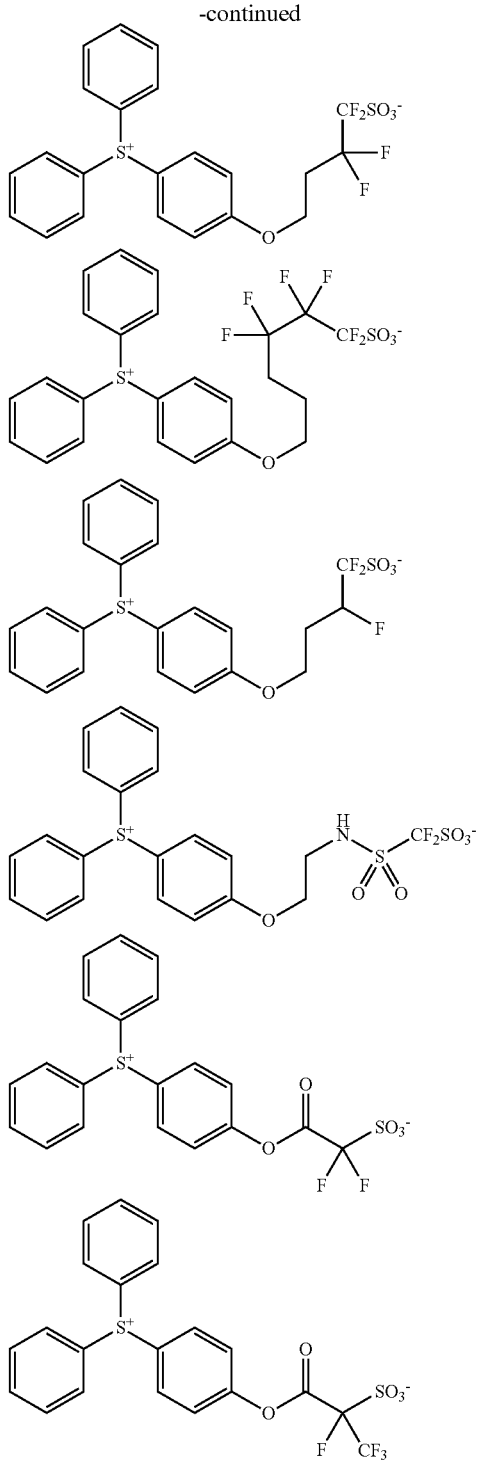

Suitable organic solvents include ketones such as cyclohexanone, cyclopentanone, methyl-2-n-pentyl ketone, and diacetone alcohol; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone, which may be used alone or in admixture.

Examples of the basic compound used herein include primary, secondary, and tertiary amine compounds as described in JP-A 2008-111103 (U.S. Pat. No. 7,537,880), paragraphs [0146] to [0164], specifically amine compounds having a hydroxyl, ether, ester, lactone, cyano or sulfonic ester group, and compounds having a carbamate group as described in JP 3790649.

Onium salts such as sulfonium salts, iodonium salts and ammonium salts of sulfonic acids which are not fluorinated at α-position as described in US 2008153030 (JP-A 2008-158339) and similar onium salts of carboxylic acids as described in JP-A 2013-037092 may be used as the quencher. Where an α-position non-fluorinated sulfonic acid salt or carboxylic acid salt and an α-position fluorinated sulfonic acid, imide acid, or methide acid generated by a PAG are co-present, salt exchange occurs to generate an α-position non-fluorinated sulfonic acid or carboxylic acid. Since this α-position non-fluorinated sulfonic acid or carboxylic acid has an insufficient acid strength to induce deprotection reaction to the resist resin, the relevant sulfonium salt, iodonium salt or ammonium salt functions as a quencher. In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed region, further improved focus margin or DOF and satisfactory dimensional control.

In case the polarity switching unit of formula (1a) or (1b) in the base resin has a high reactivity with acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Illustrative, non-limiting examples of the α-position non-fluorinated sulfonic acid salt and carboxylic acid salt are given below.

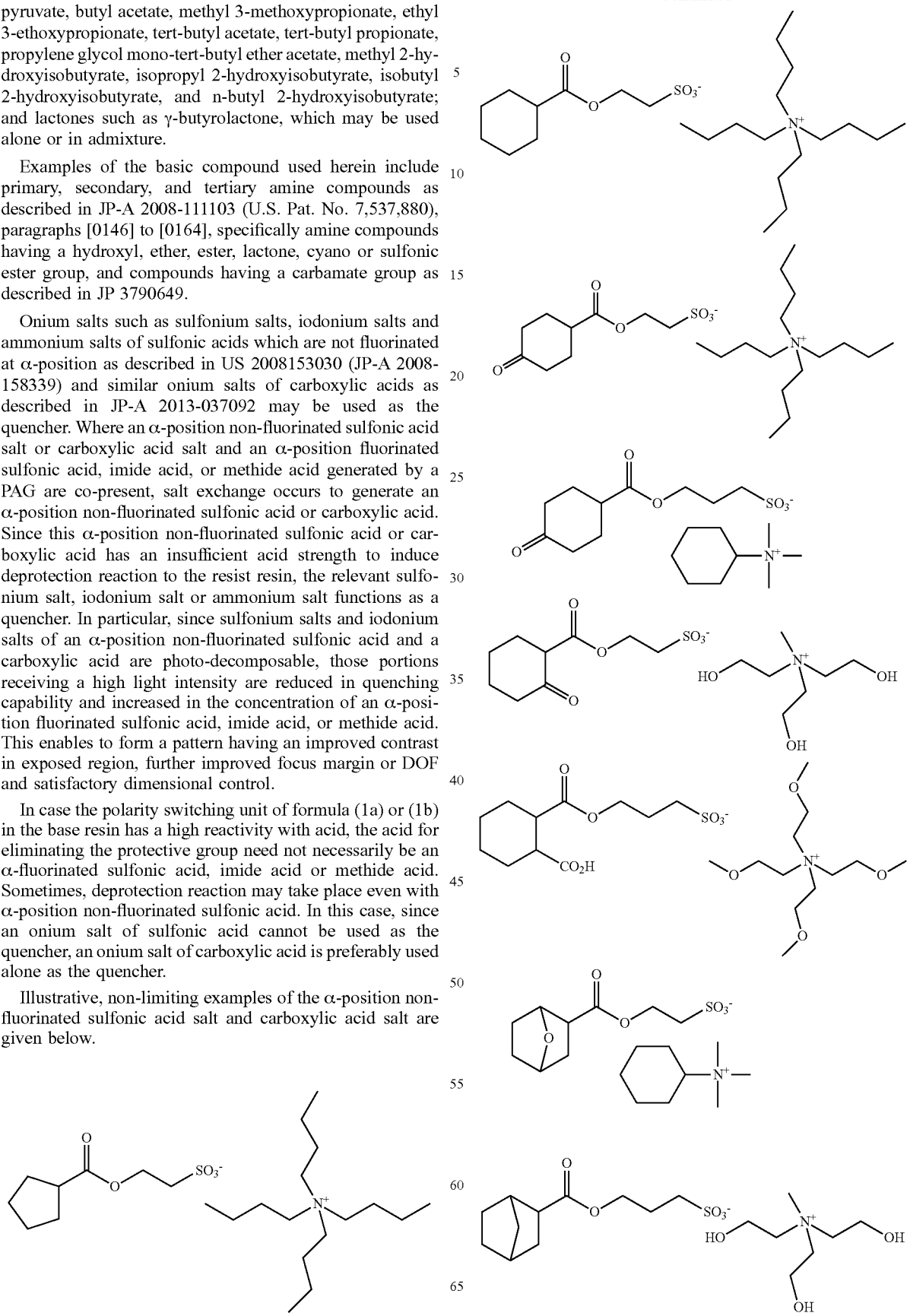

113
-continued
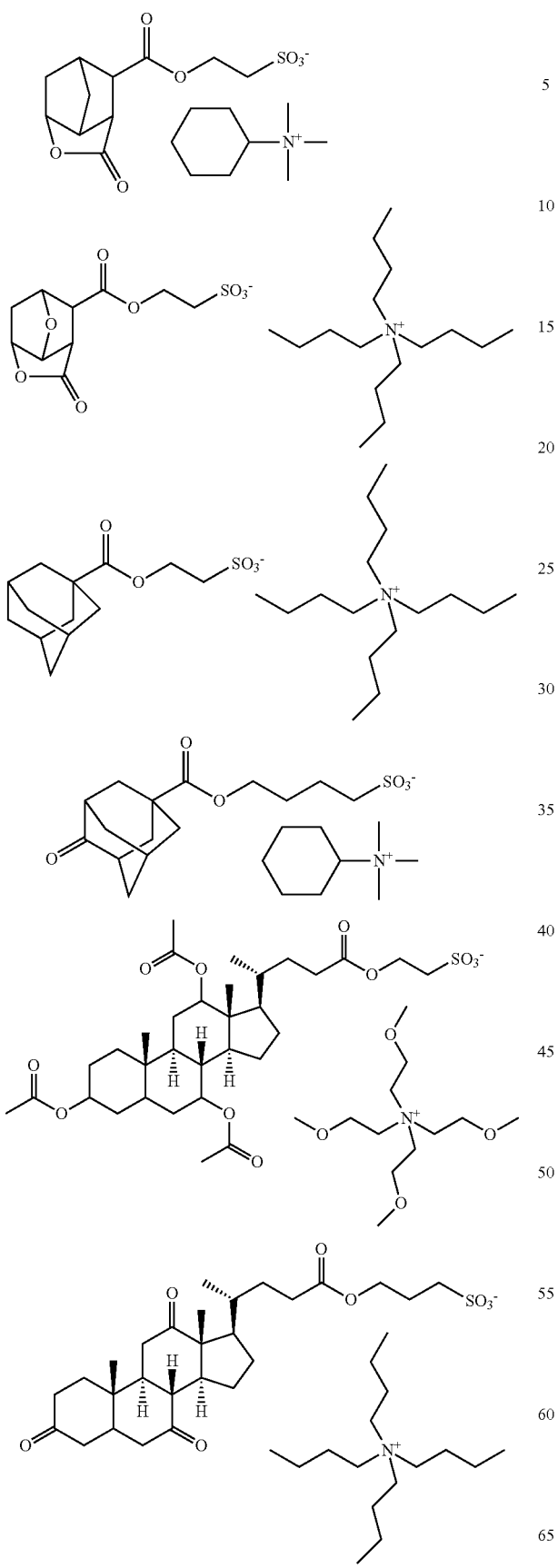
114
-continued
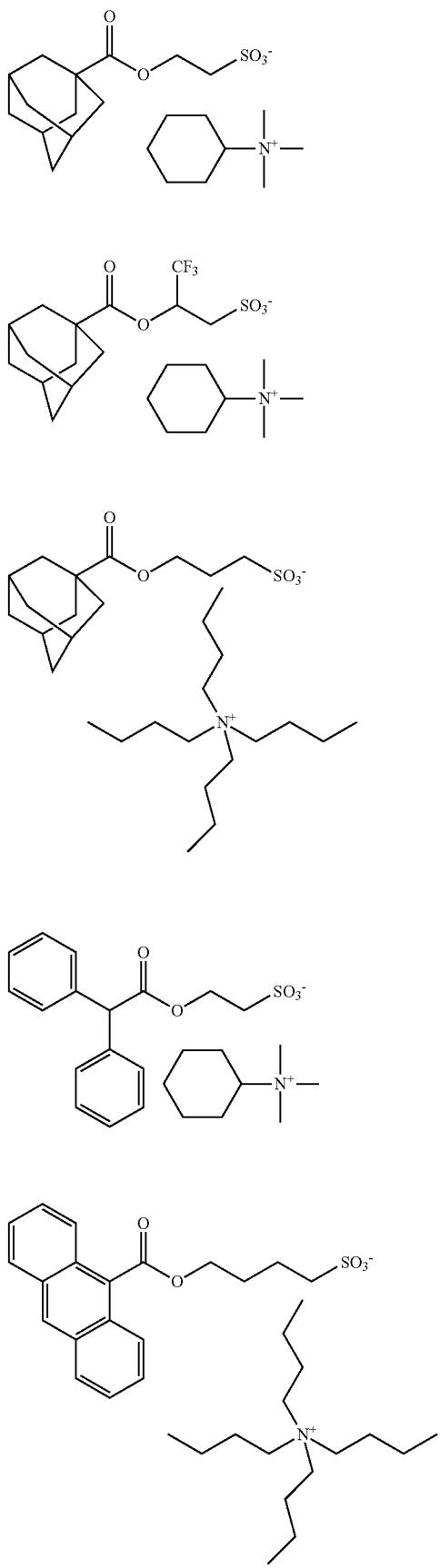

115
-continued
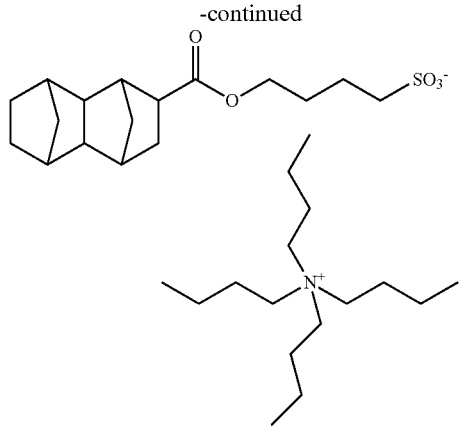
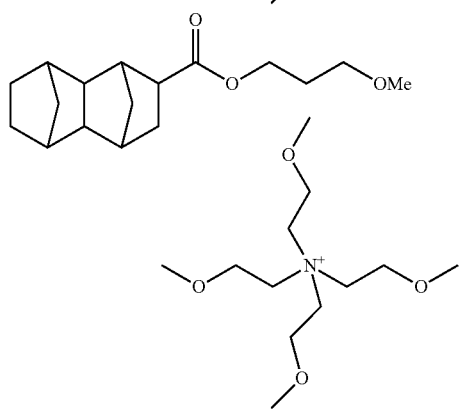
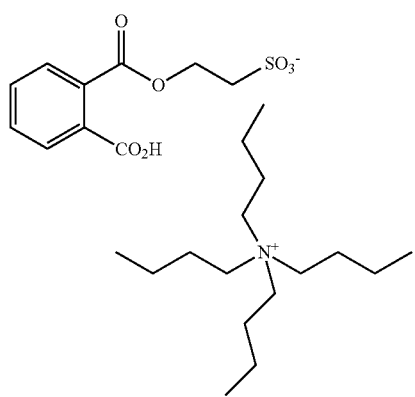
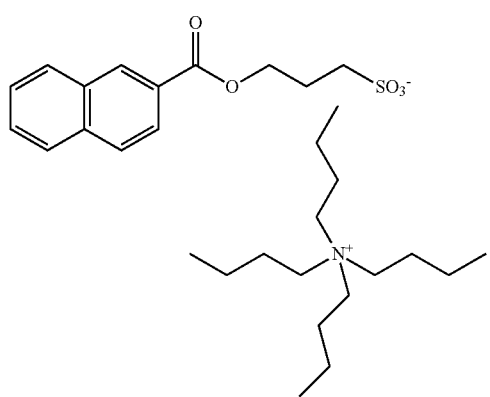
116
-continued
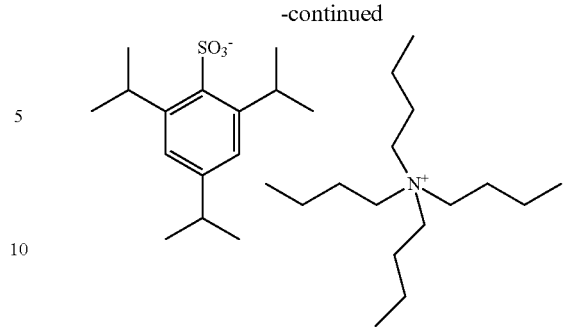
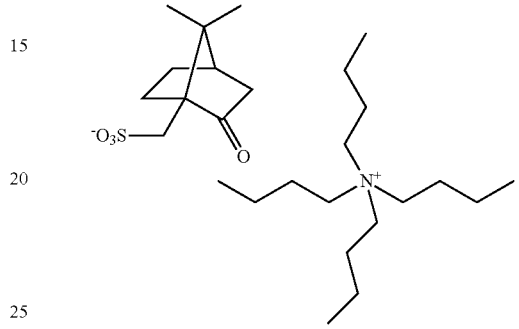
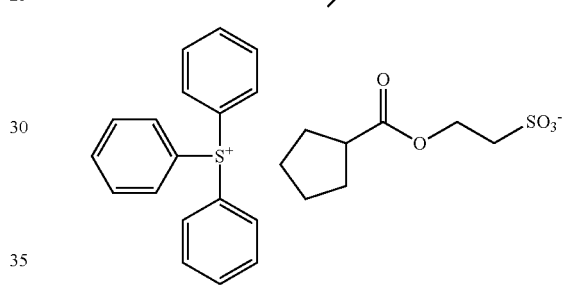
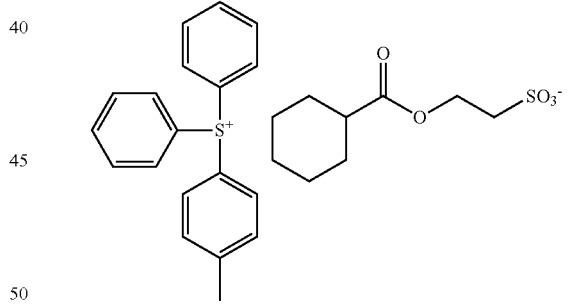
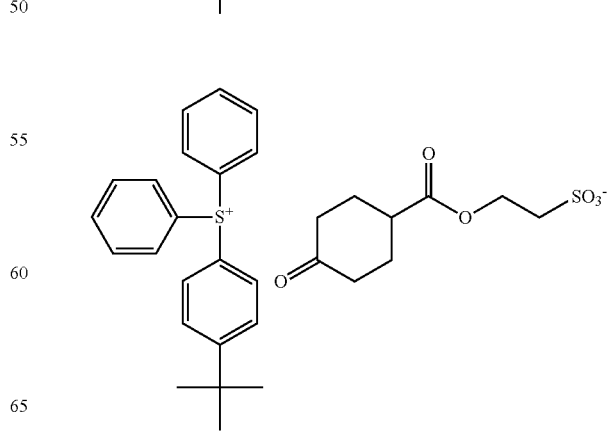

117
-continued
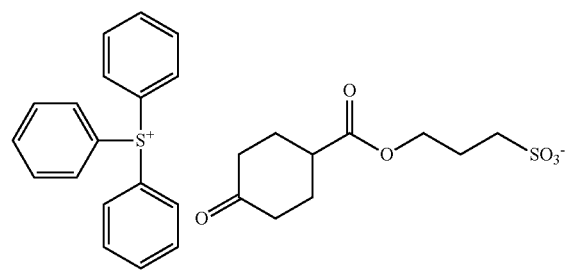
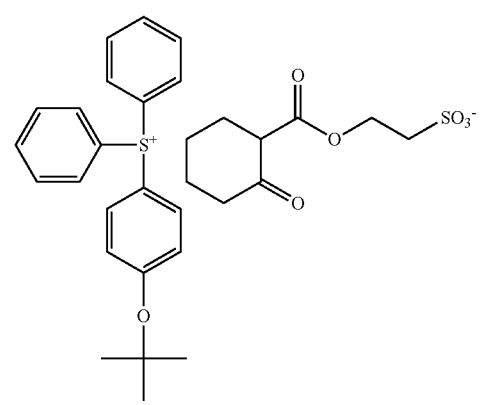
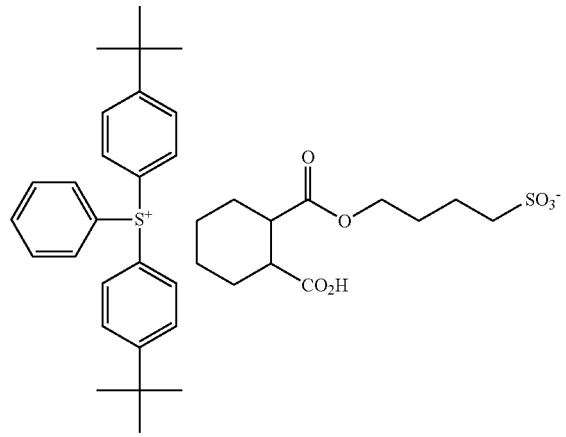
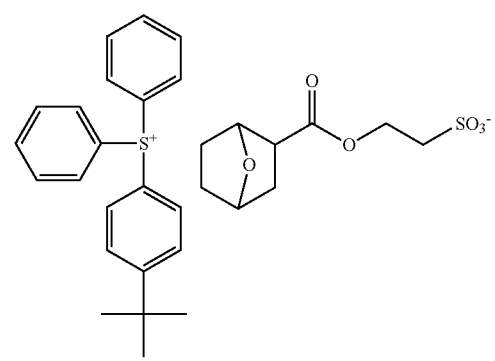
118
-continued
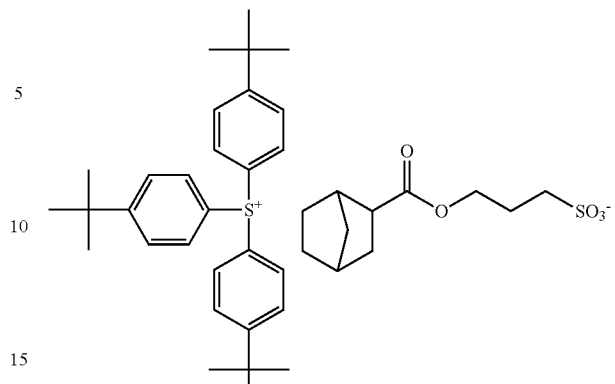
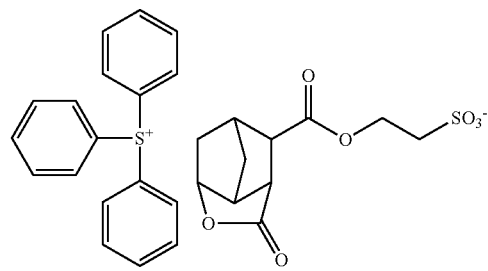
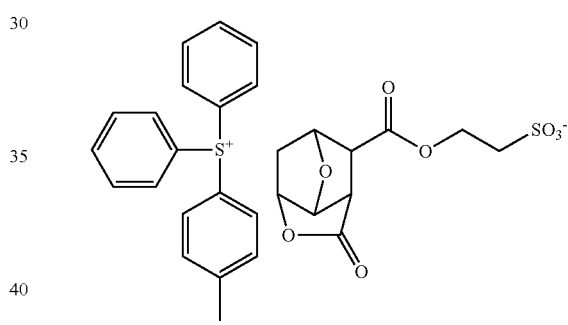
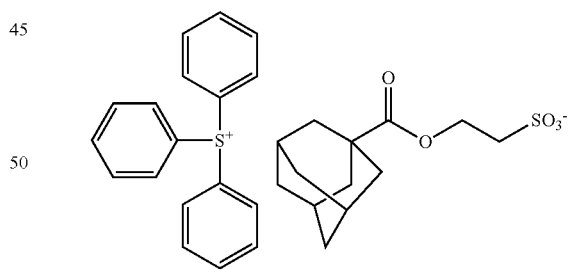
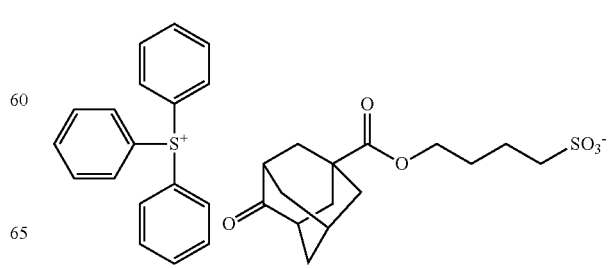

119
-continued
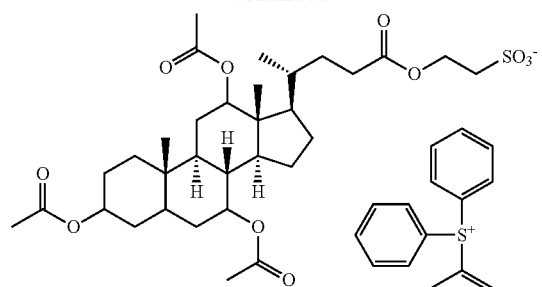
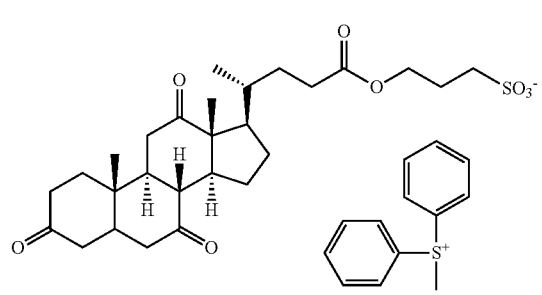
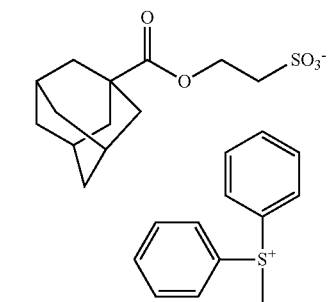
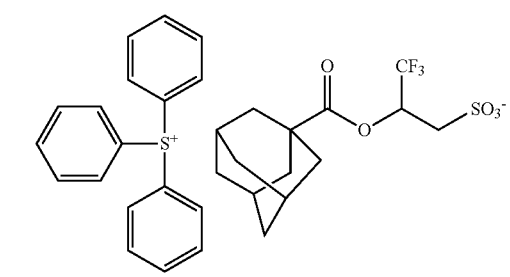
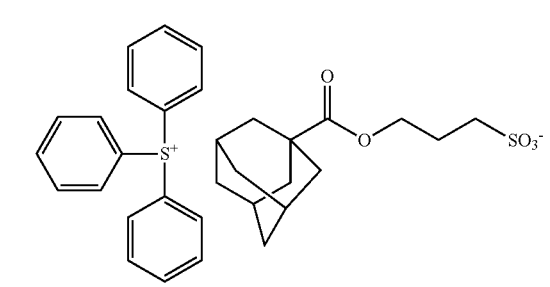
120
-continued
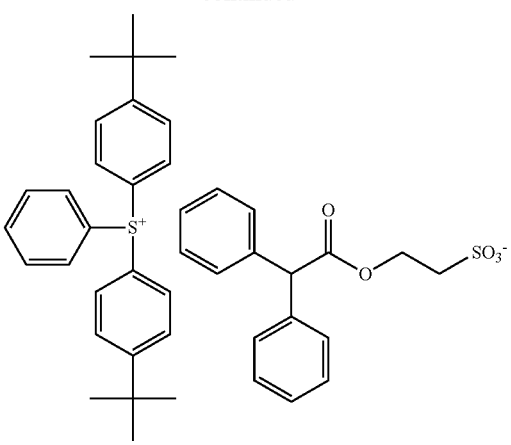
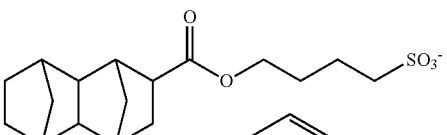
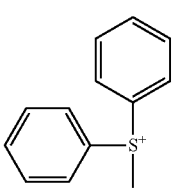
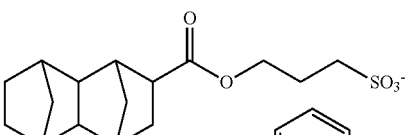
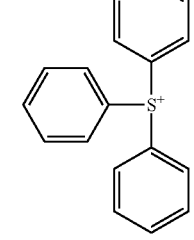

121
-continued
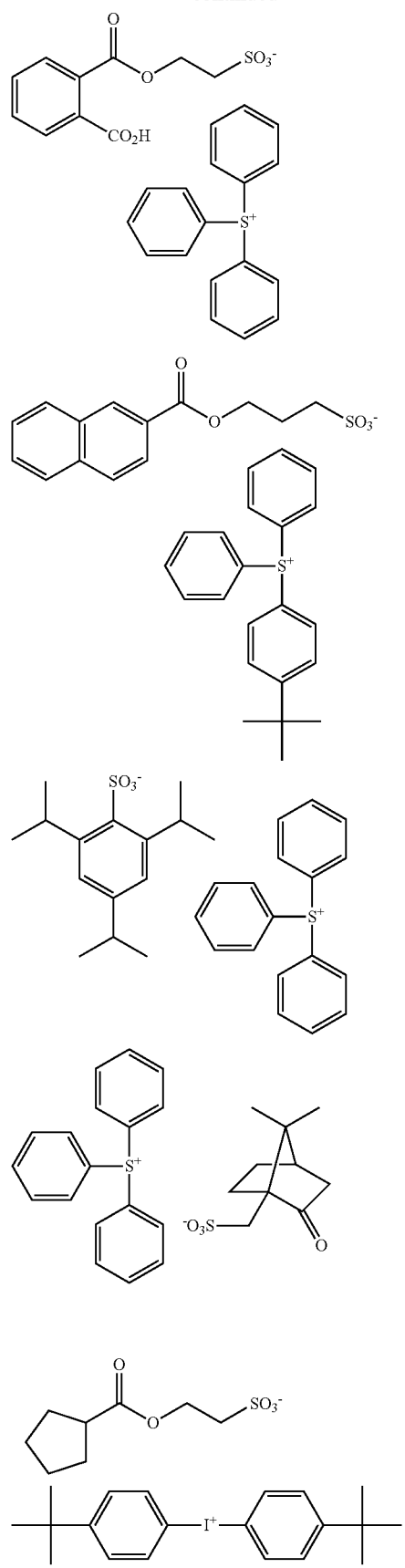
122
-continued
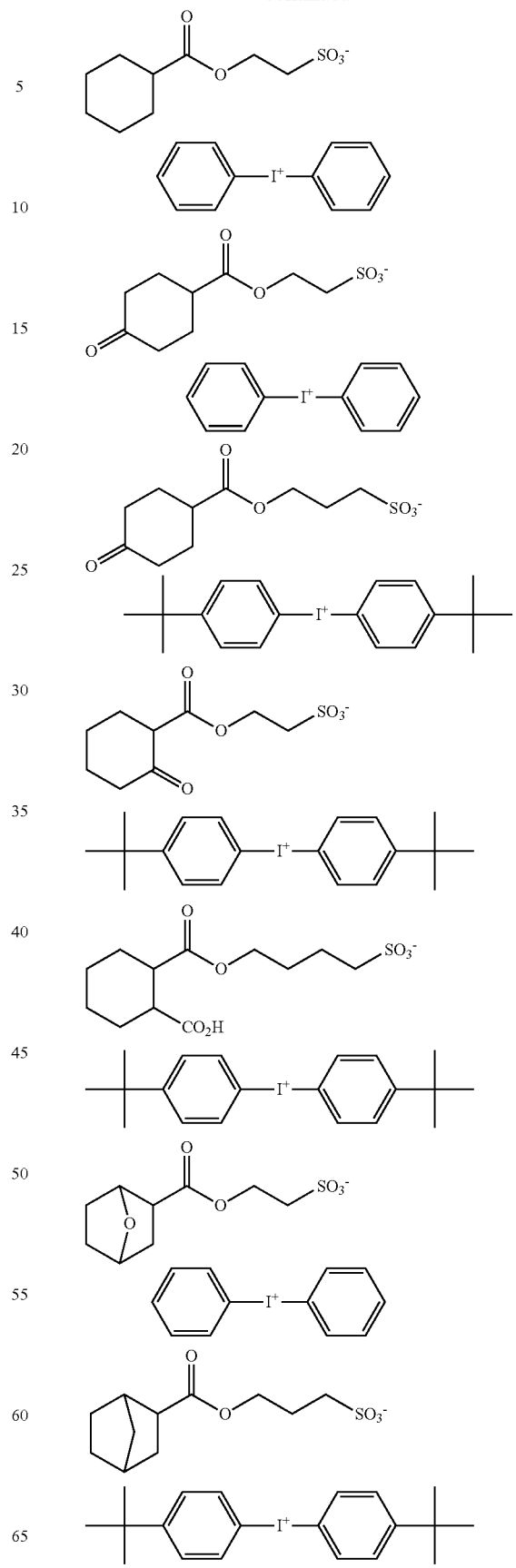

123
-continued
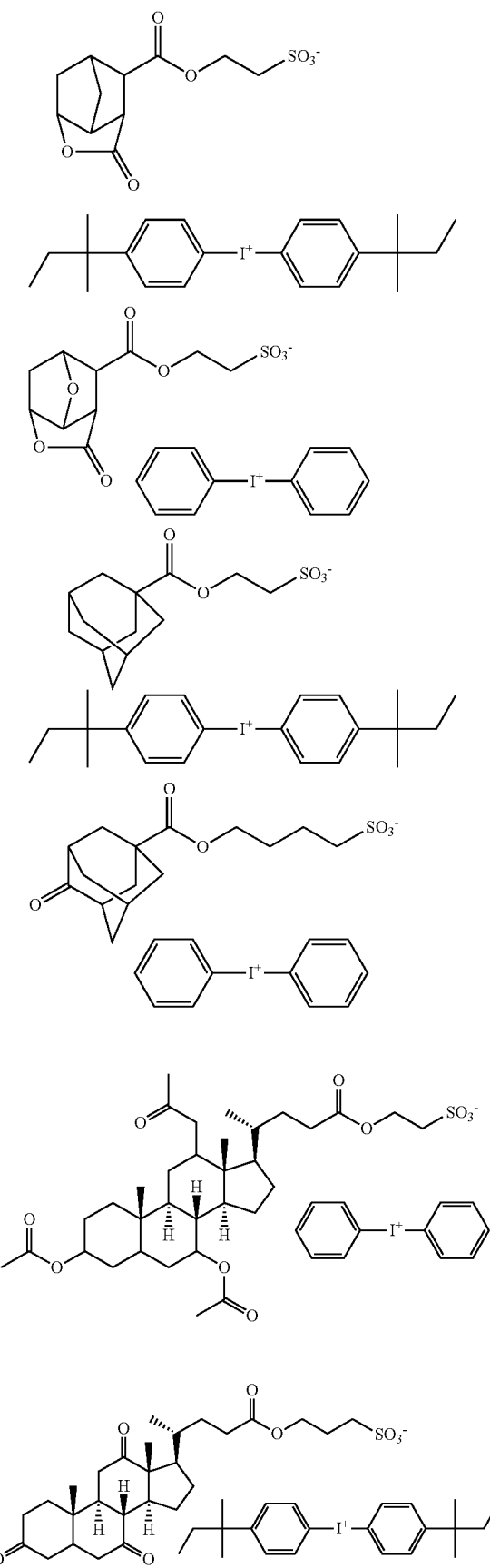
124
-continued
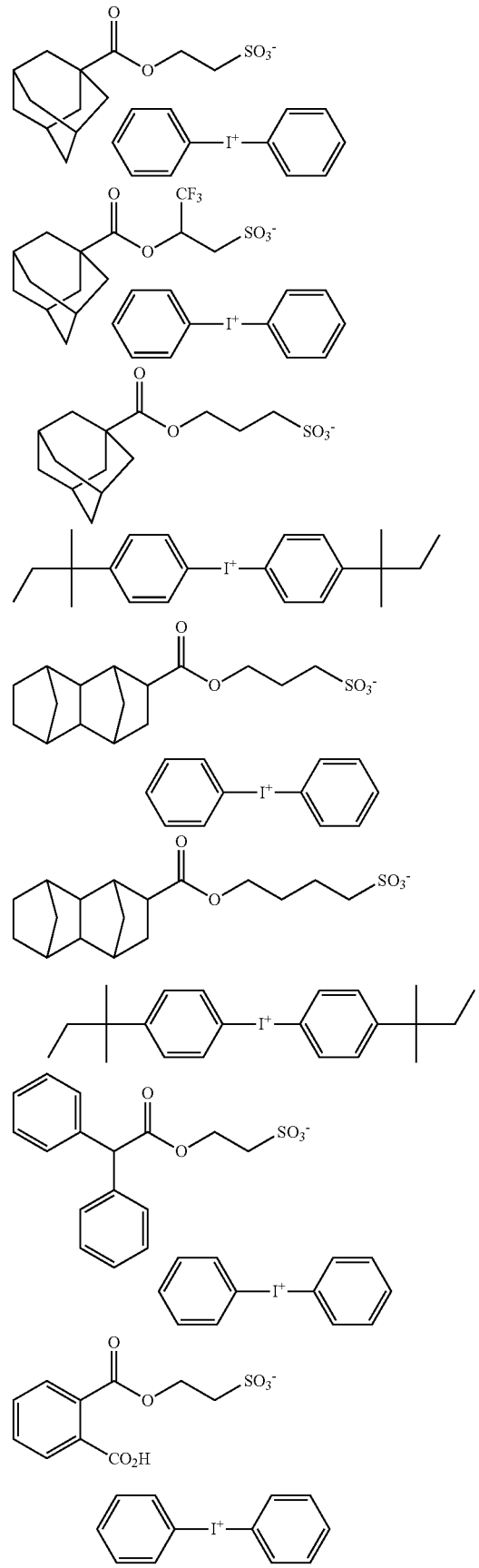

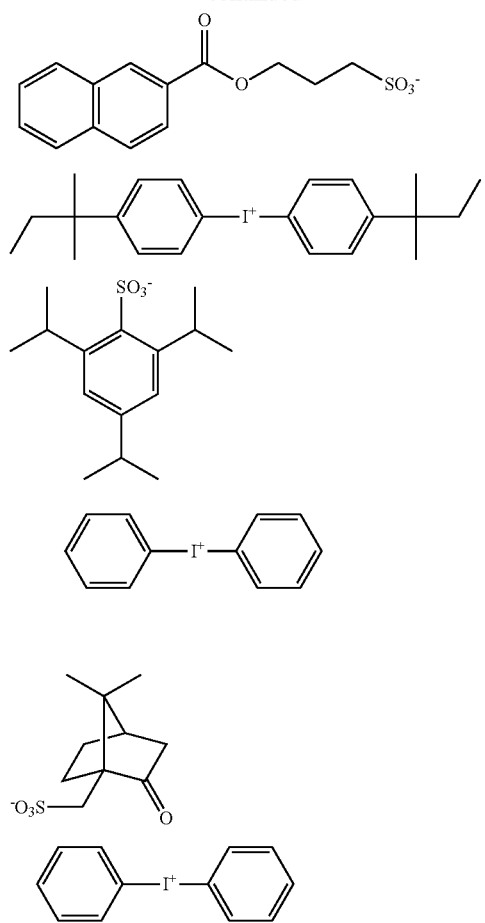
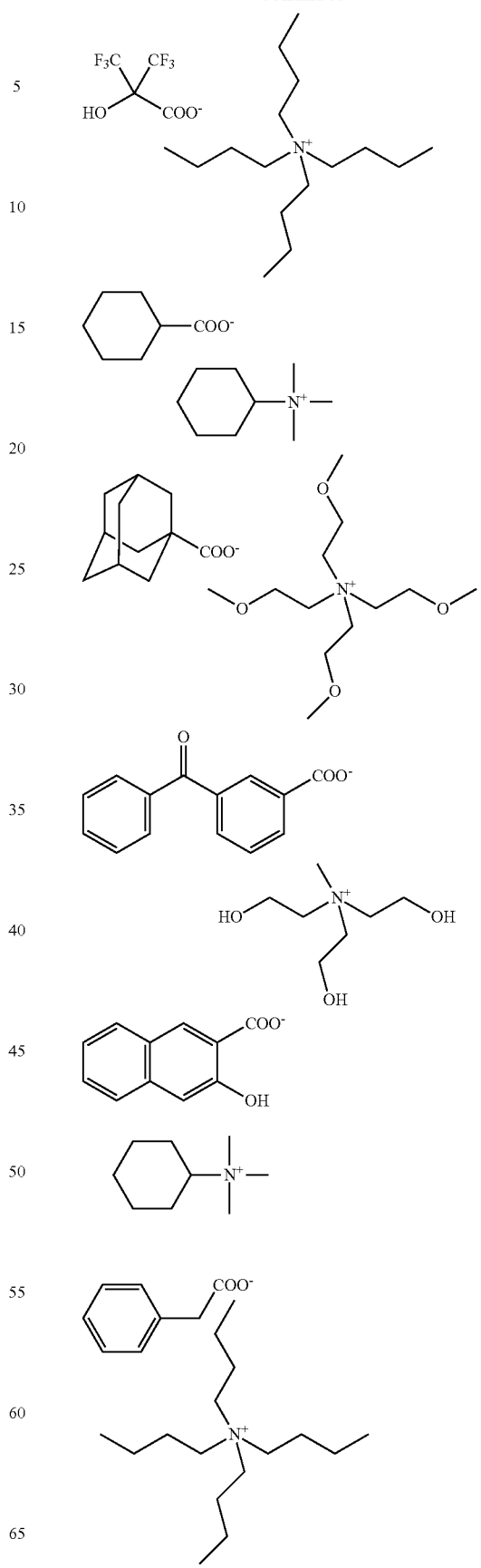

127
-continued
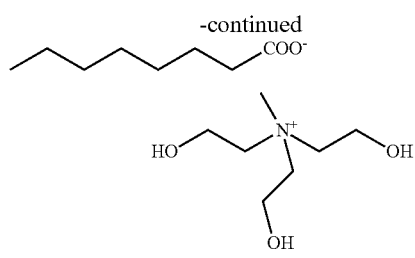
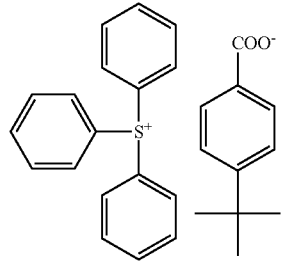
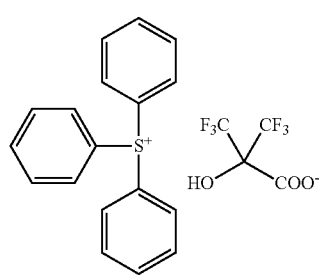
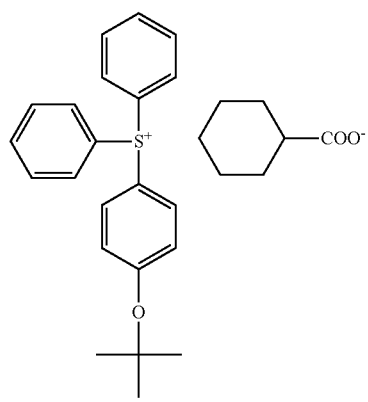
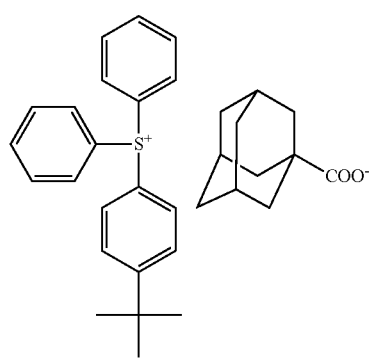
128
-continued
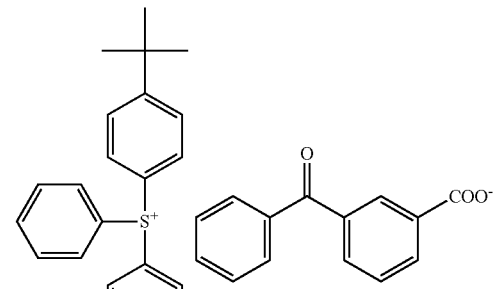
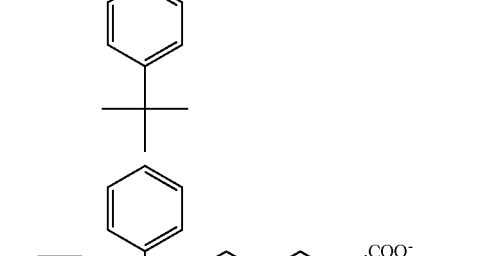
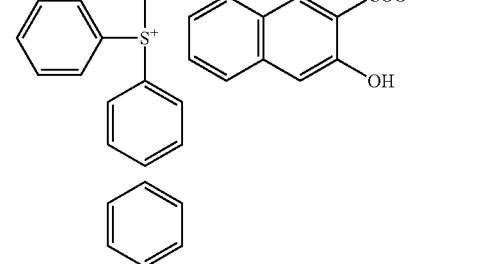
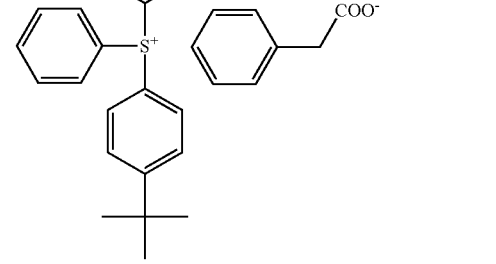
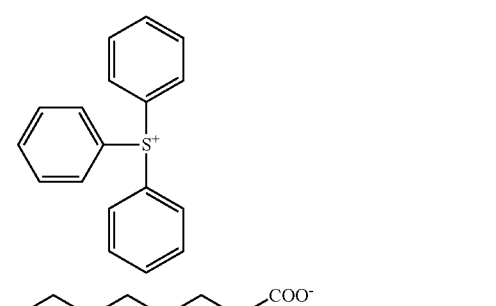
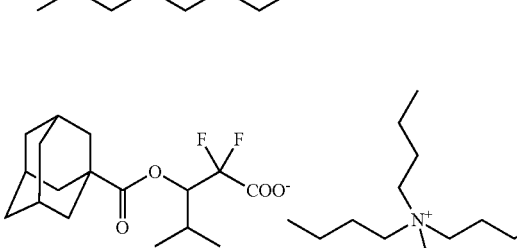

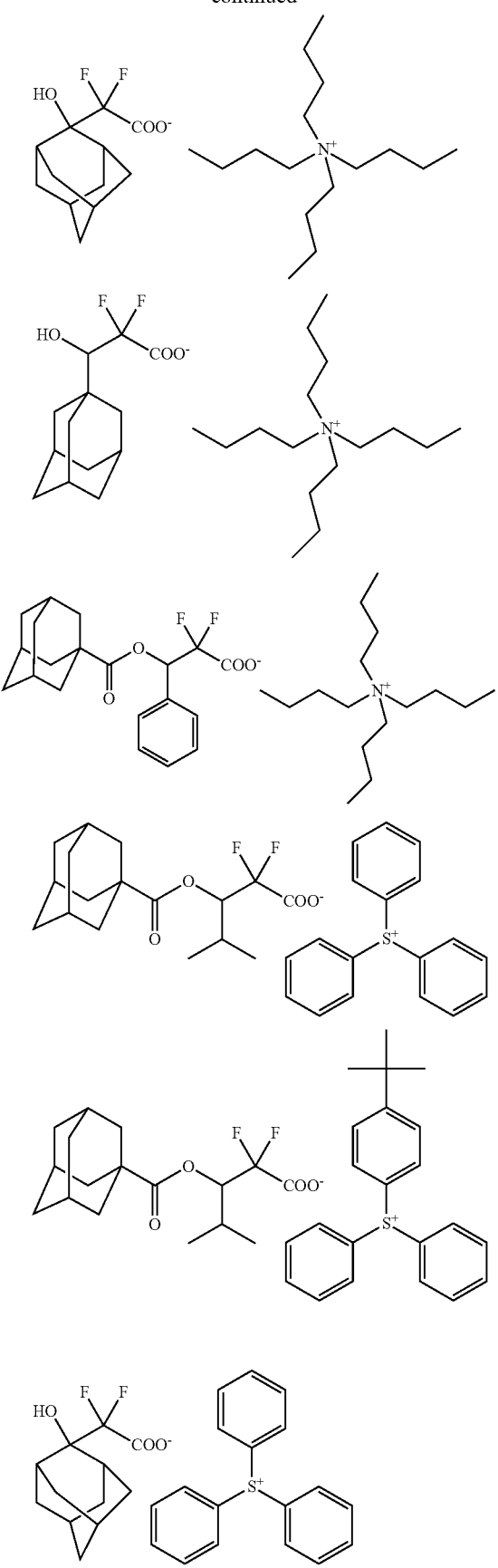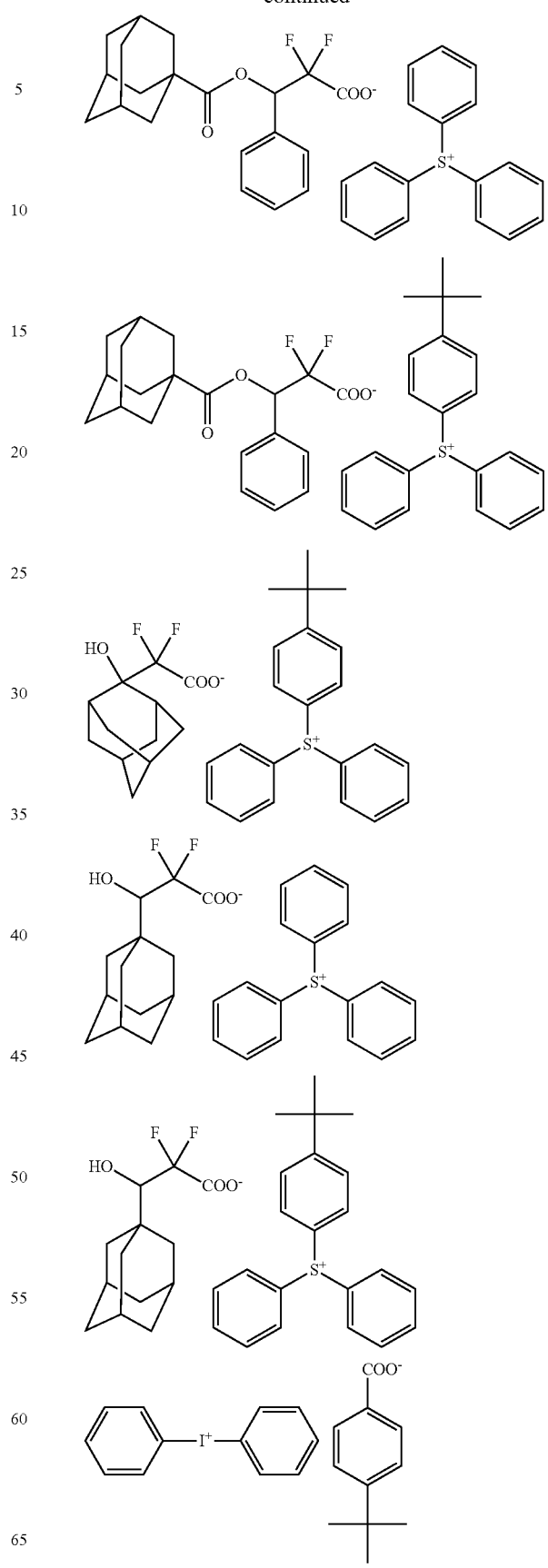

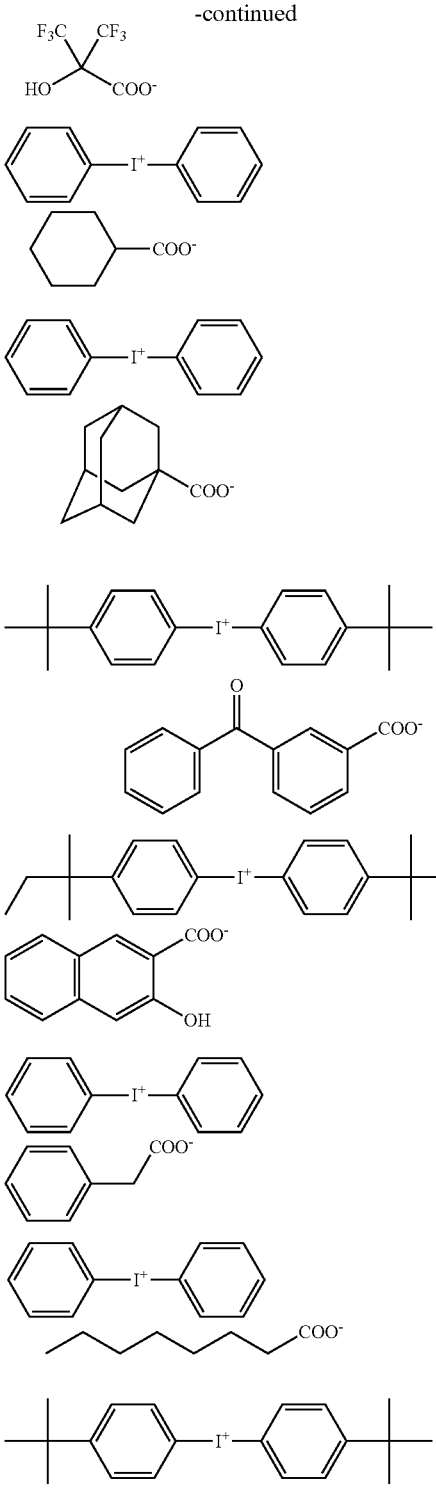

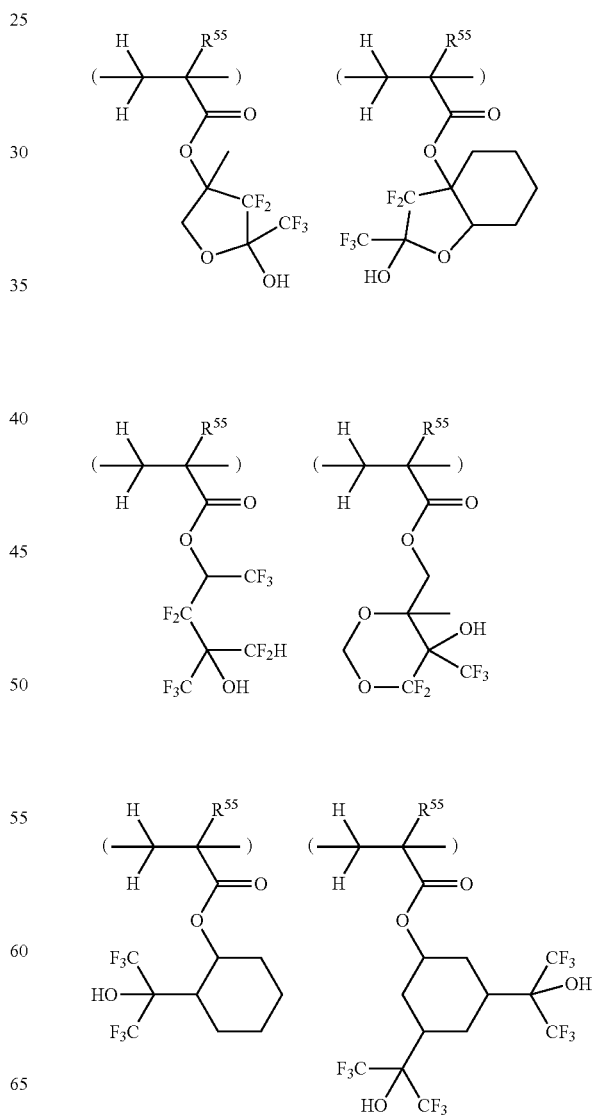

Exemplary surfactants are described in JP-A 2008-111103, paragraphs [0165] to [0166]. Exemplary dissolution regulators are described in JP-A 2008-122932 (US 2008090172), paragraphs [0155] to [0178], and exemplary acetylene alcohols in paragraphs [0179] to [0182].

Notably, an appropriate amount of the organic solvent used is 50 to 10,000 parts, preferably 100 to 5,000 parts by weight, an appropriate amount of the dissolution regulator is 0 to 50 parts, preferably 0 to 40 parts by weight, and an appropriate amount of the basic compound is 0 to 100 parts, preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. This water repellency improver may be used in the topcoatless immersion lithography. These water repellency improvers have a specific structure with a 1,1,1,3,3,3-hexafluoro-2-propanol residue and are described in JP-A 2007-297590, JP-A 2008-111103, JP-A 2008-122932, JP-A 2012-128067, and JP-A 2013-057836.

The water repellency improver is described in more detail. Preferred are a homopolymer consisting of fluorine-containing units of one type, a copolymer consisting of fluorine-containing units of more than one type, and a copolymer consisting of fluorine-containing units and other units. Suitable fluorine-containing units and other units are shown below, but not limited thereto. Notably $R^{55}$ is hydrogen or methyl.

-continued
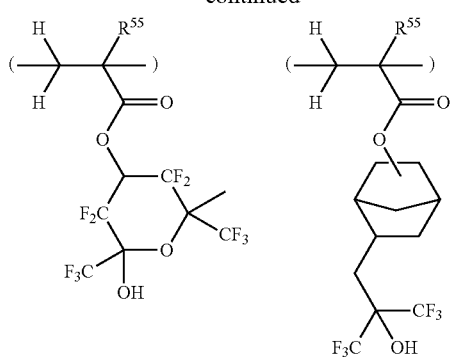
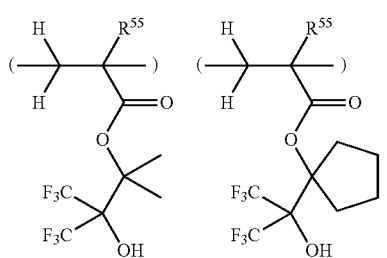
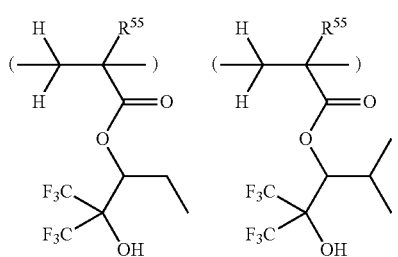
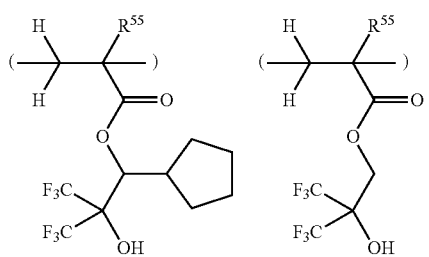
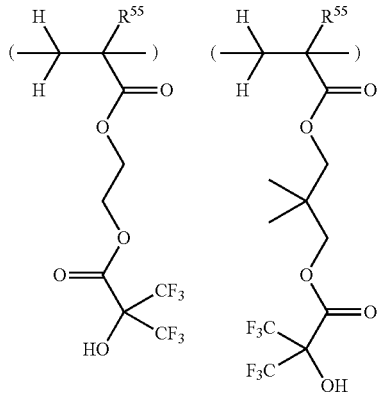
-continued
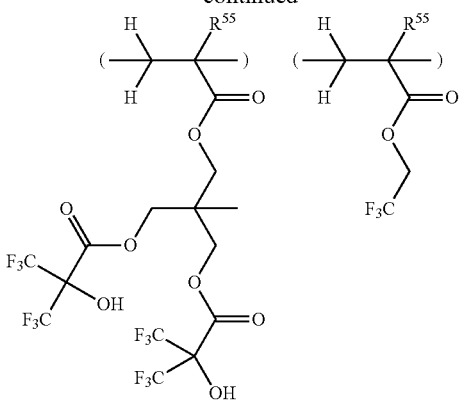
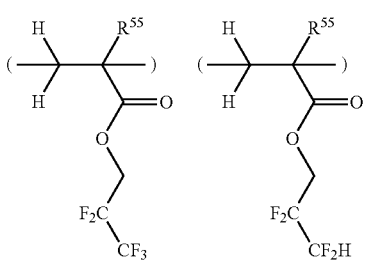
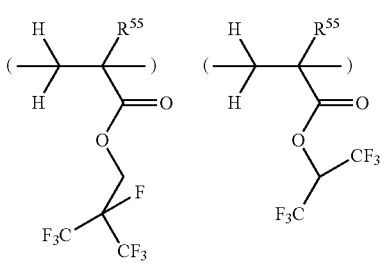
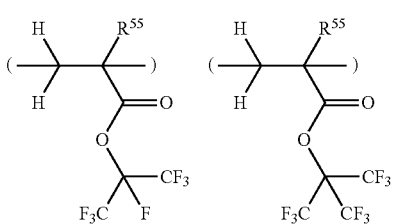
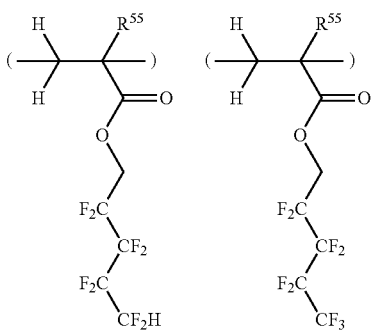

135
-continued
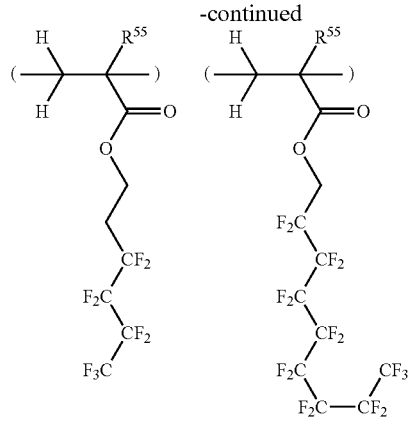
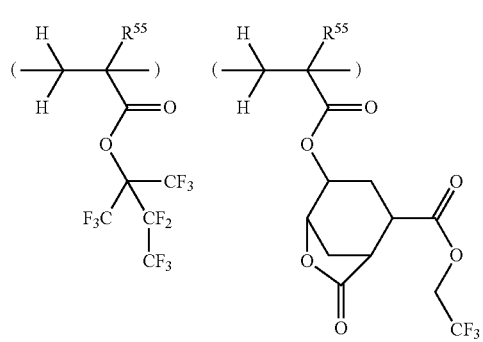
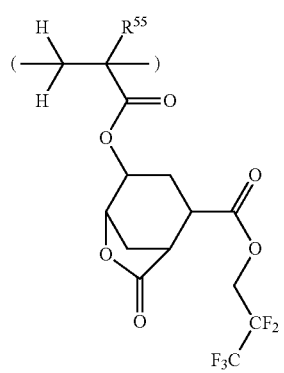
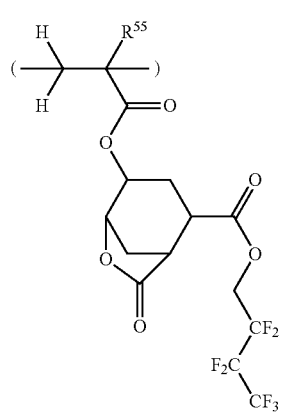
136
-continued
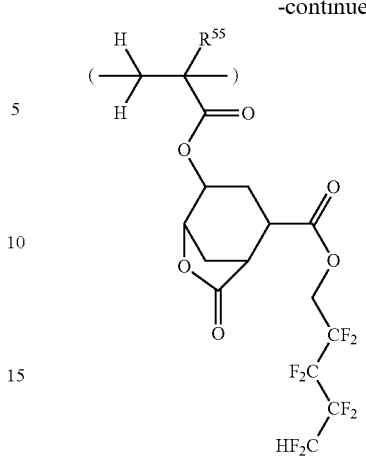
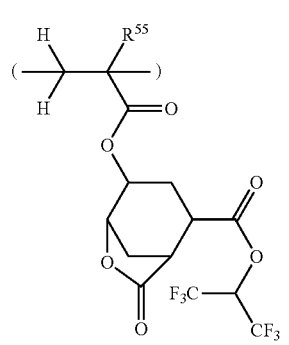
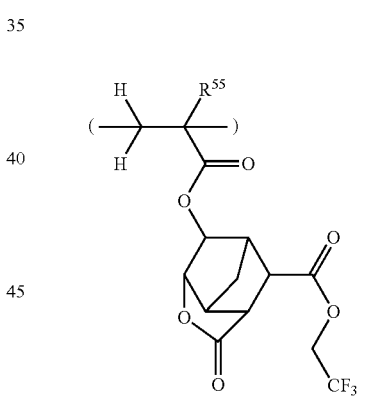
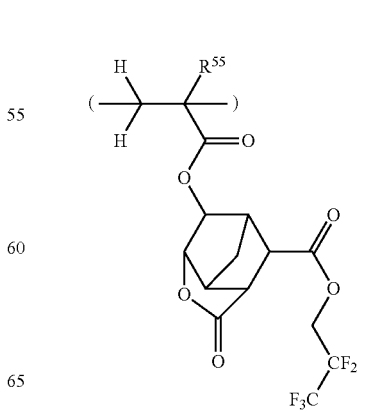

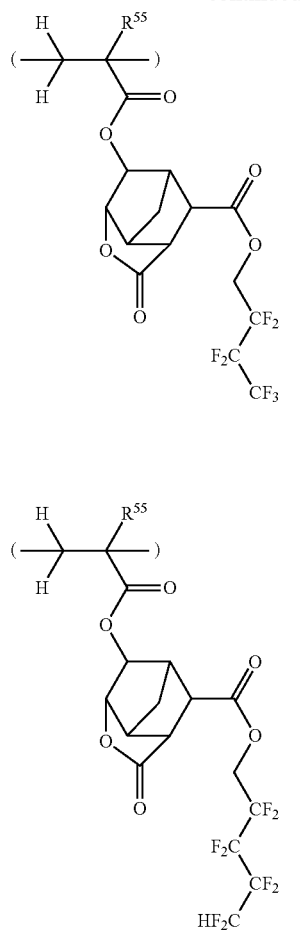
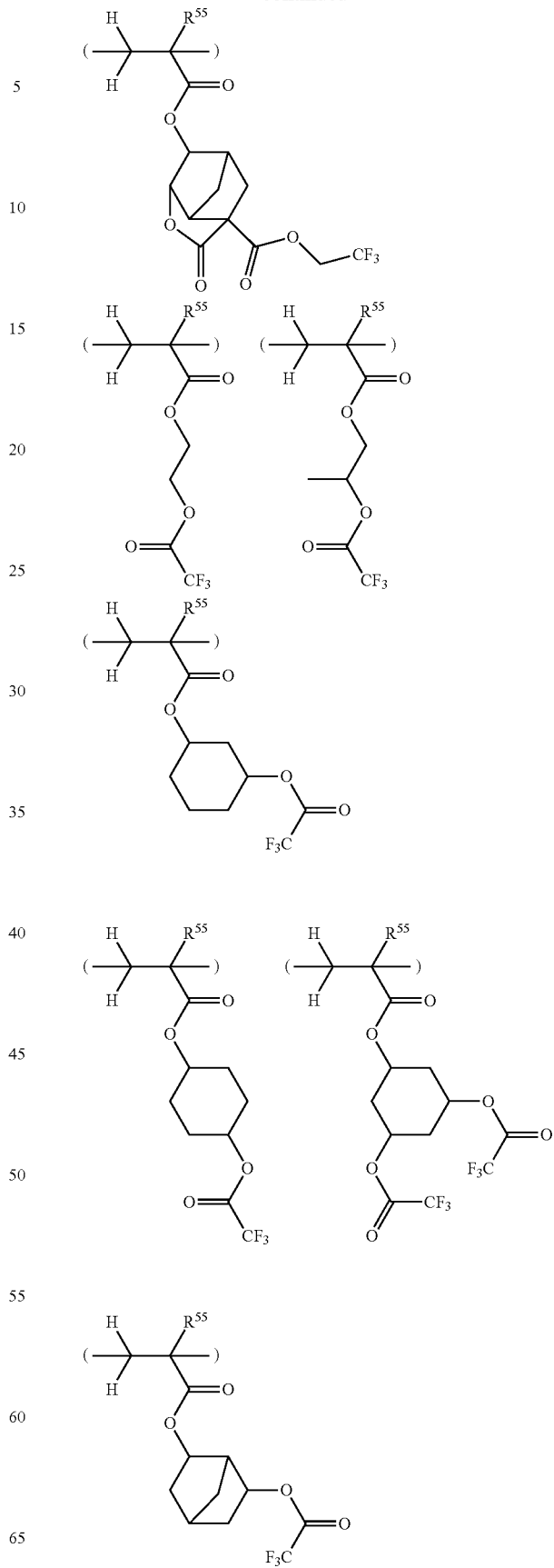

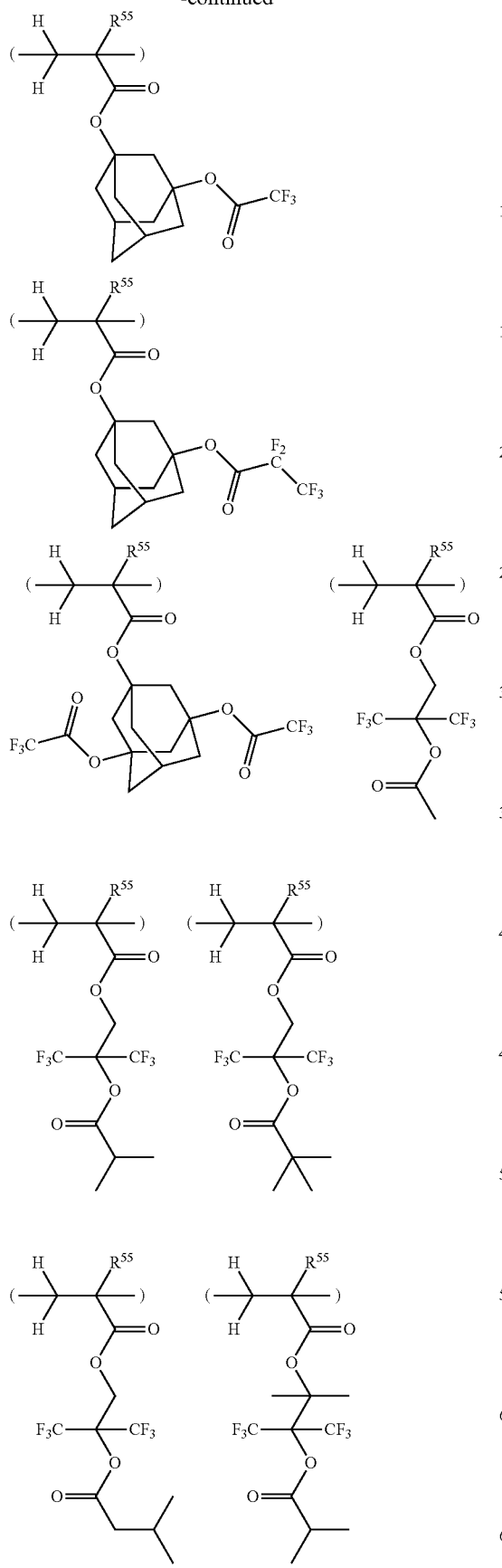
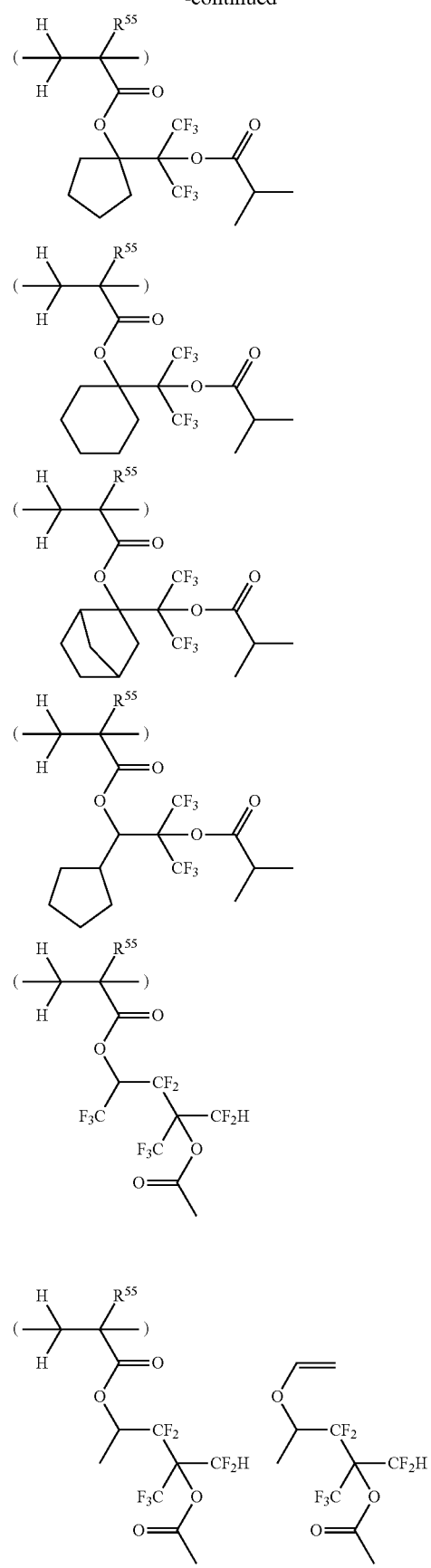

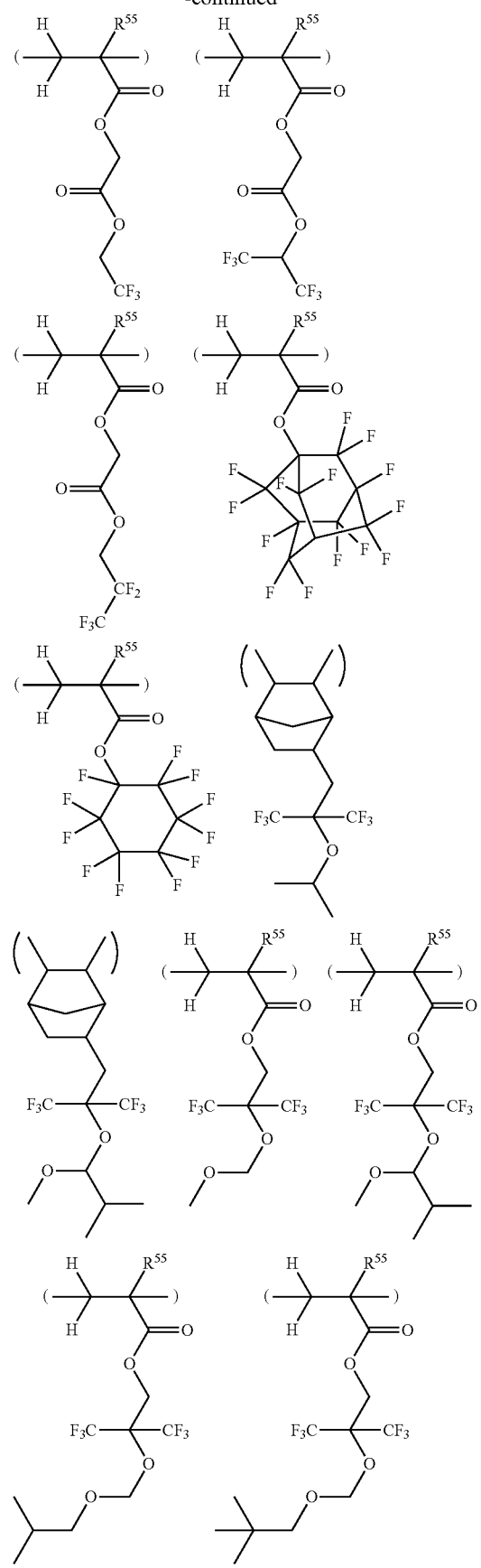
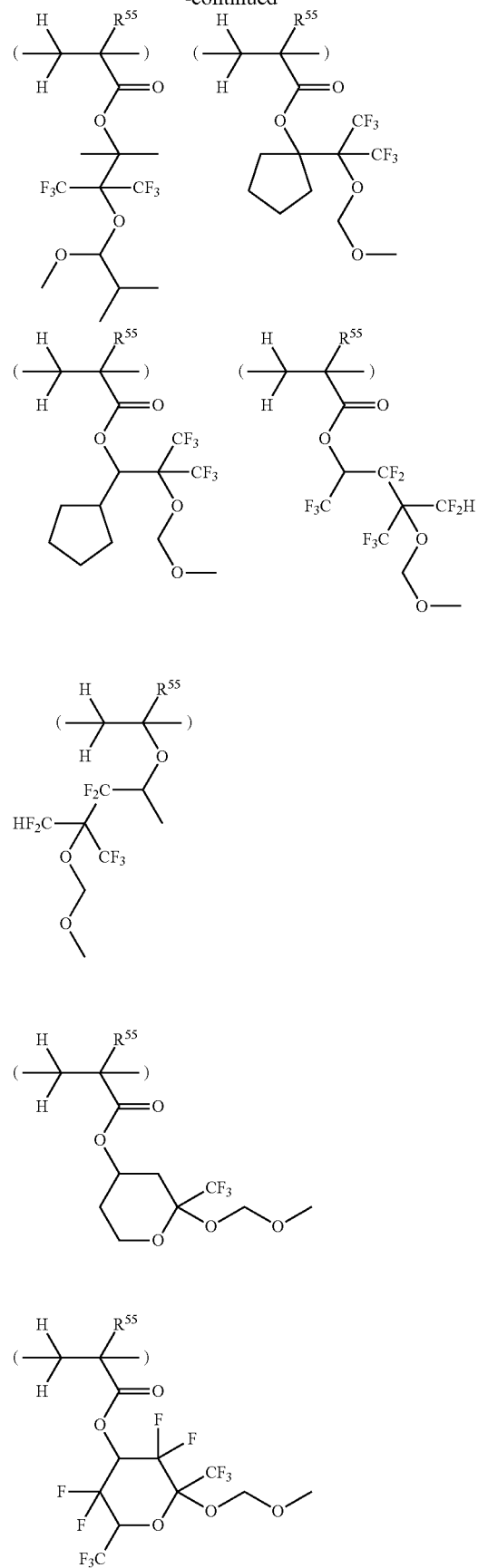

143
-continued
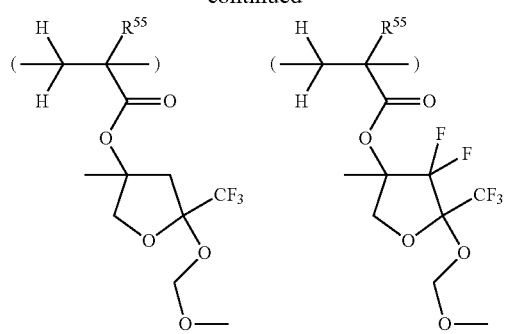
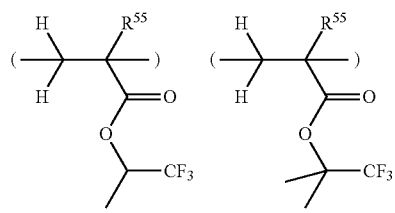
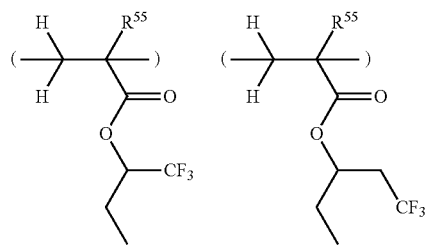
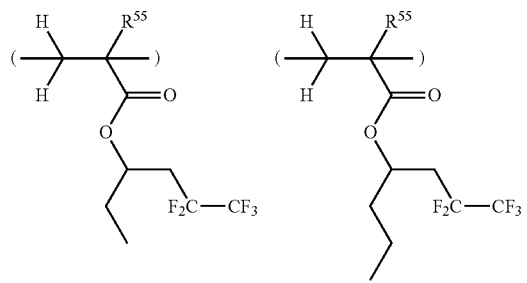
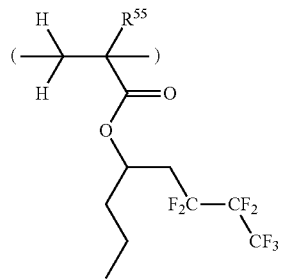
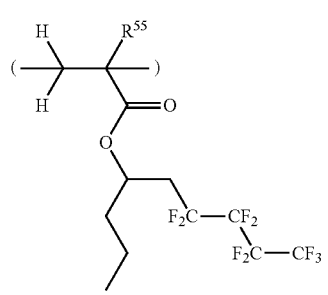
144
-continued
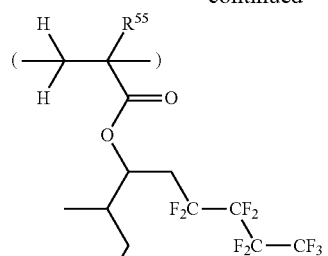
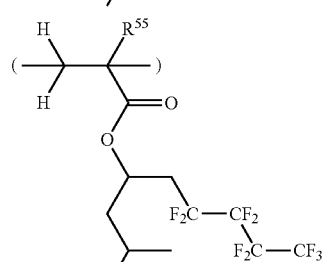
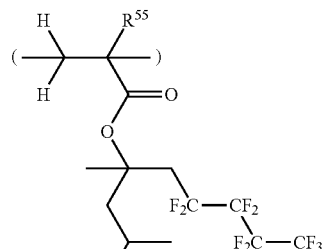
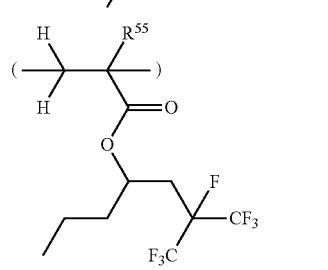
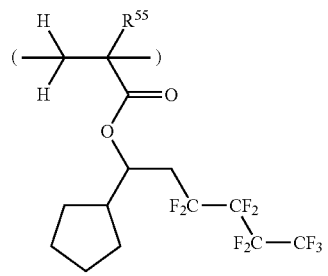
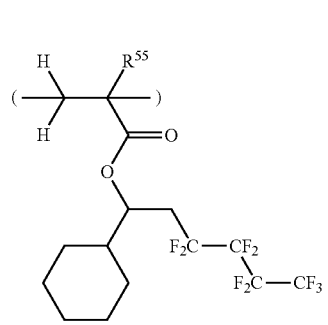

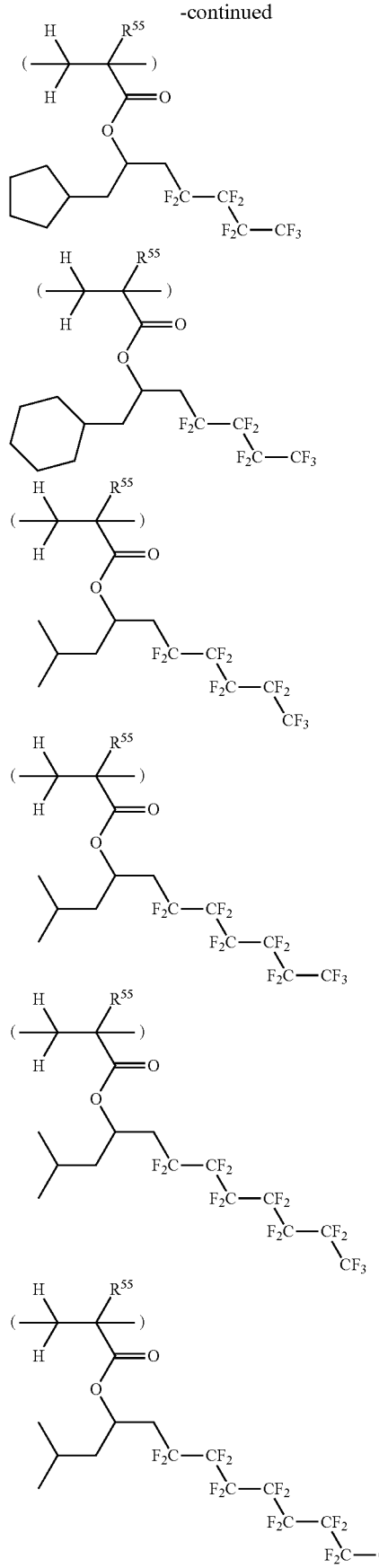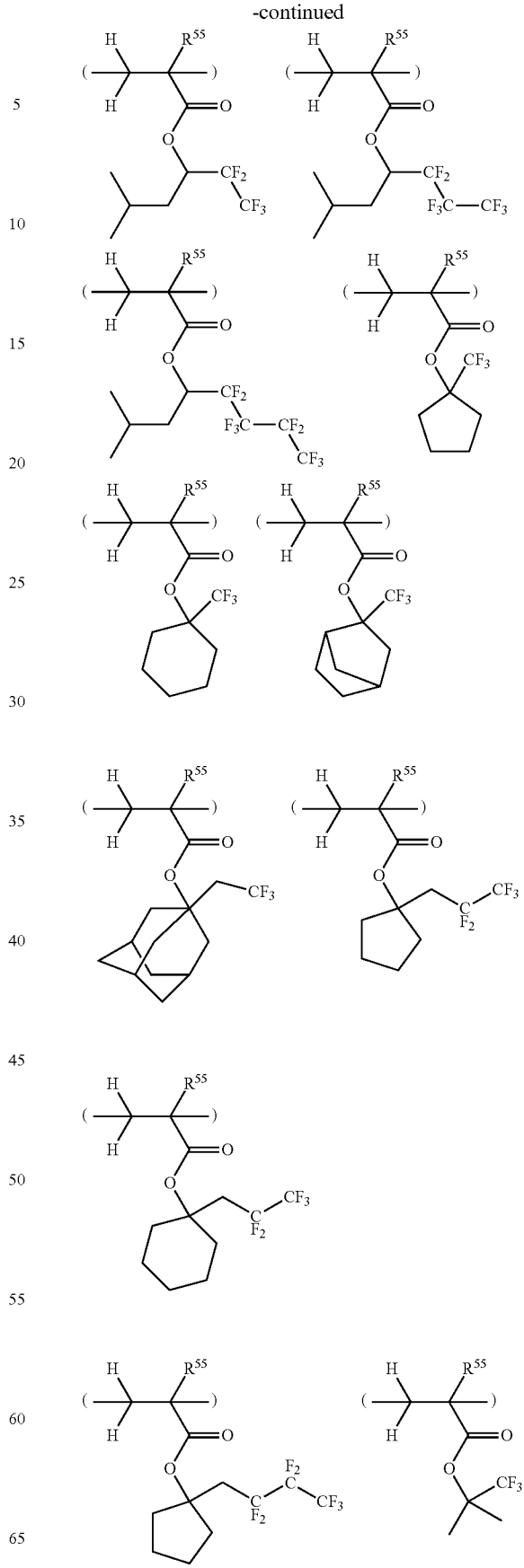

-continued

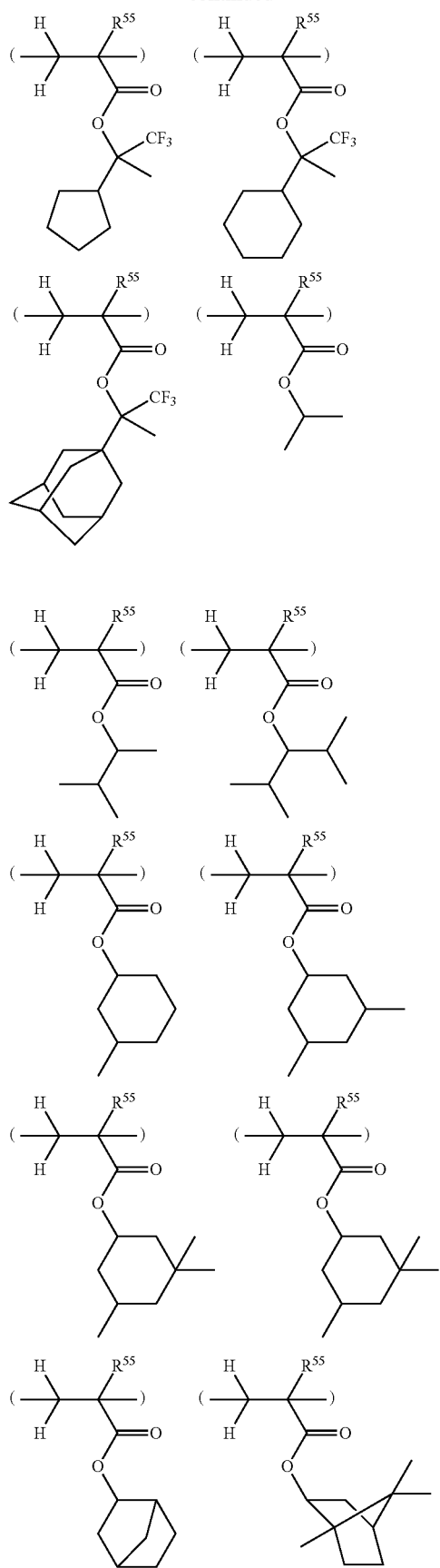
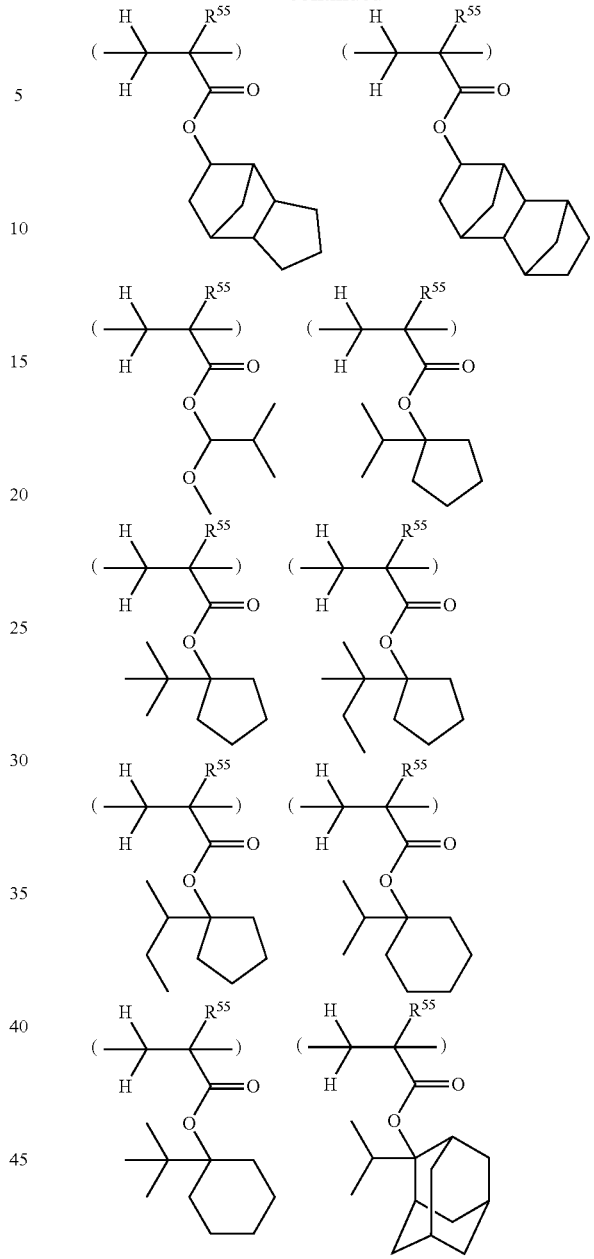

The water repellency improver to be added to the resist composition should be soluble in alkaline aqueous solution as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, any hole pattern opening failure after development, and bridging of a line-and-space pattern. An appropriate amount of the water repellency improver is 0.1 to 20 parts, preferably 0.5 to 10 parts by weight per 100 parts by weight of the base resin.

Though not essential, a crosslinker may be added to the resist composition to facilitate formation of a negative pattern via a polarity switch of the inventive polymer. Suitable crosslinkers are described in JP-A 2006-145755. The crosslinker is preferably used in such an amount as not to interfere with high resolution performance by a polarity switch and solubility change induced by dehydration reaction of the recurring unit derived from the inventive monomer. An appropriate amount of the crosslinker is 1 to 30 parts, preferably 3 to 20 parts by weight per 100 parts by weight of the base resin.

Process

The resist composition comprising the inventive polymer, typically chemically amplified resist composition comprising the inventive polymer, optionally a basic compound and an acid generator, in an organic solvent is used in the fabrication of various integrated circuits. Pattern formation using the resist composition may be performed by well-known lithography processes. The process generally involves coating, prebaking, exposure, PEB, and development. If necessary, any additional steps may be added.

The negative resist composition is first applied onto a substrate on which an integrated circuit is to be formed (e.g., Si, $SiO_2$, SiN, SiON, TiN, WSi, BPSG, SOG, or a multilayer film including silicon-containing antireflective coating or organic hydrocarbon film) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2.0 µm thick.

The resist film is then exposed to a desired pattern of high-energy radiation such as UV, deep-UV, EB, EUV (soft x-ray), x-ray, excimer laser light, γ-ray, or synchrotron radiation, directly or through a mask. The exposure dose is preferably about 1 to 200 mJ/cm$^2$, more preferably about 10 to 100 mJ/cm$^2$, or about 0.1 to 100 µC/cm$^2$, more preferably about 0.5 to 50 µC/cm$^2$. The resist film is further baked (PEB) on a hot plate preferably at 60 to 150° C. for 10 seconds to 30 minutes, more preferably at 80 to 120° C. for 30 seconds to 20 minutes.

Thereafter the resist film is developed in an alkaline developer for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is not dissolved in the developer whereas the resist film in the unexposed region is dissolved. In this way, the desired negative pattern is formed on the substrate. After the development step, the patterned resist film is rinsed with water, preferably for 3 seconds to 3 minutes, more preferably 5 seconds to 2 minutes, by conventional techniques such as dip, puddle and spray techniques. It is appreciated that the resist composition of the invention is best suited for micro-patterning using such high-energy radiation as KrF and ArF excimer laser, EB, EUV (soft x-ray), x-ray, γ-ray and synchrotron radiation.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight. For all polymers, Mw and Mn are determined versus polystyrene standards by GPC using tetrahydrofuran solvent, and dispersity Mw/Mn is computed therefrom.

[1] Synthesis of Monomers

Example 1

Synthesis of Monomer 1

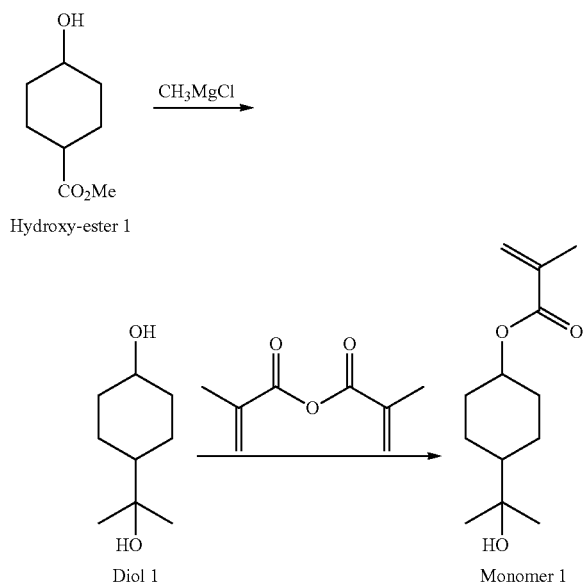

Example 1-1

Synthesis of Diol 1

In nitrogen atmosphere, a solution of 95 g of Hydroxy-ester 1 (cis/trans-isomer=75/25) in 200 mL of tetrahydrofuran (THF) was added dropwise to 2,400 mL of a THF solution of 1.0 mol/L methylmagnesium chloride at 25-45° C. The contents were stirred at 50° C. for 10 hours. Then the reaction solution was ice cooled, to which a mixture of 240 g of ammonium chloride and 2,000 g of a 2.4 wt % hydrochloric acid aqueous solution was added dropwise to quench the reaction. This was followed by ordinary aqueous workup, solvent distillation, and vacuum distillation, obtaining 79 g of Diol 1 (yield 83%, cis/trans-isomer=73/27). It is noted that after the distillation, the distillate gradually solidified into white crystals at room temperature.

Analytical data of the compound are shown below. FIG. 1 shows a proton nuclear magnetic resonance ($^1$H-NMR) spectrum of the compound.

boiling point (b.p.): 90° C./20 Pa
IR (D-ATR): ν=3292, 2969, 2933, 2859, 1464, 1435, 1377, 1367, 1336, 1305, 1265, 1229, 1203, 1150, 1067, 1037, 998, 967, 951, 934, 910, 875, 843, 809, 768, 697, 665, 615, 601, 588 cm$^{-1}$

Example 1-2

Synthesis of Monomer 1

In nitrogen atmosphere, 84 g of methacrylic anhydride was added dropwise to a solution of 70 g of Diol 1 and 69 g of triethylamine in 300 mL of THF at room temperature. The contents were stirred at 40° C. for 5 hours. Then the reaction solution was ice cooled, to which 300 mL of a saturated aqueous solution of sodium hydrogencarbonate was added dropwise to quench the reaction. This was followed by ordinary aqueous workup, solvent distillation, and vacuum distillation, obtaining 100 g of Monomer 1 (yield 90%, cis/trans-isomer=75/25).

Figure 2:
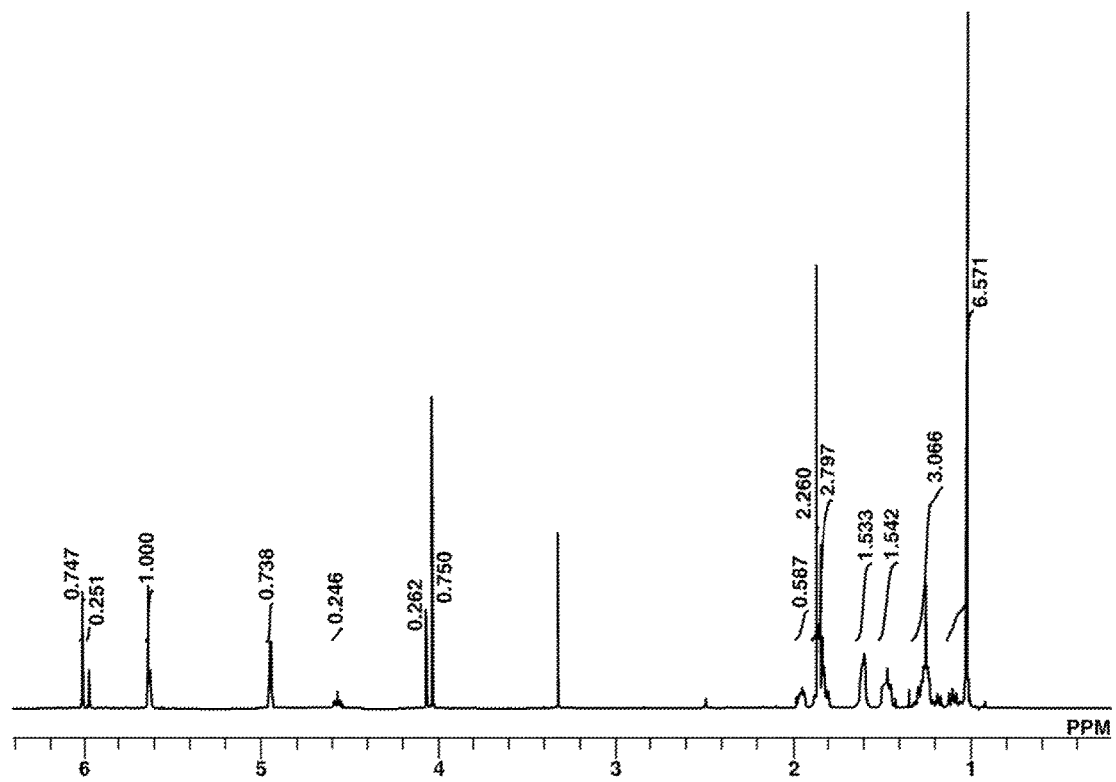
FIG. 2 is a diagram showing $^1$H-NMR spectrum of Monomer 1 in Example 1-2.

Analytical data of the target compound are shown below. FIG. 2 shows a $^1$H-NMR spectrum of the compound.

b.p.: 83° C./5 Pa

IR (D-ATR): v=3514, 2944, 2866, 1715, 1637, 1448, 1403, 1379, 1361, 1317, 1296, 1179, 1099, 1037, 1025, 1011, 935, 907, 841, 815, 768, 653, 594 cm$^{-1}$

Example 2

Synthesis of Monomer 2

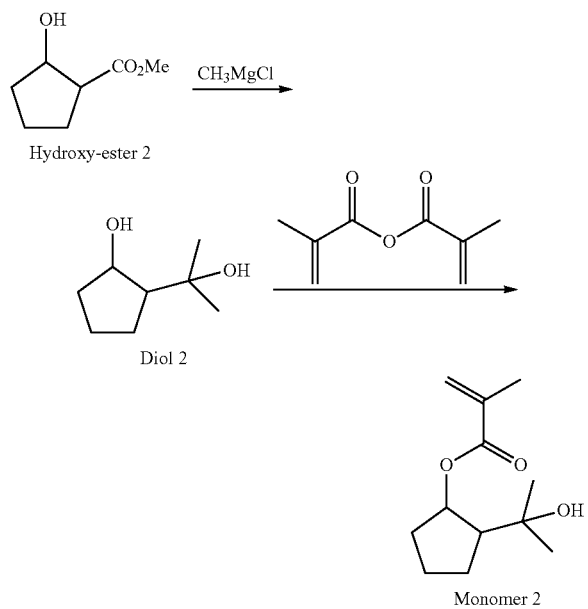

Example 2-1

Synthesis of Diol 2

In nitrogen atmosphere, a solution of 87 g of Hydroxy-ester 2 (isomer mixture) in 200 mL of THF was added dropwise to 2,400 mL of a THF solution of 1.0 mol/L methylmagnesium chloride at 25-45° C. The contents were stirred at 50° C. for 10 hours. Then the reaction solution was ice cooled, to which a mixture of 240 g of ammonium chloride and 2,000 g of a 2.4 wt % hydrochloric acid aqueous solution was added dropwise to quench the reaction. This was followed by ordinary aqueous workup and solvent distillation, obtaining 91 g of Diol 2 crude product. This crude product was used in the subsequent step without purification.

Example 2-2

Synthesis of Monomer 2

In nitrogen atmosphere, 83 g of methacrylic anhydride was added dropwise to a solution of 91 g of Diol 2 crude product and 68 g of triethylamine in 300 mL of THF at room temperature. The contents were stirred at 40° C. for 5 hours. Then the reaction solution was ice cooled, to which 300 mL of a saturated aqueous solution of sodium hydrogencarbonate was added dropwise to quench the reaction. This was followed by ordinary aqueous workup, solvent distillation, and vacuum distillation, obtaining 92 g of Monomer 2 (two-step yield 72%, isomer ratio=56/44).

Figure 3:
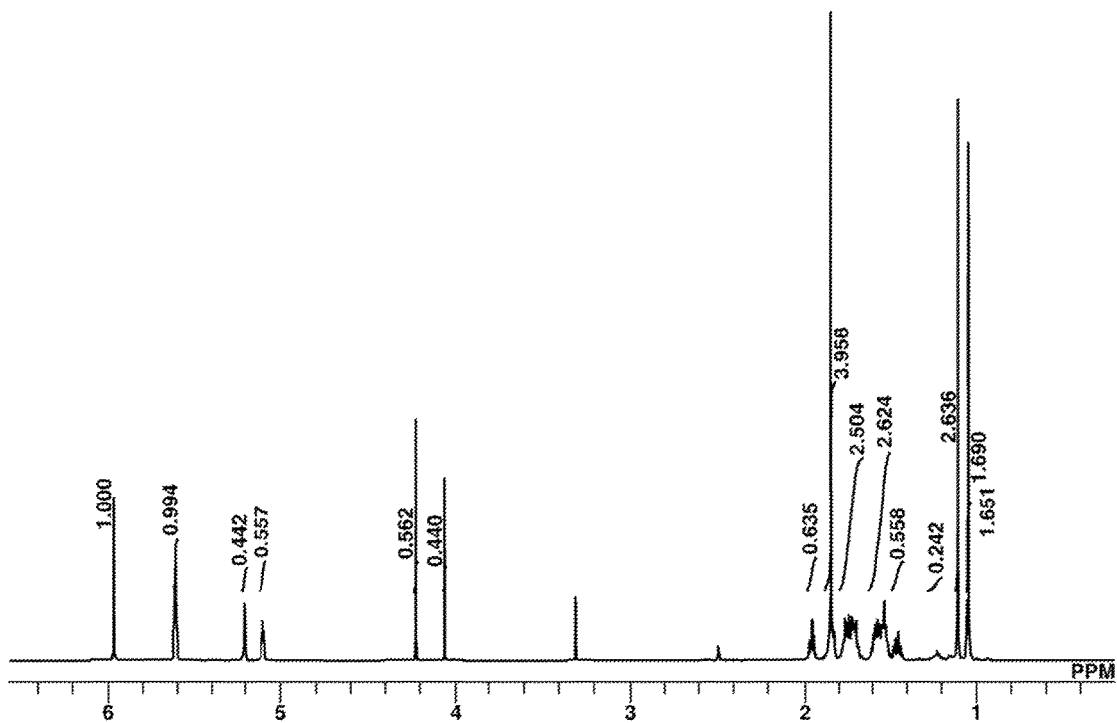
FIG. 3 is a diagram showing $^1$H-NMR spectrum of Monomer 2 in Example 2-2.

Analytical data of the target compound are shown below. FIG. 3 shows a $^1$H-NMR spectrum of the compound.

b.p.: 68° C./4 Pa

IR (D-ATR): v=3475, 2969, 2875, 1715, 1635, 1452, 1402, 1377, 1323, 1298, 1159, 1010, 940, 846, 815, 651, 596, 564 cm$^{-1}$

Example 3

Synthesis of Monomer 3

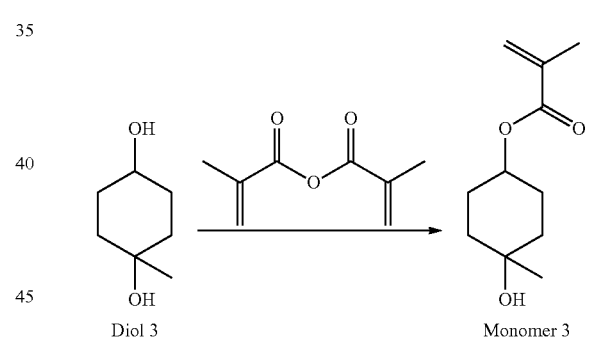

In nitrogen atmosphere, 28 g of methacrylic anhydride was added dropwise to a solution of 20 g of Diol 3 and 23 g of triethylamine in 100 mL of THF at room temperature. The contents were stirred at 40° C. for 8 hours. Then the reaction solution was ice cooled, to which 300 mL of a saturated aqueous solution of sodium hydrogencarbonate was added dropwise to quench the reaction. This was followed by ordinary aqueous workup, solvent distillation, and vacuum distillation, obtaining 24 g of Monomer 3 (yield 78%, isomer ratio=56/44). It is noted that the distillate gradually solidified into white crystals when stored at 5° C.

Figure 4:
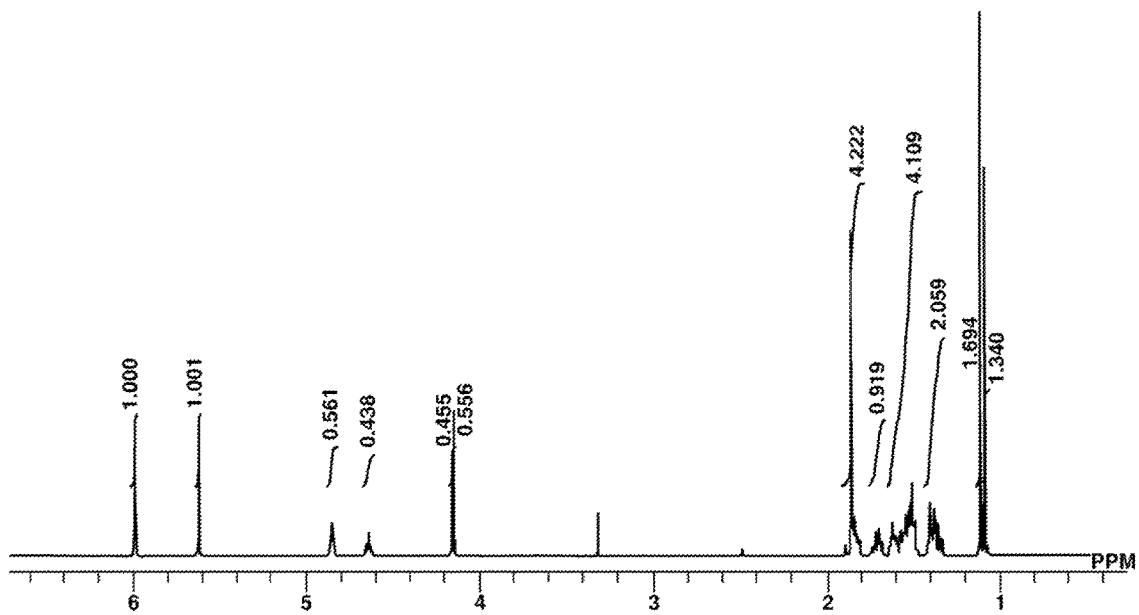
FIG. 4 is a diagram showing $^1$H-NMR spectrum of Monomer 3 in Example 3.

Analytical data of the target compound are shown below. FIG. 4 shows a $^1$H-NMR spectrum of the compound.

b.p.: 67° C./10 Pa

IR (D-ATR): v=3496, 2958, 2932, 1715, 1636, 1450, 1403, 1375, 1332, 1316, 1296, 1259, 1243, 1179, 1136, 1124, 1029, 1012, 970, 935, 917, 815, 725, 652, 603, 590, 568, 553 cm$^{-1}$

Example 4

Synthesis of Monomer 4

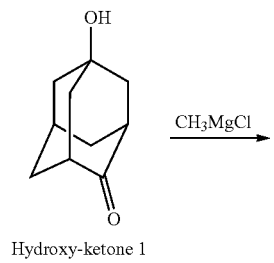

Hydroxy-ketone 1

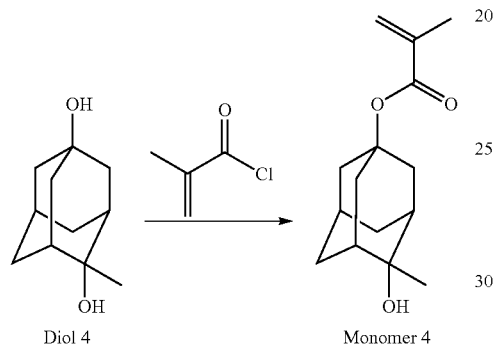

Diol 4    Monomer 4

Example 4-1

Synthesis of Diol 4

In nitrogen atmosphere, a solution of 100 g of Hydroxy-ketone 1 in 500 mL of THF was added dropwise to 1,800 mL of a THF solution of 1.0 mol/L methylmagnesium chloride at 25-45° C. The contents were stirred at 50° C. for 10 hours. Then the reaction solution was ice cooled, to which a mixture of 180 g of ammonium chloride and 1,500 g of a 2.4 wt % hydrochloric acid aqueous solution was added dropwise to quench the reaction. This was followed by ordinary aqueous workup, solvent distillation, crystallization from ethyl acetate and hexane, filtration, and drying, obtaining 80 g of Diol 4 (yield 78%, isomer ratio=62/38).

Figure 5:
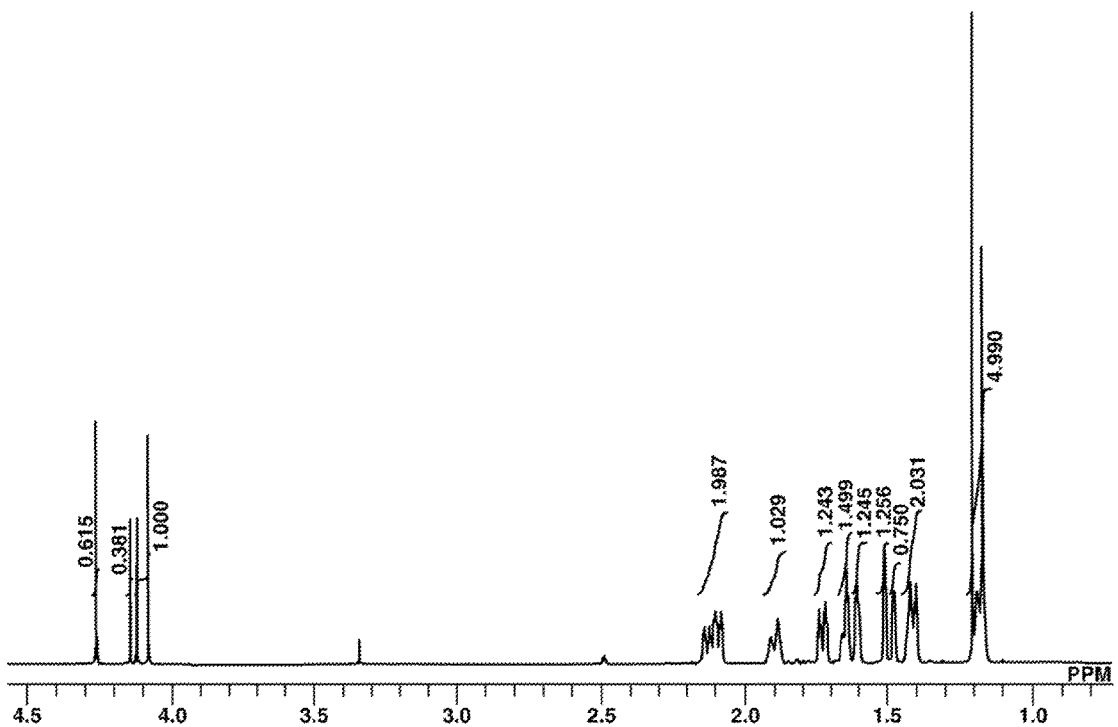
FIG. 5 is a diagram showing $^1$H-NMR spectrum of Diol 4 in Example 4-1.

Analytical data of the compound are shown below. FIG. 5 shows a $^1$H-NMR spectrum of the compound.

IR (D-ATR): v=3324, 2995, 2935, 2896, 2855, 1449, 1376, 1353, 1314, 1302, 1267, 1247, 1227, 1186, 1126, 1082, 1049, 1031, 973, 958, 931, 918, 890, 840, 803, 727, 669, 639 cm$^{-1}$

Example 4-2

Synthesis of Monomer 4

In nitrogen atmosphere, 63 g of methacryloyl chloride was added dropwise to a solution of 80 g of Diol 4 and 91 g of triethylamine in 700 mL of acetonitrile at room temperature. The contents were stirred at 40° C. for 3 hours. Then the reaction solution was ice cooled, to which 700 mL of water was added dropwise to quench the reaction. This was followed by ordinary aqueous workup, solvent distillation, and purification by silica gel column chromatography, obtaining 80 g of Monomer 4 (yield 73%, isomer ratio=54/46).

Figure 6:
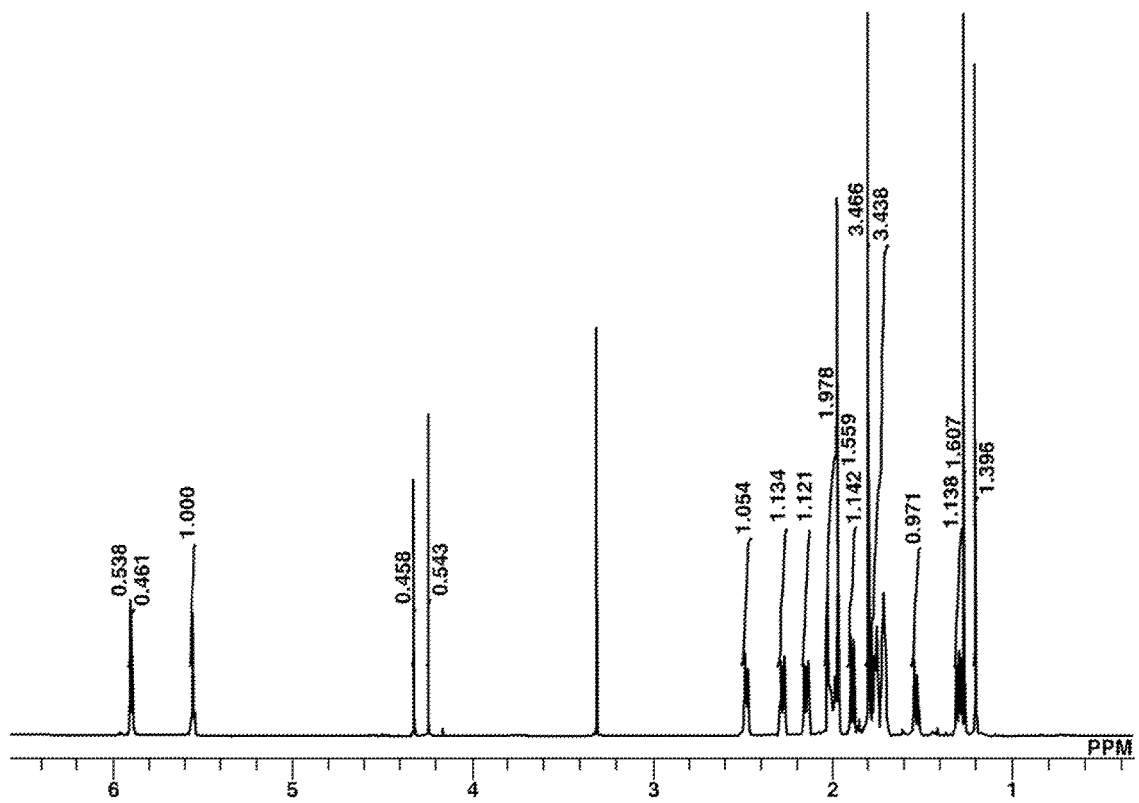
FIG. 6 is a diagram showing $^1$H-NMR spectrum of Monomer 4 in Example 4-2.

Analytical data of the target compound are shown below. FIG. 6 shows a $^1$H-NMR spectrum of the compound.

IR (D-ATR): v=3496, 2954, 2912, 2866, 1741, 1711, 1636, 1450, 1401, 1374, 1332, 1294, 1241, 1180, 1141, 1120, 1105, 1081, 1043, 1032, 1008, 935, 890, 858, 832, 814, 730, 698, 658, 561, 552 cm$^{-1}$

[2] Synthesis of Polymers

Examples 5 to 19 & Comparative Examples 1 to 10

Each of polymers (Polymers 1 to 15 and Comparative Polymers 1 to 10) for use in resist compositions was prepared by combining monomers in cyclopentanone solvent, effecting copolymerization reaction, crystallizing from hexane, washing with hexane several times, isolation and drying. The polymer was analyzed for composition by $^1$H-NMR and $^{13}$C-NMR spectroscopy.

Example 5

Polymer 1

Mw=8,600
Mw/Mn=1.67

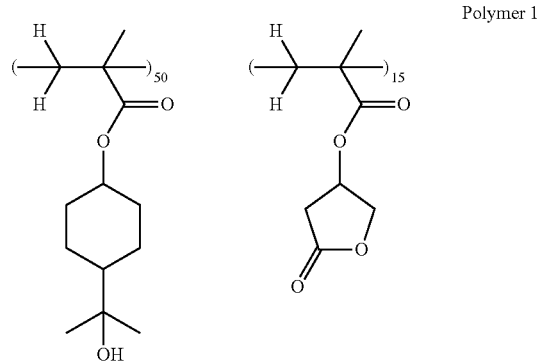

Polymer 1

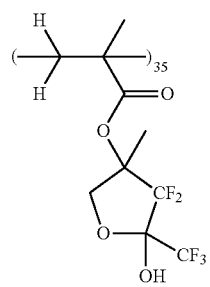

Example 6
Polymer 2
Mw=8,400
Mw/Mn=1.65
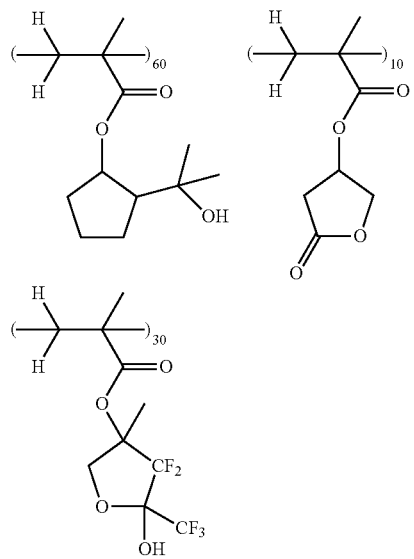
Polymer 2
Example 7
Polymer 3
Mw=8,300
Mw/Mn=1.67
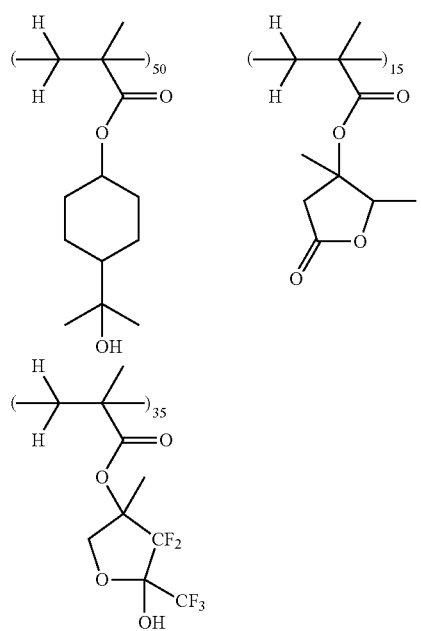
Polymer 3
Example 8
Polymer 4
Mw=8,300
Mw/Mn=1.66
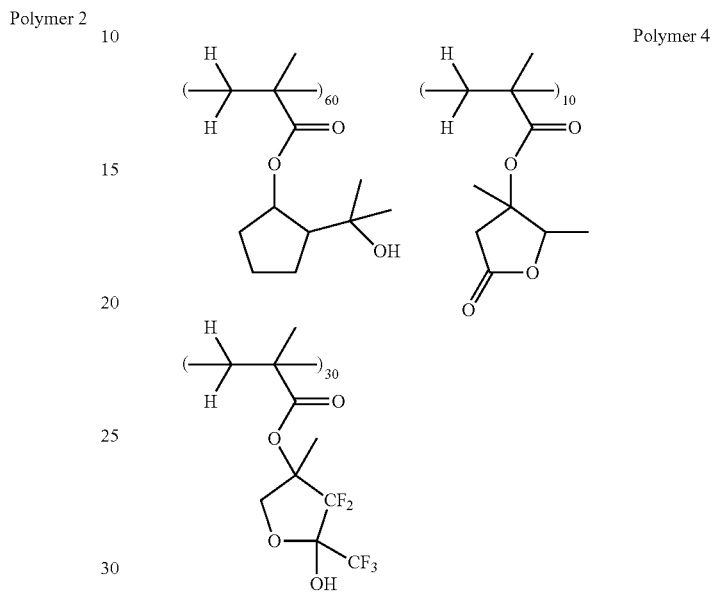
Polymer 4
Example 9
Polymer 5
Mw=8,500
Mw/Mn=1.66
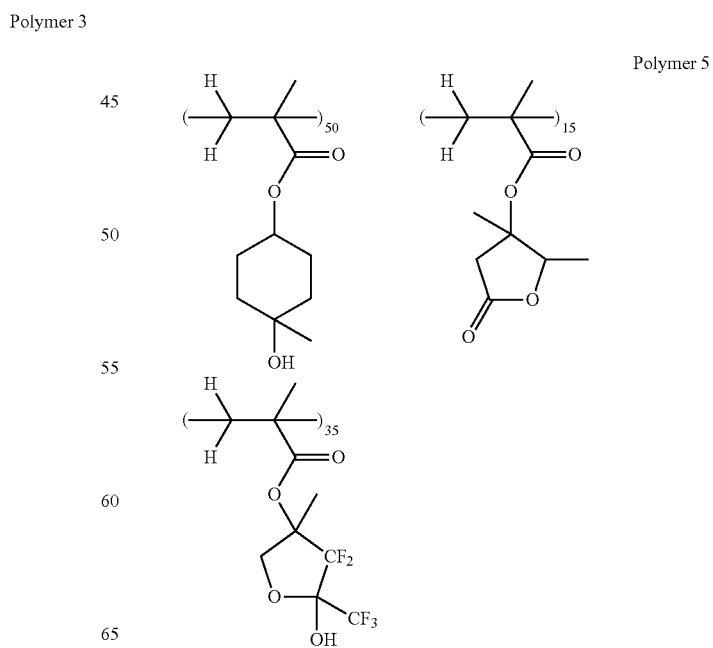
Polymer 5

Example 10

Polymer 6

Mw=8,900
Mw/Mn=1.71

Example 11

Polymer 7

Mw=8,800
Mw/Mn=1.72

Example 12

Polymer 8

Mw=8,500
Mw/Mn=1.68

Example 13
Polymer 9
Mw=8,700
Mw/Mn=1.70
Polymer 9
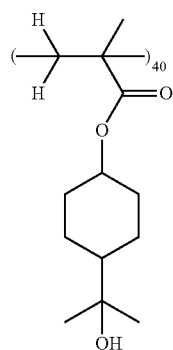
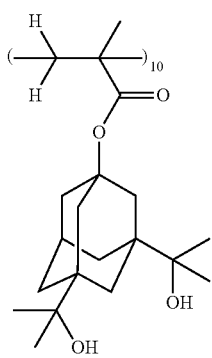
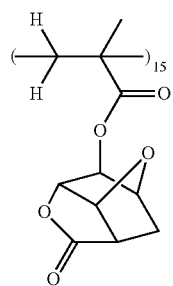
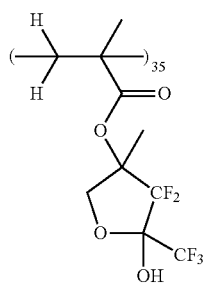
Example 14
Polymer 10
Mw=8,800
Mw/Mn=1.69
Polymer 10
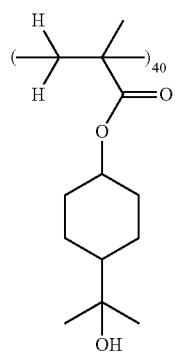
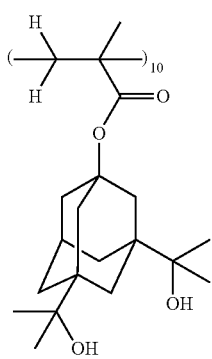
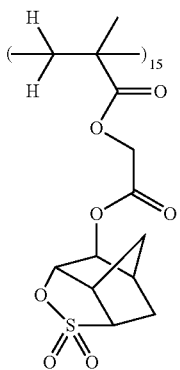
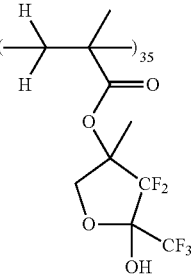
Example 15
Polymer 11
Mw=9,000
Mw/Mn=1.76
Polymer 11
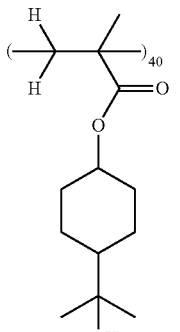
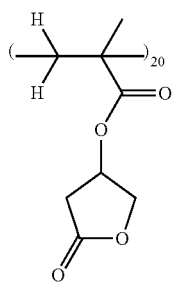
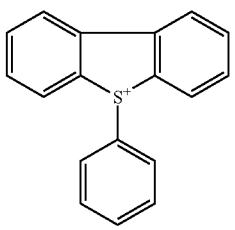
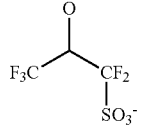

Example 16
Polymer 12
Mw=8,700
Mw/Mn=1.70
Polymer 12
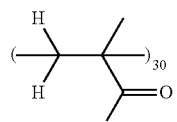
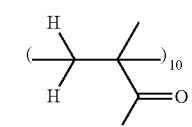
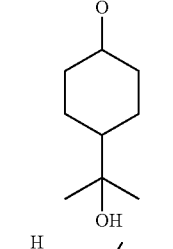
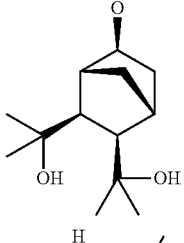
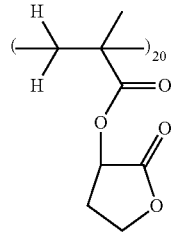
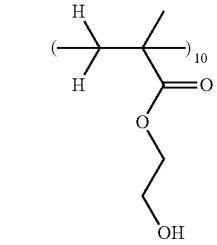
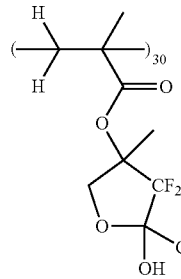
Example 17
Polymer 13
Mw=8,300
Mw/Mn=1.66
Polymer 13
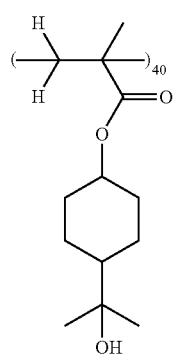
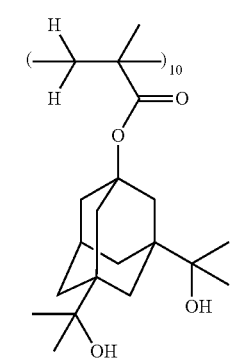
-continued
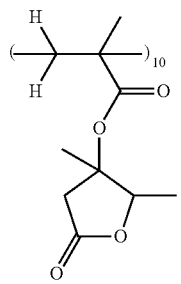
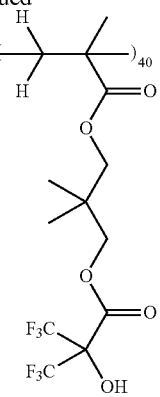
Example 18
Polymer 14
Mw=8,500
Mw/Mn=1.65
Polymer 14
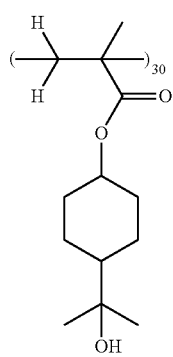
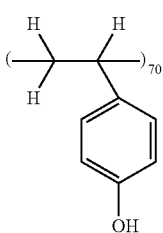
Example 19
Polymer 15
Mw=8,800
Mw/Mn=1.71
Polymer 15
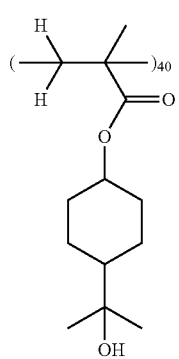
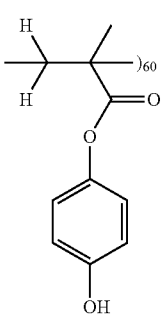

Comparative Example 1
Comparative Polymer 1
Mw=8,400
Mw/Mn=1.65
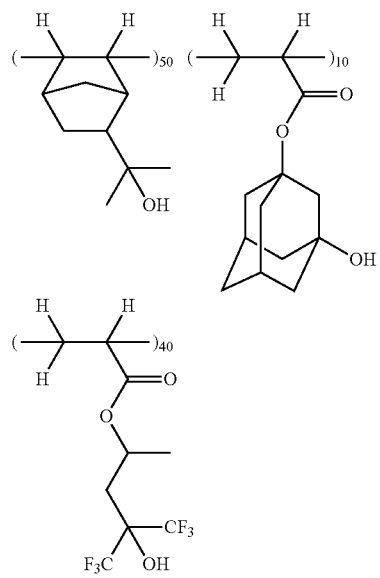
Comparative Polymer 1
Comparative Example 2
Comparative Polymer 2
Mw=8,500
Mw/Mn=1.63
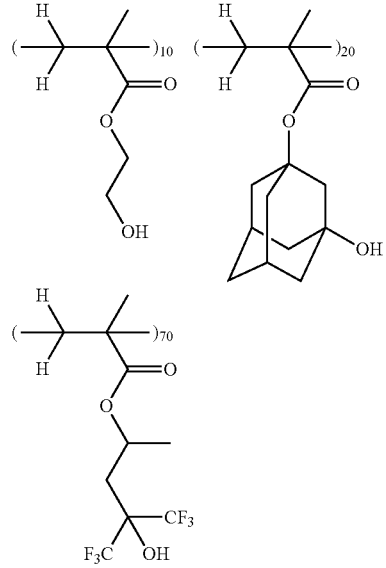
Comparative Polymer 2
Comparative Example 3
Comparative Polymer 3
Mw=8,700
Mw/Mn=1.65
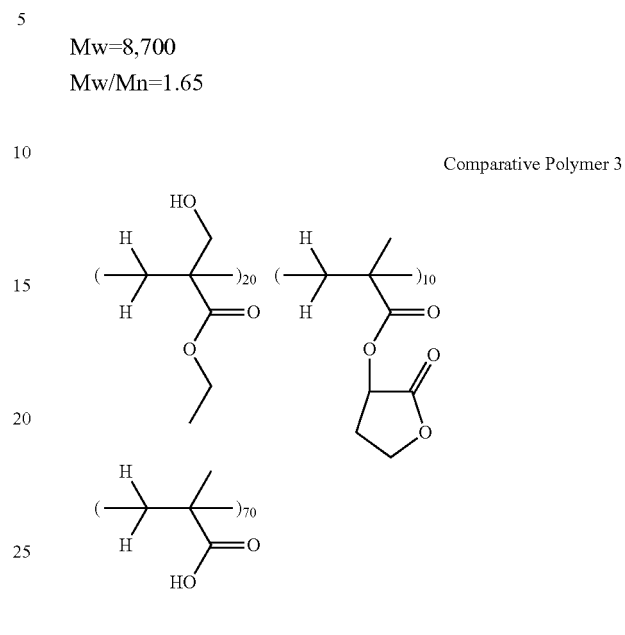
Comparative Polymer 3
Comparative Example 4
Comparative Polymer 4
Mw=8,600
Mw/Mn=1.62
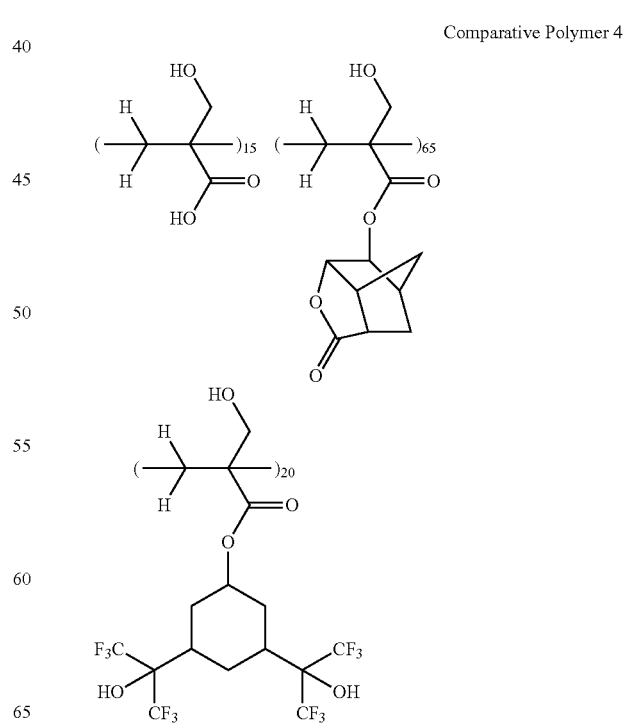
Comparative Polymer 4

Comparative Example 5
Comparative Polymer 5
Mw=8,400
Mw/Mn=1.66
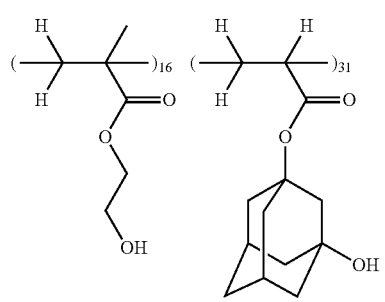
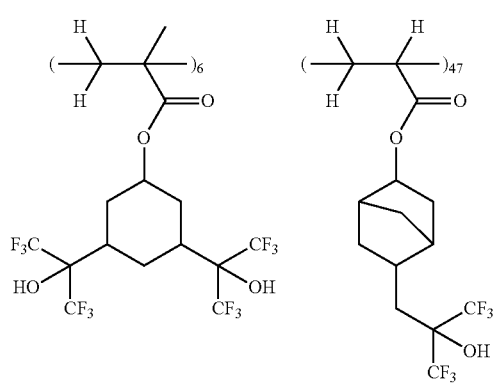
Comparative Polymer 5
Comparative Example 6
Comparative Polymer 6
Mw=8,600
Mw/Mn=1.63
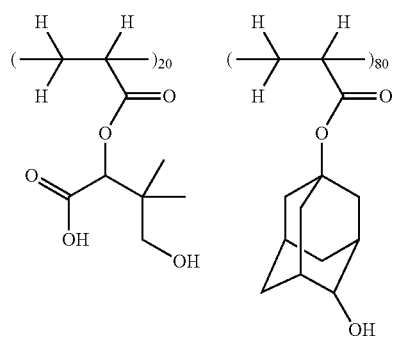
Comparative Polymer 6
Comparative Example 7
Comparative Polymer 7
Mw=8,600
Mw/Mn=1.63
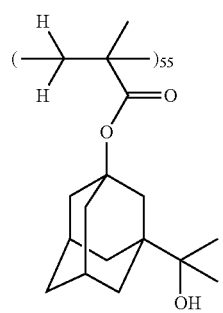
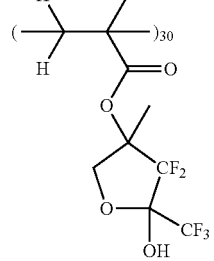
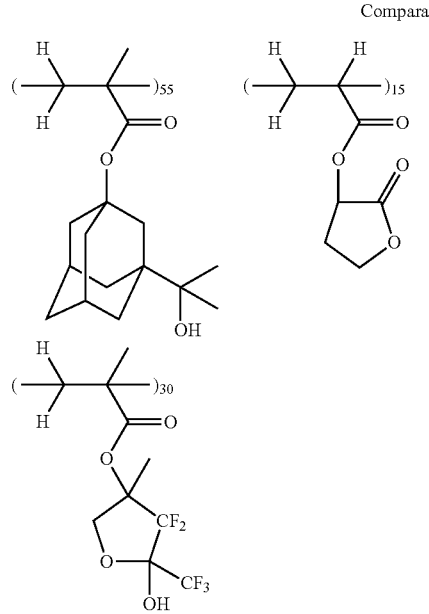
Comparative Polymer 7
Comparative Example 8
Comparative Polymer 8
Mw=8,500
Mw/Mn=1.61
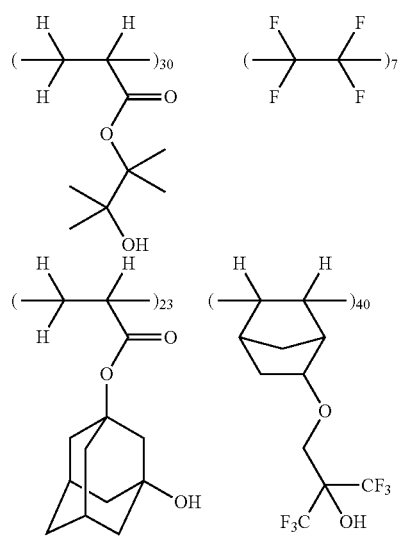
Comparative Polymer 8

Comparative Example 9

Comparative Polymer 9

Mw=8,400
Mw/Mn=1.65

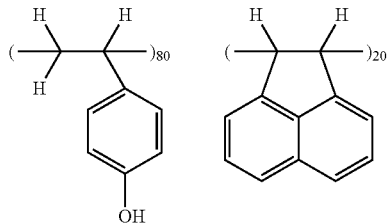

Comparative Polymer 9

Comparative Example 10

Comparative Polymer 10

Mw=8,400
Mw/Mn=1.65

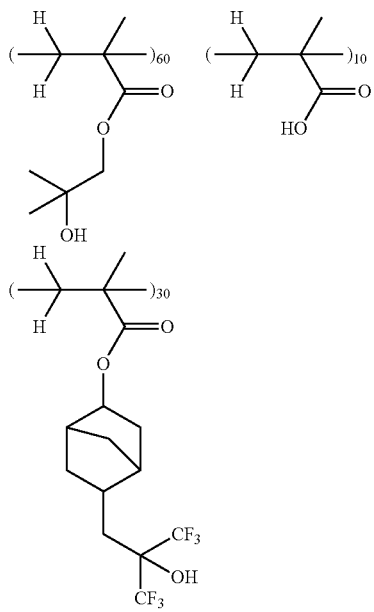

Comparative Polymer 10

[3] Preparation of Resist Compositions

Examples 20 to 34 & Comparative Examples 11 to 20

Resist compositions R-01 to R-25 were prepared by using inventive Polymers 1 to 15 or Comparative Polymers 1 to 10 as the base resin, dissolving the polymer and other components in a solvent in accordance with the recipe shown in Table 1, and filtering through a Teflon® filter having a pore size of 0.2 μm.

In Table 1, acid generator (PAG-1 to 4), water-repellent polymer (SF-1), sensitivity regulator (Q-1 to 4), crosslinker (XL-1), and solvent are as identified below.

Photoacid Generator: PAG-1 to PAG-4

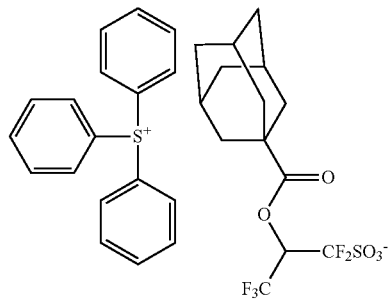

PAG-1

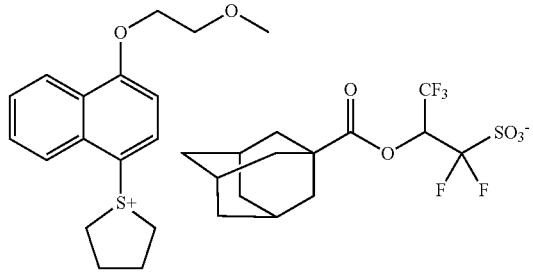

PAG-2

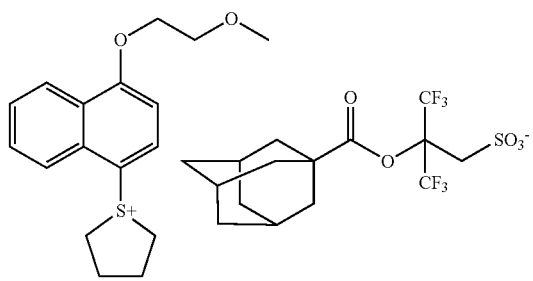

PAG-3

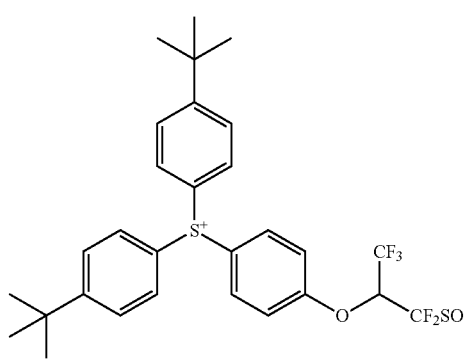

PAG-4

Sensitivity Regulator: Q-1 to Q-4

Water-Repellent Polymer: SF-1
Mw=8,700
Mw/Mn=1.85

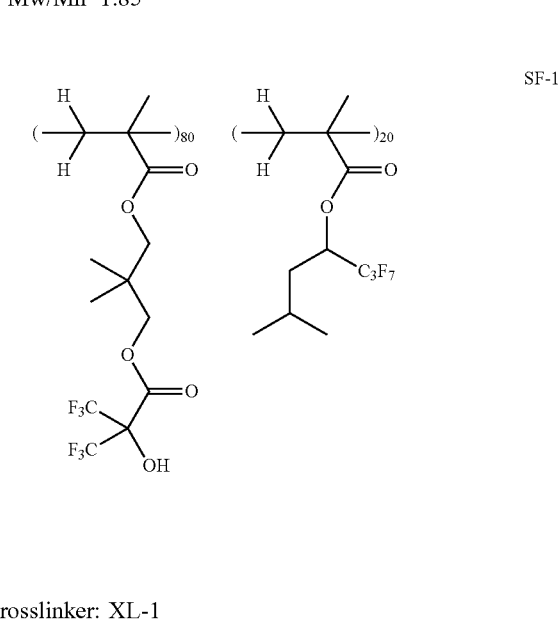

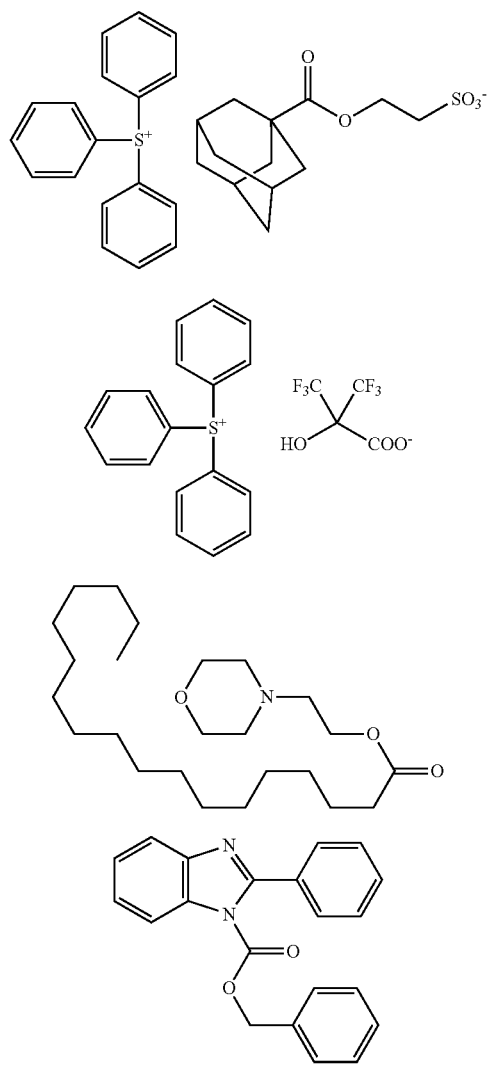

Crosslinker: XL-1

PGEE: propylene glycol monoethyl ether
DAA: diacetone alcohol
GBL: γ-butyrolactone

TABLE 1

|  |  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| Example | 20 | R-01 | Polymer 1 (100) | PAG-1 (6.0) | Q-3 (8.0) | SF-1 (5.0) | — | PGEE(2,000) DAA(400) GBL(100) |
|  | 21 | R-02 | Polymer 2 (100) | PAG-1 (6.0) | Q-1 (3.5) | SF-1 (5.0) | — | PGEE(2,000) DAA(400) GBL(100) |
|  | 22 | R-03 | Polymer 3 (100) | PAG-2 (6.0) | Q-4 (8.0) | SF-1 (5.0) | — | PGEE(2,000) DAA(400) GBL(100) |
|  | 23 | R-04 | Polymer 4 (100) | PAG-3 (6.0) | Q-4 (8.0) | SF-1 (5.0) | — | PGEE(2,000) DAA(400) GBL(100) |
|  | 24 | R-05 | Polymer 5 (100) | PAG-4 (6.0) | Q-3 (8.0) | SF-1 (5.0) | — | PGEE(2,000) DAA(400) GBL(100) |
|  | 25 | R-06 | Polymer 6 (100) | PAG-1 (6.0) | Q-2 (3.0) | SF-1 (5.0) | — | PGEE(2,000) DAA(400) GBL(100) |

TABLE 1-continued

|  |  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
|  | 26 | R-07 | Polymer 7 (100) | PAG-1 (6.0) | Q-1 (3.5) | SF-1 (5.0) | — | PGEE(2,000) DAA(400) GBL(100) |
|  | 27 | R-08 | Polymer 8 (100) | PAG-4 (6.0) | Q-2 (3.0) | SF-1 (5.0) | — | PGEE(2,000) DAA(400) GBL(100) |
|  | 28 | R-09 | Polymer 9 (100) | PAG-1 (6.0) | Q-3 (8.0) | SF-1 (5.0) | — | PGEE(2,000) DAA(400) GBL(100) |
|  | 29 | R-10 | Polymer 10 (100) | PAG-4 (6.0) | Q-4 (8.0) | SF-1 (5.0) | — | PGEE(2,000) DAA(400) GBL(100) |
|  | 30 | R-11 | Polymer 11 (100) | — | Q-4 (8.0) | SF-1 (5.0) | — | PGEE(2,000) DAA(400) GBL(100)) |
|  | 31 | R-12 | Polymer 12 (100) | PAG-1 (6.0) | Q-3 (8.0) | SF-1 (5.0) | XL-1 (5.0) | PGEE(2,000) DAA(400) GBL(100) |
|  | 32 | R-13 | Polymer 13 (100) | PAG-1 (6.0) | Q-1 (3.5) | SF-1 (5.0) | — | PGEE(2,000) DAA(400) GBL(100) |
|  | 33 | R-14 | Polymer 14 (100) | PAG-1 (6.0) | Q-3 (8.0) | SF-1 (5.0) | — | PGEE(2,000) DAA(400) GBL(100) |
|  | 34 | R-15 | Polymer 15 (100) | PAG-1 (6.0) | Q-3 (8.0) | SF-1 (5.0) | — | PGEE(2,000) DAA(400) GBL(100) |
| Comparative Example | 11 | R-16 | Comparative Polymer 1 (100) | PAG-2 (12.5) | Q-4 (1.5) | SF-1 (5.0) | — | PGEE(2,000) DAA(400) GBL(100) |
|  | 12 | R-17 | Comparative Polymer 2 (100) | PAG-4 (10.0) | Q-3 (1.5) | SF-1 (5.0) | XL-1 (5.0) | PGEE(2,000) DAA(400) GBL(100) |
|  | 13 | R-18 | Comparative Polymer 3 (100) | PAG-3 (12.5) | Q-4 (1.5) | SF-1 (5.0) | XL-1 (5.0) | PGEE(2,000) DAA(400) GBL(100) |
|  | 14 | R-19 | Comparative Polymer 4 (100) | PAG-1 (10.0) | Q-1 (1.5) | SF-1 (5.0) | XL-1 (5.0) | PGEE(2,000) DAA(400) GBL(100) |
|  | 15 | R-20 | Comparative Polymer 5 (100) | — | Q-1 (1.5) | SF-1 (5.0) | XL-1 (5.0) | PGEE(2,000) DAA(400) GBL(100) |
|  | 16 | R-21 | Comparative Polymer 6 (100) | PAG-1 (10.0) | Q-1 (1.5) | SF-1 (5.0) | — | PGEE(2,000) DAA(400) GBL(100) |
|  | 17 | R-22 | Comparative Polymer 7 (100) | PAG-1 (6.0) | Q-1 (3.5) | SF-1 (5.0) | — | PGEE(2,000) DAA(400) GBL(100) |
|  | 18 | R-23 | Comparative Polymer 8 (100) | PAG-1 (10.0) | Q-3 (1.5) | SF-1 (5.0) | XL-1 (5.0) | PGEE(2,000) DAA(400) GBL(100) |
|  | 19 | R-24 | Comparative Polymer 9 (100) | PAG-1 (10.0) | Q-3 (1.5) | SF-1 (5.0) | XL-1 (5.0) | PGEE(2,000) DAA(400) GBL(100) |
|  | 20 | R-25 | Comparative Polymer 10 (100) | PAG-1 (6.0) | Q-3 (1.5) | SF-1 (5.0) | — | PGEE(2,000) DAA(400) GBL(100) |

[4] Evaluation of Swell Quantity of Resist During Development, by the QCM (Quartz Crystal Microbalance) Technique Examples 35 to 38 & Comparative Example 21

The above-prepared resist solution (in Table 1) was spin coated on a QCM substrate and baked on a hot plate at 100° C. for 60 seconds to form a resist film of 100 nm thick. The resist film was exposed by means of an ArF open-frame exposure system in a dose varying stepwise from 1 mJ/cm$^2$ to 13 mJ/cm$^2$ by an increment of 1 mJ/cm$^2$ and baked (PEB) on a hot plate at the temperature shown in Table 2 for 60 seconds. The QCM substrate was set on a quartz oscillator microbalance instrument RDA-Qz3 for resist development analysis (Litho Tech Japan Co., Ltd.). Development in a 2.38 wt % TMAH aqueous solution was carried out, during which a variation of thickness of resist film was observed as a function of development time. From graphs in which a film thickness variation was plotted relative to development time for each dose, the exposure dose corresponding to the maximum swell quantity and the maximum swell ratio (maximum swell quantity standardized per initial film thickness) are determined, with the results shown in Table 2. A smaller value of maximum swell ratio indicates that the swell of resist film is suppressed.

TABLE 2

|  |  | Resist | PEB temp. (° C.) | Dose (mJ/cm²) | Maximum swell ratio (%) |
|---|---|---|---|---|---|
| Example | 35 | R-02 | 100 | 7 | 120 |
|  | 36 | R-05 | 105 | 7 | 110 |
|  | 37 | R-06 | 100 | 7 | 105 |
|  | 38 | R-07 | 100 | 5 | 120 |
| Comparative Example | 21 | R-17 | 100 | 7 | 191 |

As is evident from Table 2, the resist compositions within the scope of the invention show lower maximum swell ratios than the comparative resist compositions.

[5] Etch Resistance Test

Examples 39 to 41 & Comparative Examples 22 to 24

On a silicon wafer which had been surface treated in hexamethyldisilazane (HMDS) gas phase at 90° C. for 60 seconds, the resist solution in Table 1 was spin-coated and baked (PAB) on a hot plate at 100° C. for 60 seconds, forming a resist film of 100 nm thick. Using an ArF excimer laser scanner (NSR-307E by Nikon Corp., NA 0.85), the entire surface of the wafer was subjected to open-frame exposure. The exposure dose was 50 mJ/cm² so that the PAG might generate sufficient acid to induce deprotection reaction. This was followed by PEB at the temperature shown in Table 3 for 60 seconds for promoting dehydration or crosslinking reaction on the base resin of the resist film. The portion where the base resin has underwent dehydration reaction corresponds to the insoluble region in development. A reduction of resist film thickness by exposure and PEB was determined and divided by the initial film thickness, with the result being reported as PEB shrinkage (%).

Further, the resist film was developed in a 2.38 wt % TMAH aqueous solution for 30 seconds. The thickness of the resist film after development was measured. A minimum dissolution rate (nm/sec) was computed from a difference between the film thickness after PEB and the film thickness after development. A lower PEB shrinkage or lower minimum dissolution rate is preferable in that a film thickness necessary for dry etching is retained, or the initial film thickness can be reduced, which is advantageous in terms of resolution. The results are shown in Table 3.

TABLE 3

|  |  | Resist | PEB temp. (° C.) | PEB shrinkage (%) | Minimum dissolution rate (nm/sec) |
|---|---|---|---|---|---|
| Example | 39 | R-08 | 105 | 95 | 0.01 |
|  | 40 | R-09 | 100 | 93 | 0.02 |
|  | 41 | R-10 | 105 | 94 | 0.02 |
| Comparative Example | 22 | R-21 | 100 | 85 | 0.05 |
|  | 23 | R-22 | 100 | 92 | 0.1 |
|  | 24 | R-25 | 100 | 93 | 0.15 |

As is evident from Table 3, the resist compositions within the scope of the invention show a low PEB shrinkage and a slow minimum dissolution rate. As a result, the patterned film is left thick after development, and etch resistance after patterning is high.

[6] ArF Lithography Patterning Test 1

Examples 42 to 53 & Comparative Examples 25 to 33

On a silicon wafer which had been coated with antireflective coating ARC29A (Nissan Chemical Industries, Ltd.) to a thickness of 78 nm, the resist composition (in Table 1) was spin coated, then baked on a hot plate at 100° C. for 60 seconds to form a resist film of 100 nm thick. Using an ArF excimer laser scanner NSR-S307E (Nikon Corp., NA 0.85, a 0.93/0.74, annular illumination), exposure was performed through a 6% halftone phase shift mask bearing a line-and-space pattern with a space width of 90 nm and a pitch of 180 nm, a space width of 80 nm and a pitch of 160 nm or a space width of 70 nm and a pitch of 140 nm (on-wafer size) or a trench pattern with a space width of 90 nm and a pitch of 1,650 nm (on-wafer size) while varying the dose and focus (dose pitch: 1 mJ/cm², focus pitch: 0.025 μm). After the exposure, the wafer was baked (PEB) at the temperature shown in Table 4 for 60 seconds and puddle developed in 2.38 wt % TMAH aqueous solution for 30 seconds. The wafer was rinsed with deionized water and spin dried, forming a negative pattern. The L/S patterns and trench pattern after development were observed under TD-SEM S-9380 (Hitachi Hitechnologies, Ltd.).

[Evaluation of Sensitivity]

As an index of sensitivity, the optimum dose (Eop, mJ/cm²) which provided an L/S pattern with a space width of 90 nm and a pitch of 180 nm was determined. A smaller dose value indicates a higher sensitivity.

[Evaluation of Exposure Latitude (EL)]

The exposure dose which provided an L/S pattern with a space width of 90 nm±10% (i.e., 81 nm to 99 nm) was determined. EL (%) is calculated from the exposure doses according to the following equation:

$$EL(\%) = (|E1 - E2|/Eop) \times 100$$

wherein E1 is an exposure dose which provides an L/S pattern with a space width of 81 nm and a pitch of 180 nm, E2 is an exposure dose which provides an L/S pattern with a space width of 99 nm and a pitch of 180 nm, and Eop is the optimum exposure dose which provides an L/S pattern with a space width of 90 nm and a pitch of 180 nm.

[Evaluation of Line Width Roughness (LWR)]

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

[Evaluation of Depth of Focus (DOP)]

As an index of DOP, a range of focus which provided a trench pattern with a space width of 90 nm±10% (i.e., 81 to 99 nm) was determined. A greater value indicates a wider DOP.

[Evaluation of Resolution]

Resolution is the minimum size that can be resolved among the L/S patterns with a size from 70 nm to 90 nm (pitch 140 to 180 nm). A smaller value indicates better resolution.

The results are shown in Table 4.

TABLE 4

|  |  | Resist | PEB temp. (° C.) | Eop (mJ/cm²) | EL (%) | LWR (nm) | DOF (μm) | Resolution (nm) |
|---|---|---|---|---|---|---|---|---|
| Example | 42 | R-01 | 100 | 35.5 | 15.4 | 6.4 | 0.18 | 70 |
|  | 43 | R-02 | 100 | 32.0 | 14.7 | 6.3 | 0.18 | 70 |
|  | 44 | R-03 | 100 | 38.5 | 17.6 | 6.7 | 0.15 | 70 |
|  | 45 | R-04 | 100 | 31.5 | 13.6 | 6.2 | 0.16 | 70 |
|  | 46 | R-05 | 100 | 43.4 | 14.4 | 7.7 | 0.17 | 70 |
|  | 47 | R-06 | 100 | 42.9 | 13.7 | 7.1 | 0.17 | 70 |
|  | 48 | R-07 | 105 | 46.3 | 15.3 | 7.4 | 0.17 | 70 |
|  | 49 | R-08 | 100 | 48.1 | 15.0 | 6.0 | 0.16 | 70 |
|  | 50 | R-09 | 95 | 49.2 | 16.9 | 6.2 | 0.18 | 70 |
|  | 51 | R-10 | 95 | 33.6 | 15.8 | 5.8 | 0.16 | 70 |
|  | 52 | R-12 | 95 | 30.2 | 17.4 | 7.4 | 0.18 | 80 |
|  | 53 | R-13 | 100 | 33.5 | 15.7 | 6.1 | 0.17 | 70 |
| Comparative | 25 | R-16 | 100 | 36.3 | 9.5 | 10.3 | 0.10 | 90 |
| Example | 26 | R-17 | 95 | 25.3 | 10.5 | 9.8 | 0.08 | 90 |
|  | 27 | R-18 | 110 | 28.3 | 8.3 | 11.5 | 0,10 | 90 |
|  | 28 | R-19 | 100 | 38.5 | 5.6 | 15.2 | 0.12 | 90 |
|  | 29 | R-20 | 100 | 35.6 | 7.5 | 9.5 | 0.08 | 90 |
|  | 30 | R-21 | 110 | 30.5 | 6 | 16.3 | 0.10 | 90 |
|  | 31 | R-22 | 100 | 45.3 | 10.1 | 13.2 | 0.10 | 90 |
|  | 32 | R-23 | 100 | 33.3 | 6.6 | 10.7 | 0.08 | 90 |
|  | 33 | R-25 | 100 | 39.6 | 10.2 | 10.7 | 0.07 | 90 |

As is evident from Table 4, the resist compositions within the scope of the invention have practically acceptable sensitivity. Both EL and DOF have a wide margin. LWR is low as compared with the resists of Comparative Examples. Resolution is also excellent.

[7] ArF Lithography Patterning Test 2

Examples 54 to 57 & Comparative Example 34

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A940 having a silicon content of 43 wt % was deposited thereon to a thickness of 35 nm. On this substrate for trilayer process, the resist composition (in Table 1) was spin coated, then baked on a hot plate at 100° C. for 60 seconds to form a resist film of 60 nm thick. Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 55 nm and a pitch of 110 nm (on-wafer size) while varying the dose and focus (dose pitch: 1 mJ/cm², focus pitch: 0.025 μm). After the exposure, the wafer was baked (PEB) at the temperature shown in Table 5 for 60 seconds and puddle developed in 2.38 wt % TMAH aqueous solution for 30 seconds. The wafer was rinsed with deionized water and spin dried, obtaining a negative pattern. The CH pattern after development was observed under TD-SEM CG4000 (Hitachi Hitechnologies, Ltd.).

[Evaluation of Sensitivity]

As an index of sensitivity, the optimum dose (Eop, mJ/cm²) which provided a CH pattern with a hole size of 55 nm and a pitch of 110 nm was determined. A smaller dose value indicates a higher sensitivity.

[Evaluation of Exposure Latitude (EL)]

The exposure dose which provided a CH pattern with a hole size of 55 nm±10% (i.e., 49.5 nm to 60.5 nm) was determined. EL (%) is calculated from the exposure doses according to the following equation:

EL(%)=(|E1−E2|/Eop)×100 wherein E1 is an exposure dose which provides a CH pattern with a hole size of 49.5 nm and a pitch of 110 nm, E2 is an exposure dose which provides a CH pattern with a hole size of 60.5 nm and a pitch of 110 nm, and Eop is the optimum exposure dose which provides a CH pattern with a hole size of 55 nm and a pitch of 110 nm.

[Evaluation of Critical Dimension Uniformity (CDU)]

For the CH pattern formed by exposure in the optimum dose (determined in the sensitivity evaluation), the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

The results are shown in Table 5.

TABLE 5

|  |  | Resist | PEB temp. (° C.) | Eop (mJ/cm²) | EL (%) | CDU 3σ (nm) |
|---|---|---|---|---|---|---|
| Example | 54 | R-02 | 100 | 24.3 | 9.8 | 7.0 |
|  | 55 | R-08 | 95 | 32.3 | 12.3 | 6.6 |
|  | 56 | R-09 | 100 | 37.5 | 12.4 | 6.3 |
|  | 57 | R-10 | 90 | 33.4 | 10.3 | 6.9 |
| Comparative Example | 34 | R-16 | 100 | 22.3 | 7.2 | 10.1 |

As is evident from Table 5, the resist compositions within the scope of the invention show practically acceptable sensitivity, a wide margin of EL, and excellent CDU.

[8] EB Writing Test

Examples 58 to 61 & Comparative Examples 35 to 36

On a silicon wafer which had been surface treated in HMDS gas phase at 90° C. for 60 seconds, each of the inventive resist compositions or comparative resist compositions in Table 1 was spin coated and prebaked on a hot plate at 100° C. for 60 seconds to form a resist film of 60 nm thick. Using an EB lithography system JBX-9000 (JEOL, Ltd.) at an accelerating voltage of 50 kV, a L/S pattern having a space width of 100 nm and a pitch of 200 nm (on-wafer size) was written while varying the dose (dose variation pitch 2 μC/cm²). After the imagewise exposure, the resist film was baked (PEB) at the temperature shown in Table 6 for 60 seconds, puddle developed in 2.38 wt % TMAH aqueous solution for 30 seconds, rinsed with deionized water, and spin dried, obtaining a negative pattern. The L/S pattern after development was observed under TD-SEM S-9380 (Hitachi Hitechnologies, Ltd.).

[Evaluation of Sensitivity]

As an index of sensitivity, the optimum dose (Eop, μC/cm²) which provided an L/S pattern with a space width of 100 nm and a pitch of 200 nm was determined. A smaller dose value indicates a higher sensitivity.

[Evaluation of Exposure Latitude (EL)]

The exposure dose which provided an L/S pattern with a space width of 100 nm±10% (i.e., 90 nm to 110 nm) was determined. EL (%) is calculated from the exposure doses according to the following equation:

$$EL(\%)=(|E1-E2|/Eop)\times 100$$

wherein E1 is an exposure dose which provides an L/S pattern with a space width of 90 nm and a pitch of 200 nm, E2 is an exposure dose which provides an L/S pattern with a space width of 110 nm and a pitch of 200 nm, and Eop is the optimum exposure dose which provides an L/S pattern with a space width of 100 nm and a pitch of 200 nm.

[Evaluation of Line Width Roughness (LWR)]

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Table 6.

TABLE 6

|  |  | Resist | PEB temp. (° C.) | Eop (μC/cm²) | EL (%) | LWR (nm) |
|---|---|---|---|---|---|---|
| Example | 58 | R-02 | 100 | 43.3 | 13.1 | 5.3 |
|  | 59 | R-11 | 100 | 50.4 | 18.7 | 4.4 |
|  | 60 | R-14 | 110 | 39.5 | 13.6 | 5.3 |
|  | 61 | R-15 | 115 | 38.1 | 15.2 | 5.7 |
| Comparative | 35 | R-16 | 100 | 42.2 | 8.6 | 8.9 |
| Example | 36 | R-24 | 105 | 53.5 | 7.2 | 9.5 |

As is evident from Table 6, the resist compositions within the scope of the invention show practically acceptable sensitivity, a wide margin of EL, and low LWR.

Japanese Patent Application No. 2015-101654 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units having the formula (1a) and/or (1b) and recurring units having the formula (1c):

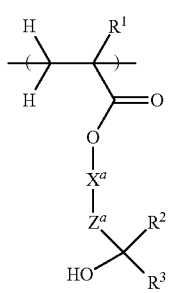

(1a)

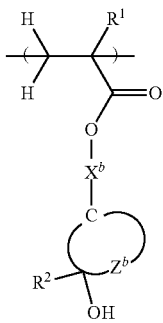

(1b)

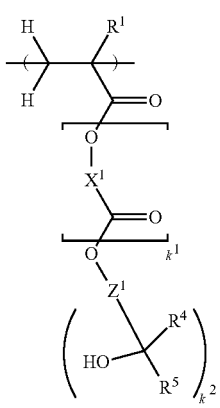

(1c)

wherein $R^1$ is hydrogen or methyl, $R^2$ and $R^3$ are each independently a straight, branched or cyclic $C_1$-$C_6$ monovalent hydrocarbon group, $R^2$ and $R^3$ may bond together to form an alicyclic group with the carbon atom to which they are attached, $X^a$ and $X^b$ are each independently a single bond, methylene or ethylidene, $Z^a$ is a branched or cyclic $C_1$-$C_9$ divalent aliphatic hydrocarbon group, $Z^b$ is an atomic group necessary to form a $C_3$-$C_{10}$ alicyclic group with the carbon atoms to which it is attached, with the proviso that the total number of carbon atoms in each formula is such as to meet $6 \leq X^a+Z^a+R^2+R^3 \leq 12$ when $Z^a$ is acyclic, or $5 \leq X^a+Z^a+R^2+R^3 \leq 12$ when $Z^a$ is cyclic, and $5 \leq X^b+Z^b+R^2 \leq 12$, $R^4$ and $R^5$ are each independently a straight, branched or cyclic $C_1$-$C_{10}$ monovalent hydrocarbon group, $R^4$ and $R^5$ may bond together to form an alicyclic group with the carbon atom to which they are attached, $X^1$ is a straight, branched or cyclic $C_1$-$C_{20}$ divalent hydrocarbon group in which any constituent —$CH_2$— moiety may be replaced by —O— or —C(=O)—, $Z^1$ is a straight, branched or cyclic $C_1$-$C_{20}$ tri- to pentavalent aliphatic hydrocarbon group in which any constituent —$CH_2$— moiety may be replaced by —O— or —C(=O)—, $k^1$ is 0 or 1, and $k^2$ is an integer of 2 to 4.

2. The polymer of claim 1 wherein the straight, branched or cyclic $C_1$-$C_{20}$ tri- to pentavalent aliphatic hydrocarbon group represented by $Z^1$ is selected from the group consisting of the following formulae:

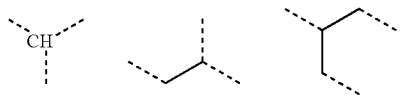

-continued

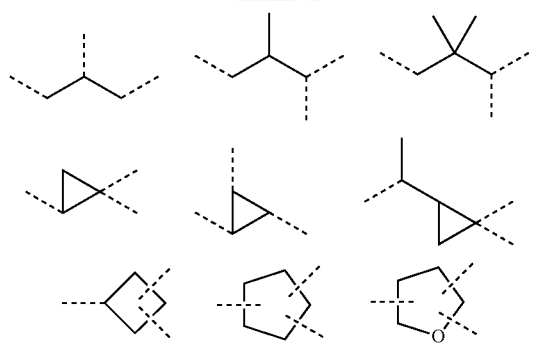

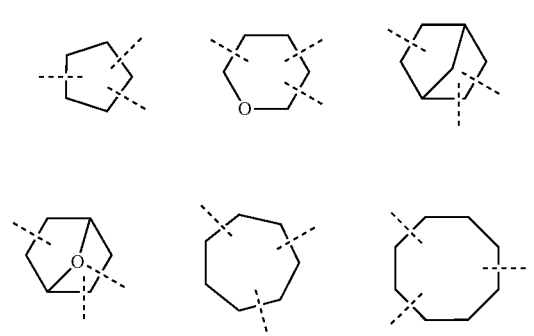

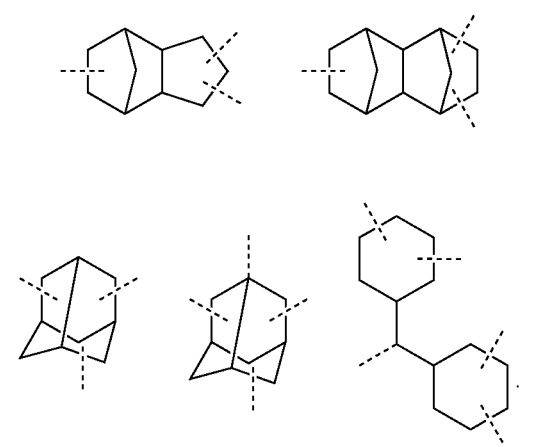

3. A polymer comprising recurring units having the formula (1a) and/or (1b) and recurring units of at least one type selected from the formulae (A), (B) and (D):

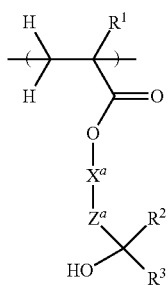
(1a)

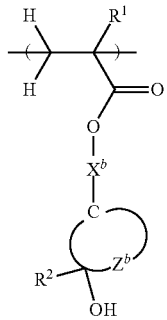
(1b)

wherein $R^1$ is hydrogen or methyl, $R^2$ and $R^3$ are each independently a straight, branched or cyclic $C_1$-$C_6$ monovalent hydrocarbon group, $R^2$ and $R^3$ may bond together to form an alicyclic group with the carbon atom to which they are attached, $X^a$ and $X^b$ are each independently a single bond, methylene or ethylidene, $Z^a$ is a branched or cyclic $C_1$-$C_9$ divalent aliphatic hydrocarbon group, $Z^b$ is an atomic group necessary to form a $C_3$-$C_{10}$ alicyclic group with the carbon atoms to which it is attached, with the proviso that the total number of carbon atoms in each formula is such as to meet $6 \leq X^a + Z^a + R^2 + R^3 \leq 12$ when $Z^a$ is acyclic, or $5 \leq X^a + Z^a + R^2 + R^3 \leq 12$ when $Z^a$ is cyclic, and $5 \leq X^b + Z^b + R^2 \leq 12$, wherein the $C_3$-$C_{10}$ alicyclic group is selected from the group consisting of the following formulae:

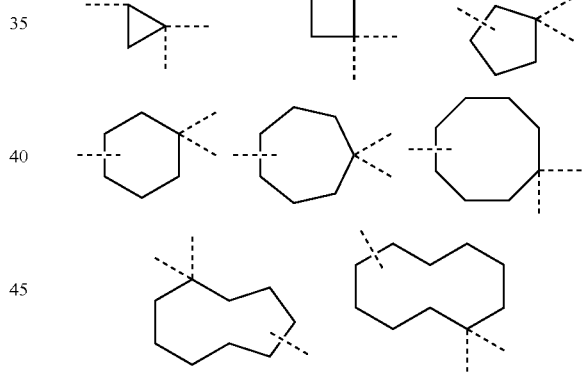

wherein the broken line denotes a valence bond,

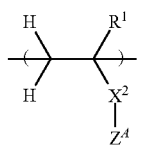
(A)

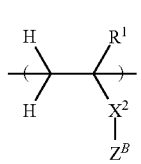
(B)

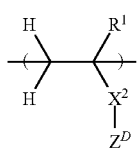

(D)

wherein R¹ is hydrogen or methyl, $Z^A$ is a $C_1$-$C_{20}$ fluoroalcohol-containing group, $Z^B$ is a $C_1$-$C_{20}$ phenolic hydroxyl-containing group, $Z^D$ is a group containing a lactone structure, sultone structure, carbonate structure, acid anhydride structure, alkoxycarbonyl moiety, sulfonamide moiety or carbamoyl moiety, X² is a single bond, methylene, ethylene, phenylene, fluorinated phenylene, naphthylene, —O—$R^{01}$—, or —C(=O)—$Z^2$—$R^{01}$—, $Z^2$ is oxygen or NH, $R^{01}$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety, wherein the recurring unit of formula (B) is selected from the group consisting of the following formulae:

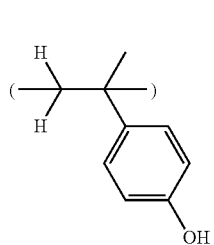 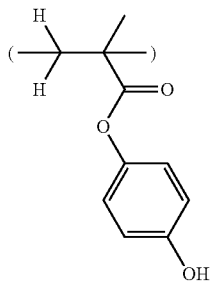

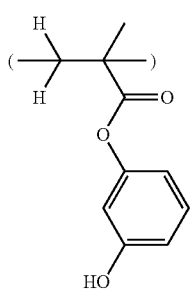 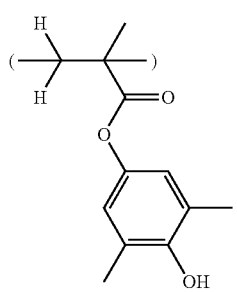

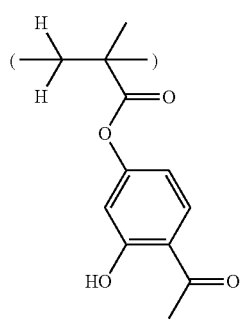 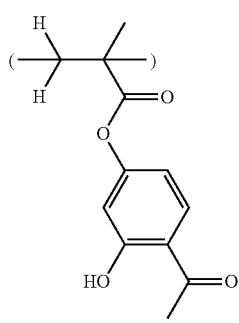

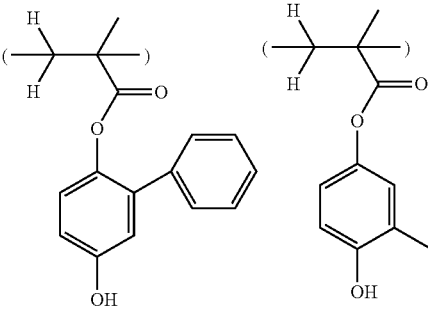

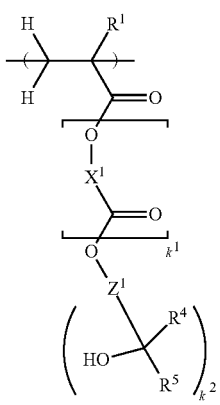

4. The polymer of claim 3, further comprising recurring units having the formula (1c):

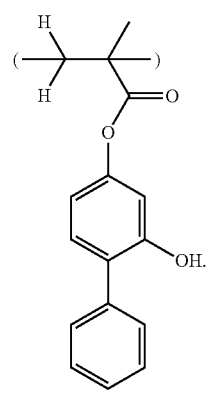

(1c)

wherein R¹ is hydrogen or methyl, R⁴ and R⁵ are each independently a straight, branched or cyclic $C_1$-$C_{10}$ monovalent hydrocarbon group, R⁴ and R⁵ may bond together to form an alicyclic group with the carbon atom to which they are attached, X¹ is a straight, branched or cyclic $C_1$-$C_{20}$ divalent hydrocarbon group in which any constituent —CH₂— moiety may be replaced by —O— or —C(=O)—, Z¹ is a straight, branched or cyclic $C_1$-$C_{20}$ tri- to pentavalent aliphatic hydrocarbon group in which any constituent —CH₂— moiety may be replaced by —O— or —C(=O)—, k¹ is 0 or 1, and k² is an integer of 2 to 4.

5. The polymer of claim 3, further comprising recurring units of at least one type selected from the formulae (f1) to (f3):

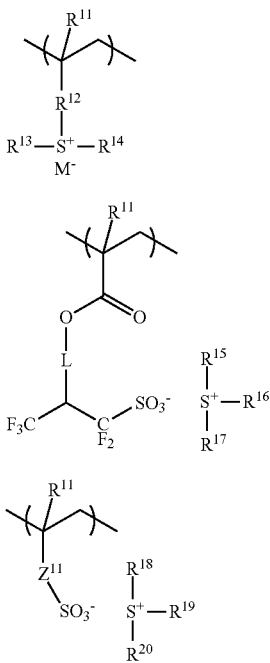

(f1)

(f2)

(f3)

wherein $R^{11}$ is independently hydrogen or methyl, $R^{12}$ is a single bond, phenylene, —O—$R^{21}$—, or —C(=O)—$Z^{22}$—$R^{21}$—, $Z^{22}$ is oxygen or NH, $R^{21}$ is a straight, branched or cyclic $C_1$-$C_6$ alkylene, straight, branched or cyclic $C_2$-$C_6$ alkenylene or phenylene group, which may contain a carbonyl (—CO—), ester (—COO—), ether (—O—) or hydroxyl moiety, L is a single bond or —$Z^{33}$—C(=O)—O—, $Z^{33}$ is a straight, branched or cyclic $C_1$-$C_{20}$ divalent hydrocarbon group which may be substituted with a heteroatom, $Z^{11}$ is a single bond, methylene, ethylene, phenylene, fluorinated phenylene, —O—$R^{22}$—, or —C(=O)—$Z^{44}$—$R^{22}$—, $Z^{44}$ is oxygen or NH, $R^{22}$ is a straight, branched or cyclic $C_1$-$C_6$ alkylene, straight, branched or cyclic $C_2$-$C_6$ alkenylene or phenylene group, which may contain a carbonyl, ester, ether or hydroxyl moiety, $R^{13}$ to $R^{20}$ are each independently a straight, branched or cyclic $C_1$-$C_{20}$ monovalent hydrocarbon group which may be substituted with or separated by a heteroatom, and $M^-$ is a non-nucleophilic counter ion.

6. A resist composition comprising a base resin comprising the polymer of claim 5, and an organic solvent.

7. A resist composition comprising a base resin comprising the polymer of claim 3, an acid generator, and an organic solvent.

8. The polymer of claim 3 wherein $X^a$ is a single bond, and $Z^a$ is a branched or cyclic $C_1$-$C_9$ divalent aliphatic hydrocarbon group.

9. The polymer of claim 3 wherein the branched or cyclic $C_1$-$C_9$ divalent aliphatic hydrocarbon group represented by $Z^a$ is selected from the group consisting of the following formulae:

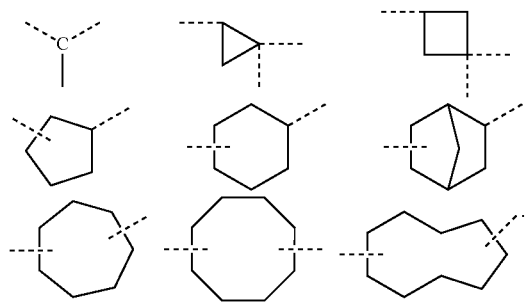

* * * * *